US012270810B2

(12) United States Patent
Chou et al.

(10) Patent No.: US 12,270,810 B2
(45) Date of Patent: *Apr. 8, 2025

(54) QMAX ASSAY AND APPLICATIONS (II)

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/484,035

(22) PCT Filed: Feb. 9, 2018

(86) PCT No.: PCT/US2018/017712

§ 371 (c)(1),
(2) Date: Aug. 6, 2019

(87) PCT Pub. No.: WO2018/148606

PCT Pub. Date: Aug. 16, 2018

(65) Prior Publication Data

US 2020/0103401 A1    Apr. 2, 2020

Related U.S. Application Data

(60) Provisional application No. 62/460,069, filed on Feb. 16, 2017, provisional application No. 62/459,602,
(Continued)

(51) Int. Cl.
*G01N 33/543* (2006.01)
*B01L 3/00* (2006.01)
(Continued)

(52) U.S. Cl.
CPC .............. *G01N 33/54366* (2013.01); *B01L 3/502738* (2013.01); *B01L 3/5088* (2013.01);
(Continued)

(58) Field of Classification Search
CPC ............ G01N 33/54366; G01N 1/312; G01N 33/492; G01N 1/405; G01N 21/65; G01N 21/76; G01N 33/49; G01N 33/54313; G01N 33/54386; G01N 33/54393; G01N 33/543; B01L 3/502738; B01L 3/5088;
(Continued)

(56) References Cited

U.S. PATENT DOCUMENTS

| 4,022,521 A | 5/1977 | Hall et al. |
| 4,889,816 A | 12/1989 | Davis et al. |

(Continued)

FOREIGN PATENT DOCUMENTS

| EP | 0961110 A2 | 12/1999 |
| JP | 2006071475 A | 3/2006 |

(Continued)

*Primary Examiner* — Christopher L Chin
*Assistant Examiner* — Ellis Lusi

(57) ABSTRACT

The present invention provides QMAX based devices, kits, and methods for rapid, easy to use, and/or inexpensive detection of assaying.

104 Claims, 24 Drawing Sheets

Related U.S. Application Data filed on Feb. 15, 2017, provisional application No. 62/459,160, filed on Feb. 15, 2017, provisional application No. 62/457,103, filed on Feb. 9, 2017, provisional application No. 62/457,031, filed on Feb. 9, 2017, provisional application No. 62/457,133, filed on Feb. 9, 2017.

(51) Int. Cl.
- *G01N 1/31* (2006.01)
- *G01N 33/49* (2006.01)

(52) U.S. Cl.
CPC ........... *G01N 1/312* (2013.01); *G01N 33/492* (2013.01); *B01L 2200/025* (2013.01); *B01L 2200/12* (2013.01); *B01L 2300/04* (2013.01); *B01L 2300/0609* (2013.01)

(58) Field of Classification Search
CPC ........... B01L 2200/025; B01L 2200/12; B01L 2300/04; B01L 2300/0609; C12Q 1/6804; C12Q 1/6869; C12Q 1/6837; C12Q 2537/125; C12Q 2537/1373; C12Q 2537/161; C12Q 2563/149; C12Q 2565/601; G06K 9/00134; G06K 9/00147
USPC ............... 436/518, 807, 805; 356/244, 246; 422/401, 408, 425, 436, 551, 561, 563; 435/288.3, 288.7, 40.5, 40.52, 165
See application file for complete search history.

(56) References Cited

U.S. PATENT DOCUMENTS

| | | | |
|---|---|---|---|
| 6,045,753 | A | 4/2000 | Loewy et al. |
| 6,180,314 | B1 | 1/2001 | Berndt |
| 6,358,475 | B1 | 3/2002 | Berndt |
| 6,714,287 | B2 | 3/2004 | Berndt |
| 9,084,995 | B2 | 7/2015 | Wardlaw |
| 10,890,581 | B2 * | 1/2021 | Stoner ............... G01N 33/5436 |
| 2002/0126271 | A1 | 9/2002 | Berndt |
| 2006/0246508 | A1 * | 11/2006 | Watanabe ............. C12M 23/12 435/7.1 |
| 2007/0105185 | A1 * | 5/2007 | Cima .................... B01L 3/5088 435/297.5 |
| 2008/0318269 | A1 * | 12/2008 | Olson ...................... C12Q 1/18 435/39 |
| 2009/0211344 | A1 | 8/2009 | Wang |
| 2009/0305397 | A1 * | 12/2009 | Dodgson ............... B01L 3/5085 435/305.3 |
| 2011/0256573 | A1 | 10/2011 | Davis et al. |
| 2015/0005203 | A1 * | 1/2015 | Chiou ................... C12Q 1/686 506/33 |
| 2017/0014821 | A1 * | 1/2017 | Carrera Fabra .. G01N 33/54366 |

FOREIGN PATENT DOCUMENTS

| | | | | |
|---|---|---|---|---|
| JP | 2012083190 | A | | 4/2012 |
| JP | 2015121421 | A | | 7/2015 |
| WO | 2005100539 | A2 | | 10/2005 |
| WO | 2009117652 | A1 | | 9/2009 |
| WO | 2015/179848 | | * | 5/2015 |
| WO | WO-2015179848 | A1 * | 11/2015 | ........... C12Q 1/6834 |
| WO | 2017048871 | A1 | | 3/2017 |

\* cited by examiner

Sodium Rhodizonate      Lead Rhodizonate   
Dark Yellow Color                           Red-Crimson Color

QMAX ASSAY AND APPLICATIONS (II)

CROSS-REFERENCE TO RELATED APPLICATIONS

This application is a § 371 national stage application of International Application PCT/US2018/017712 filed on Feb. 9, 2018, which claims the benefit of priority to U.S. provisional application No. 62/457,133, filed on Feb. 9, 2017, to U.S. provisional application No. 62/457,031, filed on Feb. 9, 2017, U.S. provisional application No. 62/457,103, filed on Feb. 9, 2017, U.S. provisional application No. 62/459,160, filed on Feb. 15, 2017, U.S. provisional application No. 62/459,602, filed on Feb. 15, 2017, and U.S. provisional application No. 62/460,069, filed on Feb. 16, 2017, the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays.

BACKGROUND

In biological and chemical assays (e.g. diagnostic testing), often it needs to measure the volume, change the shape, and/or detect analytes of a sample or a part of the sample, quickly and simply. The current invention provides devices and methods for achieving these goals. In biological and chemical assays (e.g. diagnostic testing), often it needs to measure the volume, change the shape, and/or detect analytes of a sample or a part of the sample, quickly and simply. The current invention provides devices and methods for achieving these goals. In biological and chemical assays (e.g. diagnostic testing), often it needs to measure the volume, change the shape, and/or detect analytes of a sample or a part of the sample, quickly and simply. The current invention provides devices and methods for achieving these goals. Pathogenic diseases, such as sexually transmitted diseases (STDs), pose significant risks to people's health and quality of life. Early detection and diagnosis of pathogenic diseases would substantially improve the likelihood of recovery and prevent further dissemination of the diseases. In some cases, it is desirable to provide rapid and easy to access testing devices and methods for detecting the pathogenic diseases. In addition, it may be convenient if non-professionals, such as a person who is suspected to have the disease, can administer the tests to expedite the process, avoid embarrassment, and improve the willingness to be tested. Sometimes the preliminary test results acquired through a rapid and convenient test may be further confirmed or overturned by slower but more precise tests administered by medical professionals. In some cases, lowering the cost of the test may also improve the ubiquities of the test and relieve pressure on the public health system.

The present invention provides kits, devices and methods for rapid, easy to use, and/or inexpensive detection of pathogenic diseases, such as but not limited to sexually transmitted diseases (STDs). Among other things, the present invention is related to devices and methods of performing assays, that uses surface patterns. The surface patterns are used for guiding an open flow of a sample, filtering certain components of the sample, improving a measurement accuracy, or a combination of thereof.

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

A. Assay Improvement (I)

"Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

Figure 1:
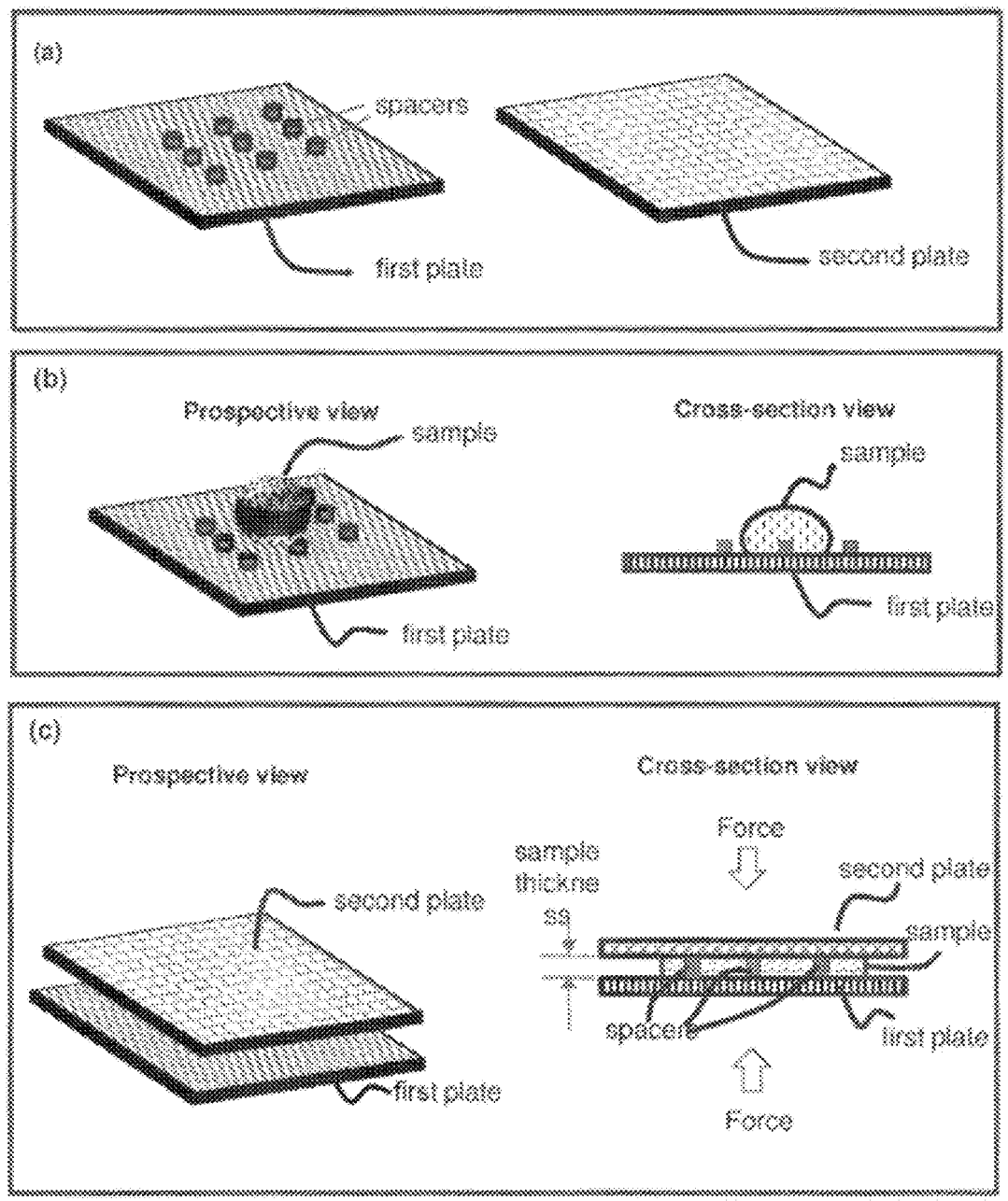
FIG. 1 illustrates a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).

One embodiment of the method of CROF, as illustrated in FIG. 1, comprises:

(a) obtaining a sample, that is flowable;

(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;

(c) depositing, when the plates are configured in an open configuration, the sample on one or both of the plates; wherein the open configuration is a configuration in which the two plates are either partially or completely separated apart and the spacing between the plates is not regulated by the spacers; and (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average.).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

A. Quantitative Assay Using QMAX Device

One aspect of the present invention provides devices and methods for quantitative assays using QMAX device.

In some embodiments, one or both of the plates comprise a binding site that contains capture agents capable of immobilizing analyte in the sample, said one or both of the plates further comprise target binding partners of different concentrations at different locations of the binding site that are immobilized by the capture agents, and competitively block the binding between the capture agents and the analyte in the sample.

In some embodiments, one or both of the plates comprise a binding site that contains capture agents capable of immobilizing analyte in the sample, said one or both of the plates further comprise binding partners (not target binding partner) of different concentrations at different locations of the binding site that are immobilized by the capture agents, and competitively block the binding between the capture agents and the analyte in the sample.

In some embodiments, one or both of the plate comprises multiple binding sites that contain captured agents of different concentrations.

In some embodiments, the capture agents are antibodies, and the target binding partner are the target antigen of the capture antibodies, which competitively blocks the binding between the capture antibodies and the antigen analyte in the sample.

In some embodiments, the devices and methods provided herein are particularly useful for quantitatively detecting and measuring the target analyte in the bio/chemical sample.

AA1. A device for quantitative assay, comprising:
a first plate, a second plate, and spacers, wherein:
   i. the plates are movable relative to each other into different configurations;
   ii. one or both plates are flexible;
   iii. each of the plates comprises, on its respective inner surface, a sample contact areas for contacting a sample suspected of containing a target analyte;
   iv. one or both of the plates comprise the spacers that are fixed to the respective plate;
   v. the spacers have a predetermined substantially uniform height and a predetermined substantially uniform height;
   vi. at least one of the spacers is inside the sample contact area; and
   vii. the first plate comprises a plurality of binding sites in the sample contact area, wherein each of the binding sites comprises capture agents of predetermined concentrations capable of binding and immobilizing the target analyte, wherein the concentrations of the capture agents in at least two of the binding sites are different from one another;
   wherein one of the configurations is an open configuration, in which: the two plates are partially or entirely separated apart, the spacing between the plates is not regulated by the spacers, and the sample is deposited on one or both of the plates; and
   wherein another of the configurations is a closed configuration, which is configured after the sample deposition in the open configuration, and in the closed configuration: at least part of the sample is compressed by the two plates into a layer of uniform thickness, wherein the uniform thickness of the layer is confined by the inner surfaces of the two plates and is regulated by the plates and the spacers.

AB1. A method of quantitative assay, comprising the steps of:
(a) obtaining a sample;
(b) obtaining a first plate, a second plate, and spacers; wherein:
   i. the plates are movable relative to each other into different configurations;
   ii. one or both plates are flexible;
   iii. each of the plates comprises, on its respective inner surface, a sample contact areas for contacting a sample suspected of containing a target analyte;
   iv. one or both of the plates comprise the spacers that are fixed to the respective plate;
   v. the spacers have a predetermined substantially uniform height and a predetermined substantially uniform height;
   vi. at least one of the spacers is inside the sample contact area; and
   vii. the first plate comprises a plurality of binding sites in the sample contact area, wherein each of the binding sites comprises capture agents of predetermined concentrations capable of binding and immobilizing the target analyte, wherein the concentrations of the capture agents in at least two of the binding sites are different from one another;
(c) depositing the sample on one or both of the plates when the plates are in an open configuration,
   wherein in the open configuration the two plates are partially or entirely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
   bringing the two plates together; and
   conformably pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers;
(e) measuring signal related to the analyte captured by the capture agent are the signals coming from (i) the analyte captured by the capture agent, (ii) a label attached to an analyte that is captured by the binding site, or (iii) both (i) and (ii); and
(f) comparing signal from the two binding sites with capture agents of different concentrations and determining concentration of the target analytes in the sample based on the comparison.
   wherein a conformable pressing is a method that makes the pressure applied over an area is substantially constant regardless the shape variation of the outer surfaces of the plates; and
   wherein the parallel pressing applies the pressures on the intended area at the same time, and a sequential pressing applies the pressure on a part of the intended area and gradually move to other area.

Figure 30:
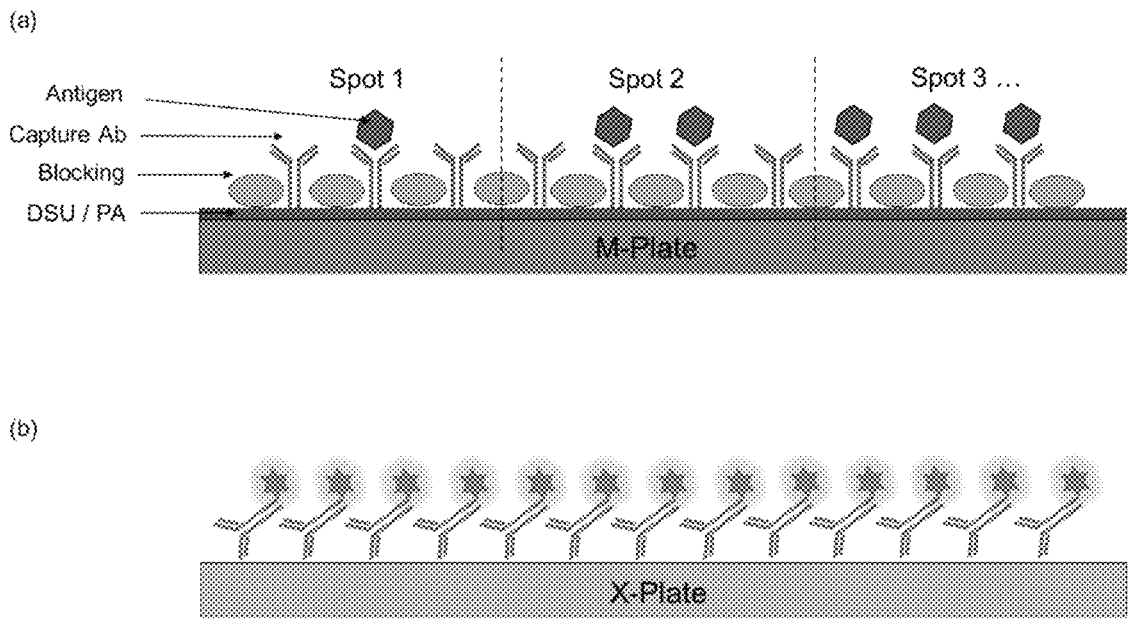
FIG. 30 (a) shows the schematic of preparation of first plate as the binding plate or capture plate. (b) shows the schematic of preparation of second plate as the storage plate.
Figure 31:
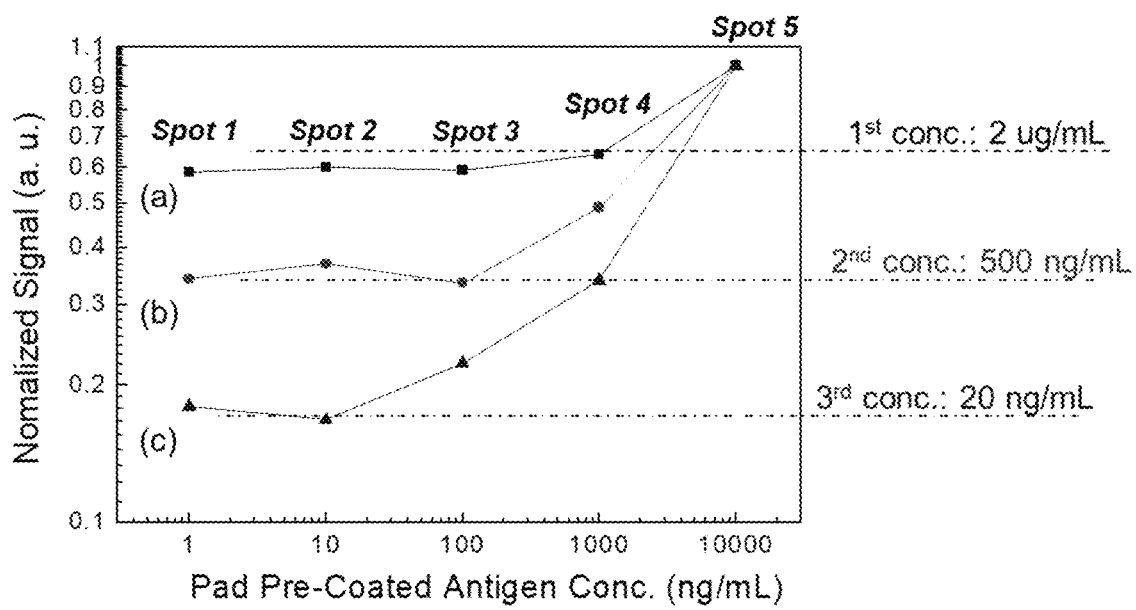
FIG. 31 shows the fluorescence signal of 5 spots (pre-coated concentrations of 10 ug/mL, 1 ug/mL, 100 ng/mL, 10 ng/mL, 1 ng/mL human IgG antigen) when testing the human IgG sample with concentration of (a) 2 ug/mL, (b) 500 ng/mL, and (c) 20 ng/mL.

FIG. 30 and FIG. 31 are exemplary embodiments of the present invention, in which quantitative assays using QMAX device and method were tested experimentally. FIG. 30 (a) shows the schematic of preparation of first plate as the binding plate or capture plate. The M-Plate fabricated on 500 um thick glass is a periodic nonmetallic pillar array with a period 200 nm, pillar height 55 nm and pillar diameter 80 nm, a gold disk on top of each pillar with a thickness 50 nm and diameter 100 nm, a gold backplane on the foot of the pillars, gold nanodots with 10 nm diameter randomly located on the pillar walls, and nanogaps between these metal components. M-Plate with a size of 1inch by 1inch was first incubated in DSU 1 mM in Dioxin overnight, then washed with dioxin. After coating the self-assemble layer (DSU), M-Plate was put in a container with 10 ug/mL protein-A in PBS for 2 hours, followed by washing 3 times with PBST. M-Plate was then coated with Capture Ab (goat anti-human IgG) 10 ug/mL in PBS for 2 hours, followed by washing 3 times with PBST. M-Plate was blocked with 2% BSA in PBS for 2 hours, followed by washing 3 times with PBST. At last step, six 0.4 uL droplets of human IgG (target antigen) with concentrations of 10 ug/mL, 1 ug/mL, 100 ng/mL, 10 ng/mL, 1 ng/mL, 0 are incubated with QMAX (30 um spaing) on six different spots on the chip for 1 min, followed by washing 3 times with PBST, and 3 times with water and dry at 37° C. in air for 1 hour. (b) shows the schematic of preparation of second plate as the storage plate. X-Plate is a micro-pillar array with 30×40 um pillar size, 80 um inter spacing distance and 30 um pillar height, made on 175 um thick PMMA film. Detection Ab (mouse anti-human IgG) conjugated Cy-5 10 ug/mL 200 uL uniformly printed and dried on X-Plate (25 mm×25 mm area) at 37° C. for 2 hours. FIG. 31 shows the fluorescence signal of 5 spots (pre-coated concentrations of 10 ug/mL, 1 ug/mL, 100 ng/mL, 10 ng/mL, 1 ng/mL human IgG antigen) when testing the human IgG sample with concentration of (a) 2 ug/mL, (b) 500 ng/mL, and (c) 20 ng/mL. From the results, when testing the sample concentration of 2 ug/mL, the curve bend at the spot 4 (pre-coat 1 ug/mL); when testing the sample concentration of 500 ng/mL, the curve bend at the spot 3 (pre-coat 100 ng/mL); when testing the sample concentration of 2 ug/mL, the curve bend at the spot 2 (pre-coat 10 ng/mL). Estimated from the bending position, the sample concentration range can be known.

C. QMAX Device for Counting White Blood Cells

Figure 32:
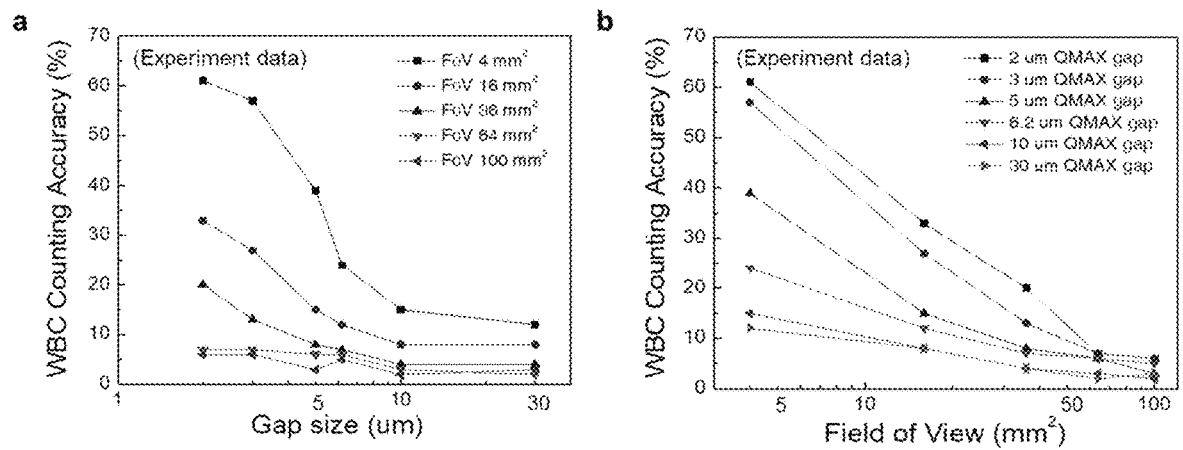
FIG. 32 shows WBC counting accuracy vs. FoV vs. QMAX gap. (a) Plots of WBC counting accuracy vs. QMAX gap size with effective field of view (FoV) of 4 mm$^2$, 16 mm$^2$, 36 mm$^2$, 64 mm$^2$, 100 mm$^2$; (b) Plots of WBC counting accuracy vs. field of view (FoV) with QMAX gap size of 2 um, 3 um, 5 um, 6.2 um, 10 um and 30 um.
Figure 33:
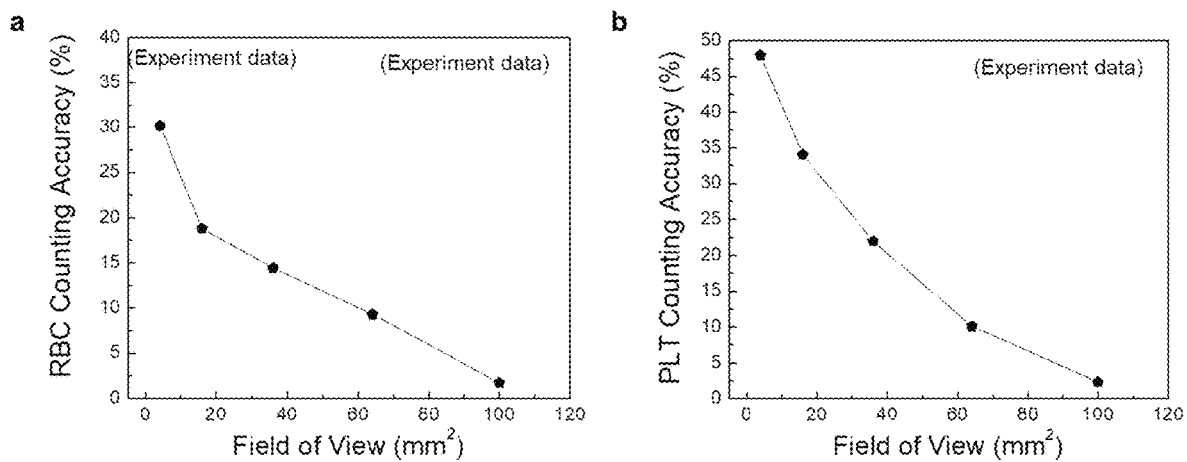
FIG. 33 (a) plots of RBC counting accuracy vs. field of view (FoV) with QMAX gap size of 2 um. (b) Plots of PLT counting accuracy vs. field of view (FoV) with QMAX gap size of 2 um.

Another aspect of the present invention provides devices and method for counting white blood cells (WBC) using QMAX device and system, FIG. 32 and FIG. 33 are exemplary embodiments of the present invention, showing experimental parameters and results for WBC counting using QMAX device and system.

For WBC blood counting,

The gap size of QMAX is in the range of 2 um, 5 um, 10 um, 30 um or a range between any two of the values;

The preferred field of view is 0.1 mm$^2$, 10 mm$^2$, 50 mm$^2$, 100 mm$^2$ or a range between any two of the values;

With field of view of 0.1 mm2 to 10 mm$^2$, preferred gap size of QMAX is in the range of 10 um to 30 um; (with counting accuracy less than 10%)

With field of view of 10 mm$^2$ to 50 mm$^2$, preferred gap size of QMAX is in the range of 5 um to 10 um, 10 um to 30 um; (with counting accuracy less than 10%)

With field of view of 50 mm$^2$ to 100 mm$^2$, preferred gap size of QMAX is in the range of 2 um to 5 um, 5 um to 10 um, 10 um to 30 um; (with counting accuracy less than 10%)

For RBC blood counting,

The preferred gap size of QMAX is in the range of 1.5 um, 1.8 um, 1.8 um, 2.2 um, 2.5 um or a range between any two of the values;

The preferred field of view is 0.1 mm$^2$, 0.5 mm$^2$, 10 mm2, 50 mm2, 100 mm$^2$, 400 mm$^2$ or a range between any two of the values;

To achieve the RBC counting accuracy less than 10%, preferred FoV is 50 mm$^2$ to 100 mm$^2$, 100 mm$^2$ to 400 mm$^2$ To achieve the RBC counting accuracy less than 5%, preferred FoV is 100 mm$^2$ to 400 mm$^2$ For PLT blood counting, The preferred gap size of QMAX is in the range of 0.5 um, 1.0 um, 2.0 um, 3.0 um or a range between any two of the values;

The preferred field of view is 0.1 mm$^2$, 10 mm$^2$, 50 mm$^2$, 100 mm$^2$ or a range between any two of the values;

To achieve the PLT counting accuracy less than 10%, preferred FoV is 50 mm$^2$ to 100 mm$^2$, 100 mm$^2$ to 400 mm$^2$ To achieve the PLT counting accuracy less than 5%, preferred FoV is 100 mm$^2$ to 400 mm$^2$.

For WBC blood counting:

Preferred gap size of QMAX is 2 um, 5 um and 10 um;

Preferred field of view is in the range of 10 mm$^2$ to 50 mm$^2$;

For RBC blood counting:

Preferred gap size of QMAX is 2 um;

Preferred field of view is in the range of 0.5 mm$^2$ to 1 mm$^2$, 1 mm$^2$ to 10 mm$^2$;

For PLT blood counting:

Preferred gap size of QMAX is 0.5 um, 1 um and 2 um;

Preferred field of view is in the range of 0.5 mm$^2$ to 1 mm$^2$, 1 mm$^2$ to 10 mm$^2$;

D. QMAX Device with Controlled Release

D.1 QMAX Device with Slow Release

One aspect of the present invention is to provide a QMAX device with slow release mechanism capable of being used for two-step affinity binding assays, in which both binding agent and detection agent are used for assaying target analyte in the sample, and the detection agent is slowly released into the sample after the substantial binding of the target analyte by the binding agent.

Figure 2:
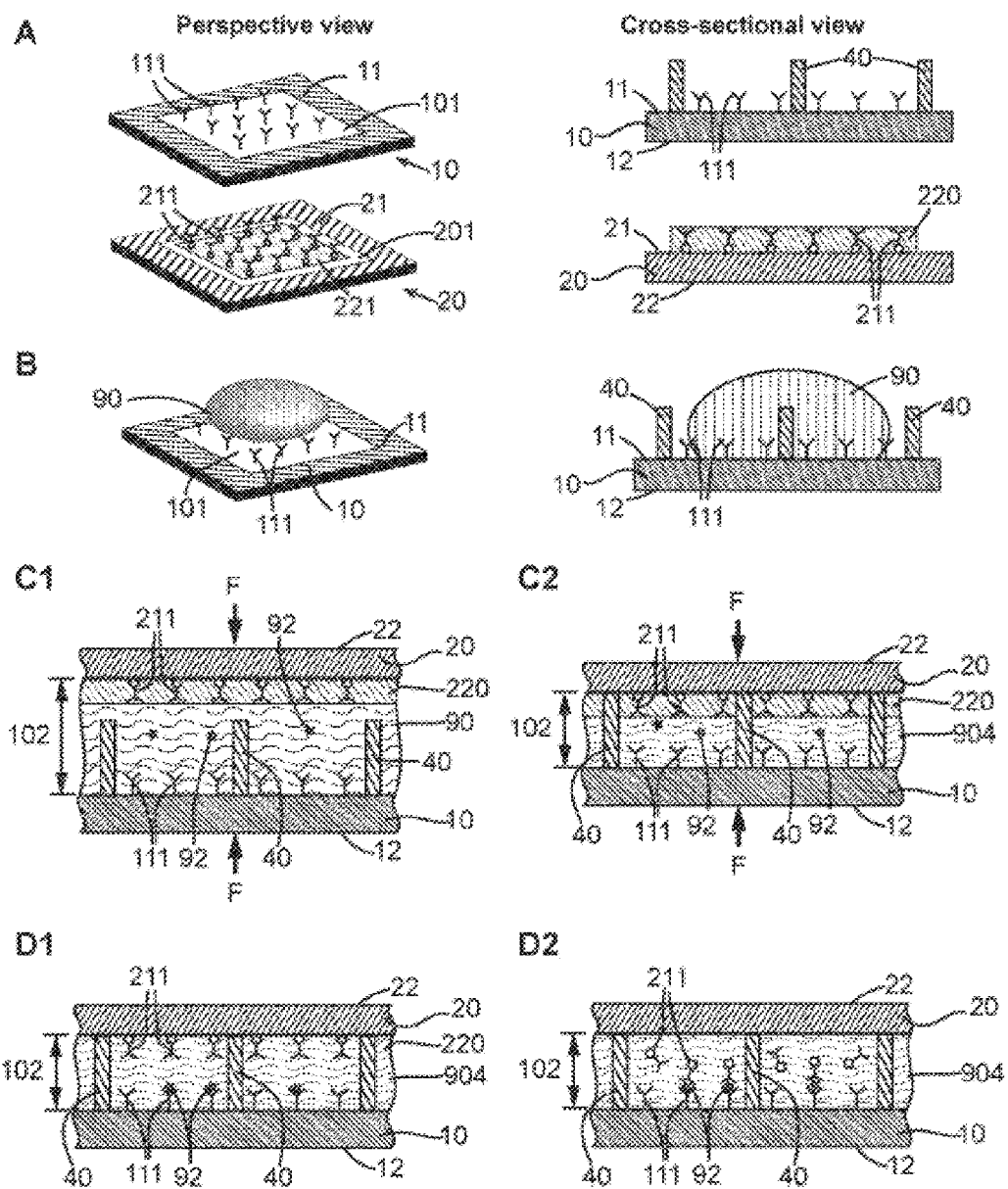
FIG. 2 illustrates an embodiment of a QMAX device that comprises a slow release agent coated on top of the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panels (D1) and (D2) show the delayed release of the detection agent until the binding of the target analyte by the binding agent and the consequential binding of the target analyte by the detection agent in the thin layer. The delayed release is controlled by the slow release material.

FIG. 2 schematically shows exemplary embodiments of the QMAX device, which comprises a first plate 10 and a second plate 20. In particular, panel (A) shows a perspective view of the two plates. Each of the first plate 10 and the second plate 20 comprises an inner surface (11 and 21 respectively). On the inner surface 11, the first plate 10 comprises a binding site 101 (not shown in the cross-sectional view), on which binding agent 111 is coated and immobilized. It should be note, however, in some embodiments, the binding agent 111 is not immobilized on the first plate inner surface 11 but also releasable upon contacting the sample. Furthermore, the first plate 10 comprises spacers 40 (not shown in the perspective view) that are fixed to its inner surface 11. At least of the spacers 40 is inside the binding site 101. It should be noted, however, in other embodiments, the second plate 20 or both the first plate 10 and the second plate 20 have the spacers 40 fixed to the respective inner surfaces. In some embodiments, the spacers (42 and 42) are permanently fixed to one or both of the plates 10 and 20. Herein the term "permanently fixed" means that the spacers are attached to a plate and the attachment is maintained during one or more uses of the plate. The second plate 20 comprises, on its inner surface 21, a storage site 201 (not shown in the cross-sectional view), on which detection agent 211 is coated together with slow release agent 220. The slow release agent 220 is coated on top of the detection agent 211. It is also possible that the slow release agent 220 is mixed with the detection agent 211.

The first plate 10 and second plate 20 are movable relative to each other into different configurations, including an open configuration and a closed configuration. FIG. 2 panels (A) and (B) depict some embodiments of the open configuration. In the open configuration, the two plates are partially or entirely separated apart, and the spacing between the plates is not regulated by the spacers 40. As shown in panel (B), the spacing between the plates in the open configuration allows a liquid sample 90 to be deposited on the first plate 10. It is to be noted, however, is other embodiments, the sample 90 is deposited either on the second plate 20 or on both plates 10 and 20.

FIG. 2 panels (C1)-(D2) illustrate the detailed exemplary process of utilizing the QMAX device to perform a non-competitive assay. More specifically, panels (C1) and (C2) depict the initial process of bringing the two plates from the open configuration to the closed configuration. As shown in panel (C1), after the deposition of the sample 90, the two plates are brought to face each other with their inner surfaces. A compressing force F is applied on the two plates to reduce the spacing between them. Panel (C2) shows that the two plates are brought into the closed configuration by the compressing force F. In the closed configuration, the spacing 102 between the first plate 10 and the second plate 20 is regulated by the spacers 40. Consequently, at least part of the sample 90 is compressed into a thin layer 904 and the thickness of the thin layer 904 is regulated by the spacers 40. The thin layer 904 is in touch with both the binding site 101 and the storage site 201.

FIG. 2 panels (D1) and (D2) illustrate the detailed two-step process of the assay while the plates are at the closed configuration, in which: (1) the target analyte 92 contained in the thin layer 904 binds to and is captured by the binding agent 111 that is immobilized on the first plate inner surface 11, as shown in panel (D1), and (2) the detection agent 211 is released from the second plate 20 and dissolved and diffuses in the sample, and consequently binds to the target analyte 92 that is captured by the binding site, forming a binding agent-target analyte-detection agent sandwich-like structure in panel (D2).

It is to be noted that, as shown in FIG. 2 panels (C1) and (C2), during the assay, in order to realize the two-step process, the detection agent 211 is retained by the slow release agent on the second plate inner surface 21 and not released therefrom until the target analyte 92 substantially binds to and is captured by the binding agent 111, as shown in panel (D1). Therefore, in other words, the slow release agent 220 is configured to render the substantial release of the detection agent after the target analyte in the sample is substantially captured by the binding agent. As shown in panel (D2), the slow release agent 220 releases the detection agent 211 from the plate through its own substantial dissolution in the sample (the dissolved slow release agent 220 is shown), which does not occur until the target analyte 92 binds to the binding agent 111. The term "release time" as used herein refers to the time it takes for the detection agent to be substantially released and dissolved in the sample after the binding site contacts the sample. The term "substantial" or "substantially" as used herein refers to a volume percentage of the object or a completion percentage of the process that is equal to or larger than 50%, 60%, 70%, 80%, 90%, 95%, 99%, 100%, or any value between any two of these values.

In some embodiments, the QMAX device is also capable of being used for a competitive assay, where the binding agent is configured to bind and capture the target analyte, which competitively inhibits the binding of the detection agent to the binding agent. In these embodiments, the slow release agent is also configured to render the release time of the detection agent equal to or longer than the time it takes for the target analyte to be substantially captured by the binding agent.

Another aspect of the present invention is to provide a QMAX device capable of being used for a one-step assay, where only detection agent is used for assaying the target analyte without capture of the target analyte by the binding agent. For assays of this type, it is desirable that the detection agent is not substantially released into the sample until the sample is compressed into a thin layer. This is because if the detection agent is readily released and dissolved into the sample upon or very briefly after contacting the sample, then the dissolved detection agent will more than likely to be forced to flow in the direction of the sample flow during the process of the plates being brought from the open configuration to the closed configuration. In many cases, the forced flow of the detection agent will result in an undesirable, largely unequal distribution of the detection agent in the sample, partially due to its limited diffusion across the lateral dimension of the plate within a short period of time. For instance, in a colorimetric staining assay, a colorful ring of the dye may form, of which the center manifests faint to none of the indicative color and is at the point the compressing force being applied, and the ring body manifests the indicative color of much higher intensity.

Figure 3:
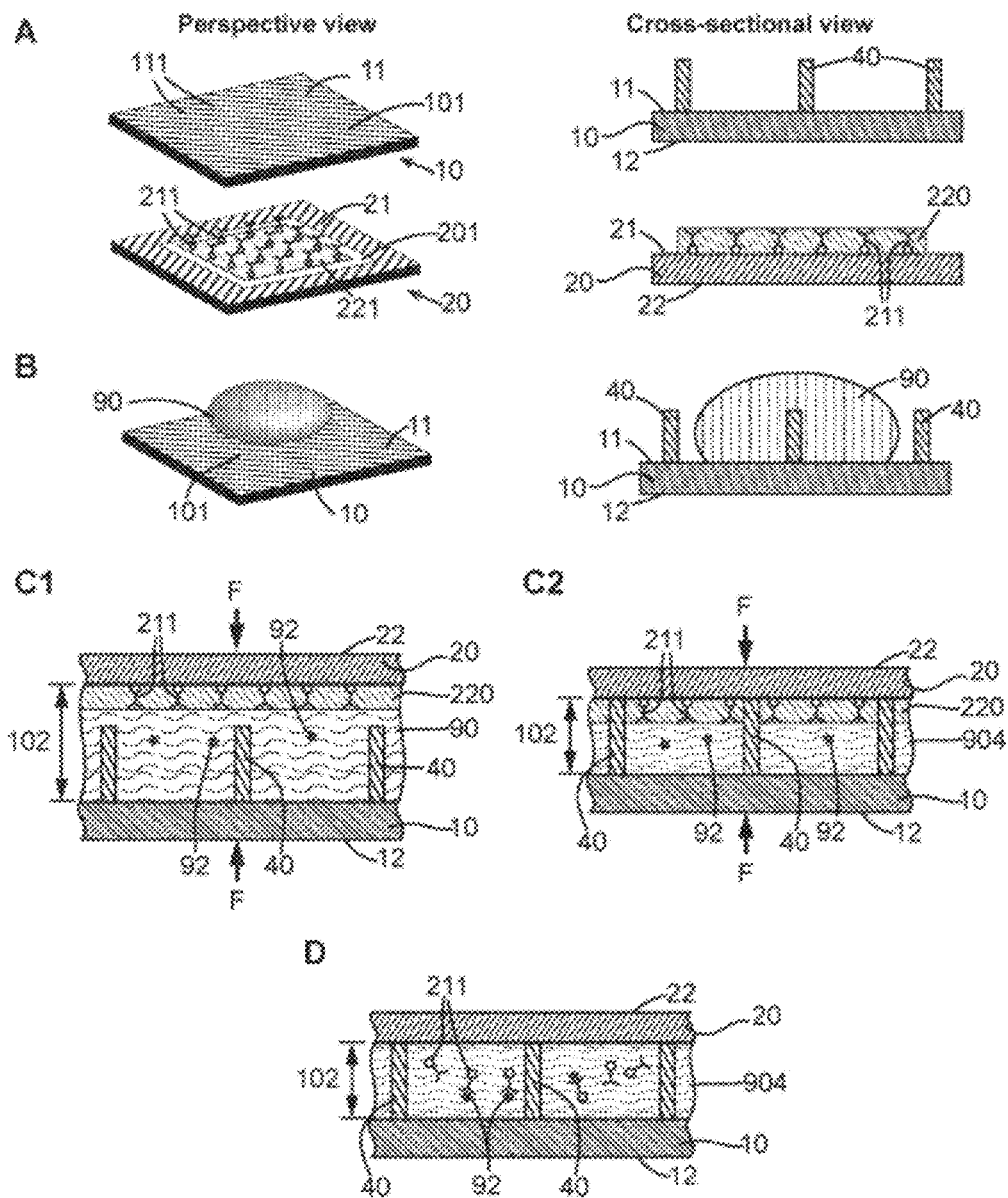
FIG. 3 illustrates an embodiment of a QMAX device that comprises a slow release agent that is coated on top of the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panel (D) show the delayed release of the detection agent until the formation of the thin layer and the consequential binding of the target analyte by the detection agent in the thin layer. The delayed release is controlled by the slow release material.

FIG. 3 illustrates some exemplary embodiments of the QMAX device for realizing the homogenous distribution of the detection agent. More specifically, as shown in the figure, the QMAX device comprises a first plate 10 and a second plate 20. Each of the plates comprises an inner surface, 11 and 21 respectively. One or both of the plates comprise spacers 40 that are fixed to the respective inner surface (only the first plate 10 is shown to have the spacers 40 here in the cross-sectional views in FIG. 3). The second plate 20 comprises, on its inner surface 21, a storage site 201 (not shown in cross-sectional views), on which the detection agent 211 is coated together with the slow release agent 220. The slow release agent 220 is coated on top of the detection agent 211. Similar as shown in FIG. 2, the two plates in FIG. 3 are also movable relatively to each other into different configurations, including an open configuration and a closed configuration. FIG. 3 panels (A) and (B) panels (A) and (B) depict some embodiments of the open configuration. In the open configuration, the two plates are partially or entirely separated apart, and the spacing between the plates is not regulated by the spacers 40. As shown in panel (B), the spacing between the plates in the open configuration allows a liquid sample 90 to be deposited on the first plate 10. It is to be noted, however, in other embodiments, the sample 90 is deposited either on the second plate 20 or on both plates 10 and 20.

FIG. 3 panels (C1)-(D) illustrate the detailed exemplary process of utilizing the QMAX device to perform a one-step assay. More specifically, panels (C1) and (C2) depict the initial process of bringing the two plates from the open configuration to the closed configuration. As shown in panel (C1), after the deposition of the sample 90, the two plates are brought to face each other with their inner surfaces. A compressing force F is applied on the two plates to reduce the spacing between them. Panel (C2) shows that the two plates are brought into the closed configuration by the compressing force F. In the closed configuration, the spacing 102 between the first plate 10 and the second plate 20 is regulated by the spacers 40. Consequently, at least part of the sample 90 is compressed into a thin layer 904 and the thickness of the thin layer 904 is regulated by the spacers 40. The thin layer 904 is in touch with the storage site 201.

It is to be noted that the slow release agent 220 retains the detection agent until the formation of the thin layer 904, as shown in FIG. 3 panel (C2), after which the detection agent 211 is substantially released into the thin layer 904 and specifically binds to the target analyte 92. In other words, in these embodiments, the slow release agent is configured to render the substantial release of the detection agent after the two plates are compressed into the closed configuration. Therefore, the detection agent is only substantially released after the plates enter the closed configuration, in which the thin layer of sample has formed.

As discussed above, in some embodiments, the time period that the release of the reagent is delayed by is about equal to or longer than the time that it takes for the target analyte to be substantially captured by the binding agent. In some other embodiments, the time period that the release of the reagent is delayed by is about equal to or longer than the time that it takes for the plates to transition from the open configuration to the closed configuration. In some embodiments, the delayed time period is 1 sec or longer, 2 sec or longer, 3 sec or longer, 5 sec or longer, 8 sec or longer, 10 sec or longer, 15 sec or longer, 20 sec or longer, 30 sec or longer, 45 sec or longer, 60 sec or longer, 2 min or longer, 3 min or longer, 5 min or longer, 10 min or longer, 20 min or longer, 30 min or longer, 45 min or longer, 60 min or longer, 2 hour or longer, 5 hour or longer, 10 hour or longer, or within any range between any two of the values.

D.2 QMAX Device with Stimulus-Dependent Release

Figure 4:
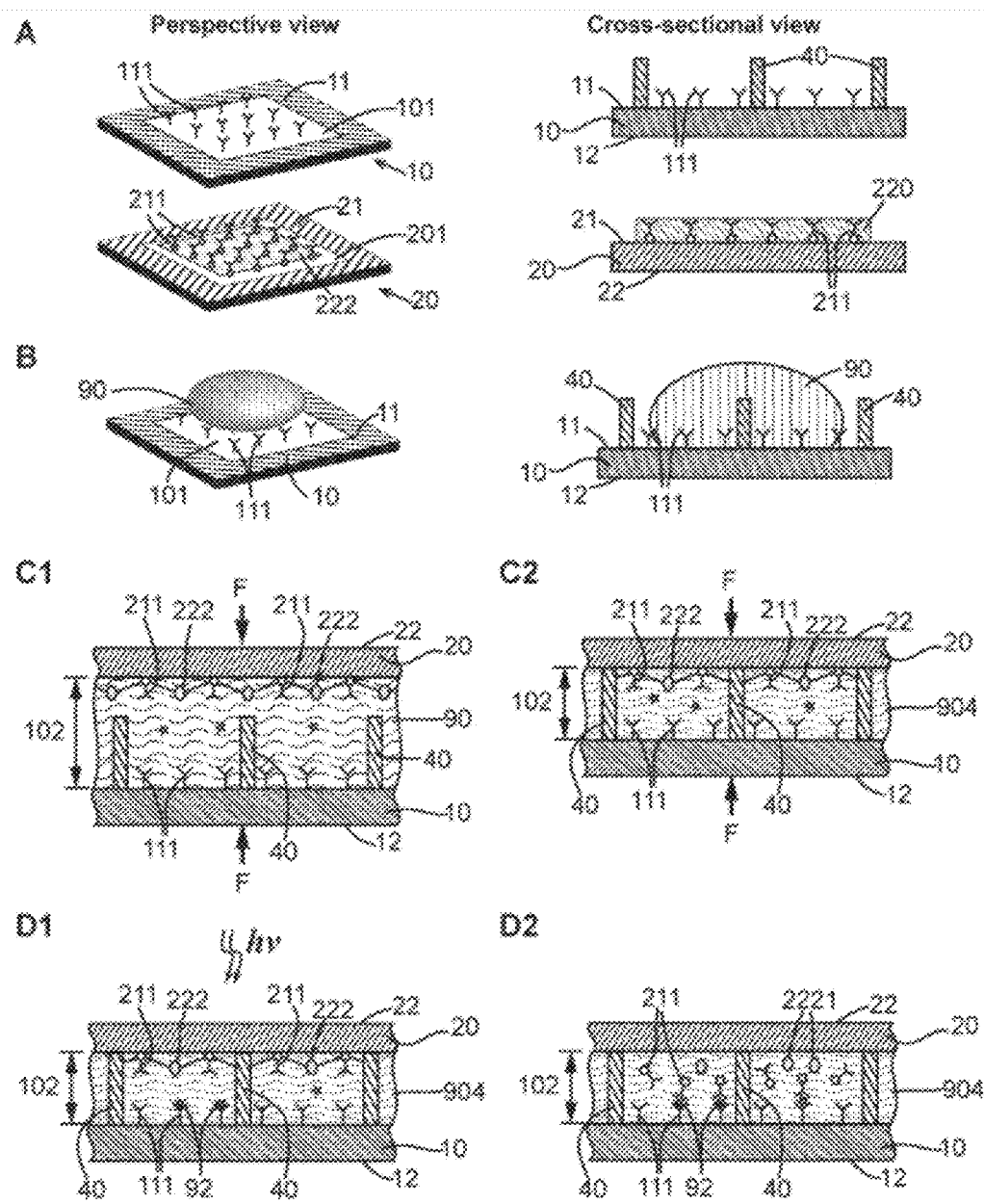
FIG. 4 illustrates an embodiment of a QMAX device that comprises a stimulus-sensitive release agent that is mixed with the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panels (D1) and (D2) show the controlled release of the detection agent and the consequential binding of the target analyte by the detection agent in the thin layer. The release of the detection agent is controlled by the delivery of a laser beam on the stimulus-sensitive release agent.

Referring now to FIG. 4, some other exemplary embodiments of the QMAX device are schematically illustrated. As shown, the QMAX device comprises a first plate 10 and a second plate 20. Each of the first plate 10 and the second plate 20 comprises an inner surface (11 and 21 respectively). On the inner surface 11, the first plate 10 comprises a binding site 101 (not shown in the cross-sectional view), on which binding agent 111 is coated and immobilized. It should be note, however, in some embodiments, the binding agent 111 is not immobilized on the first plate inner surface 11 but also releasable upon contacting the sample. Furthermore, the first plate 10 comprises spacers 40 (not shown in the perspective view) that are fixed to its inner surface 11. At least of the spacers 40 is inside the binding site 101. It should be noted, however, in other embodiments, it is possible that the second plate 20 or both the first plate 10 and the second plate 20 have the spacers 40 fixed to the respective inner surfaces. The second plate 20 comprises, on its inner surface 21, a storage site 201 (not shown in the cross-sectional view) that contains a detection agent 211 and a stimulus-sensitive release agent 222. The stimulus-sensitive release agent 222 is mixed with the detection agent 211 and the two are cross-linked with each other (the cross-link symbolized by the straight lines between the detection agent 211 and the stimulus-sensitive release agent 222). It is also possible that the stimulus-sensitive release agent 222 is coated on top of the detection agent 211.

Similar as shown in FIG. 2, the first plate 10 and second plate 20 in FIG. 4 are also movable relative to each other into different configurations, including an open configuration and a closed configuration. FIG. 4 panels (A) and (B) depict some embodiments of the open configuration. In the open configuration, the two plates are partially or entirely separated apart, and the spacing between the plates is not regulated by the spacers 40. As shown in panel (B), the spacing between the plates in the open configuration allows a liquid sample 90 to be deposited on the first plate 10. It is to be noted, however, in other embodiments, the sample 90 is deposited either on the second plate 20 or on both plates 10 and 20.

FIG. 4 panels (C1)-(D2) illustrate the detailed exemplary process of utilizing the QMAX device to perform a non-competitive assay. More specifically, panels (C1) and (C2) depict the initial process of bringing the two plates from the open configuration to the closed configuration. As shown in panel (C1), after the deposition of the sample 90, the two plates are brought to face each other with their inner surfaces. A compressing force F is applied on the two plates to reduce the spacing between them. Panel (C2) shows that the two plates are brought into the closed configuration by the compressing force F. In the closed configuration, the spacing between the first plate 10 and the second plate 20 is regulated by the spacers 40. Consequently, at least part of the sample 90 is compressed into a thin layer 904 and the thickness of the thin layer 904 is regulated by the spacers 40. The thin layer 904 is in touch with both the binding site 101 and the storage site 201.

In some embodiments of the present invention, the release of the detection agent is stimulus-dependent, that is: in the absence of the stimulus, the stimulus-sensitive release agent retains the detection agent and prevents or blocks its release and dissolution into the sample, whereas, upon receiving the stimulus, the stimulus-sensitive release agent experiences a structural change that leads to the release of the detection agent from the plate and its dissolution into the sample. Therefore, the timing of the release of the detection agent is precisely controlled by the delivery of the stimulus. FIG. 4 panels (C1)-(D2) depict such a precise timing control through the use of the stimulus-sensitive release agent and the delivery of the stimulus. In this exemplary embodiment, the stimulus is a laser beam.

In some embodiments, the stimulus is given in a spatially selective manner, realizing both spatially and temporally controlled release of the detection agent. For instance, when stimulus is a laser beam or other type of electromagnetic wave, it can be projected to a selective area of the stimulus-sensitive release agent on the plate, whereas the detection agent in the other areas of the plate remains unreleased.

Similar as FIG. 2, the assay depicted in FIG. 4 panels (C1)-(D2) also requires at least two steps: (1) the target analyte 92 contained in the thin layer 904 binds to and is captured by the binding agent 111 that is immobilized on the first plate inner surface 11, as shown in panel (D1), and (2) the detection agent 211 is released from the second plate 20 and dissolved and diffuses in the sample, and consequently binds to the target analyte 92 that is captured by the binding site, forming a binding agent-target analyte-detection agent sandwich-like structure in panel (D2). In order to realize the two-step process, initially the detection agent 211, in the absence of the stimulus, is retained by the stimulus-sensitive release agent 222 on the second plate inner surface 21 and not released therefrom. Then, after the moment when the target analyte 92 substantially binds to and is captured by the binding agent 111, as shown in panel (D1), a stimulus is delivered to trigger a change in the structure of the stimulus-sensitive release agent 222 so that the detection agent 211 is released from the plate. As shown in panel (D1), a laser beam (symbolized by hv) is shed upon the stimulus-sensitive release agent 222 as an example of the stimulus. The detection agent 211 is therefore dissolved into the sample, diffuses, and binds to the target analyte 92 that is captured by the binding agent 111.

D.3 Controlled Release Agent

The term "controlled release agent" as used herein refers to a class of material or reagent that can be mixed with or coated on top of the reagents on the plate and used to control the release of the reagents contained on the plate of the QMAX device. The controlled release agents include, but not limited to, the slow release agent and the stimulus-sensitive release agent as described hitherto. The slow release agent and the stimulus-sensitive release agent differ in their mechanism of regulating the release of the detection agent.

As discussed above, the slow release agent autonomously delays the release of the detection agent. In some embodiments of the present invention, the slow release agent is soluble in the sample as described above and the release of the reagent is delayed until the partial or full dissolution of the slow release agent in the sample. The dissolution rate of the slow release agent is so chosen that the release of the reagent into the sample is delayed for a desirable time period. In some embodiments, the slow release agent is mixed with the reagent that is coated on the plate. The term "mixed with" as used herein refers to one type of articles are associated with another type of articles to become one collective mass in the form of physical blending and, optionally, chemical interactions. In some embodiments, the slow release agent is physically mixed with the reagent, and the slow release agent is configured to form a physical trap for retaining the reagent. For instance, the slow release agent can be a polymerized organic compound with mesh-like structure, and the reagent is retained in the holes of the "mesh". The reagent is dissolved after the partial or complete dissolution of the slow release agent, or dissolved at a relatively slower speed in the case where the slow release agent is water-permeable but limits the penetration of water molecules and reagent molecules. In some embodiments, the slow release agent is physically mixed with the reagent and furthermore the two form chemical interactions (bonds) including, but not limited to, covalent bonds, ionic bonds, metallic bonds, hydrogen bonds, and van der Waals bonds. The chemical interactions between the slow release agent and the reagent are also configured to retain the reagent on the plate and delay the release of the reagent until the partial or complete dissolution of the slow release agent.

In some embodiments, the slow release agent is insoluble in the sample and configured to delay the dissolution of the reagent into the sample by a desirable time period. In some embodiments, the slow release agent is coated on top of the reagent on the plate. In this case, the slow release agent is configured to cover the coated reagent on the plate and form a physical barrier, which, at least partially, prevents the reagent from contacting the sample. For instance, the slow release agent is a cross-linked polymer with a lateral area larger than the lateral area of the binding site (or storage site, etc.) where the reagent is coated, and such a cross-linked polymer is coated on the plate and on top of the reagent, covering the majority lateral area of the binding site (or storage site, etc.). In some embodiments, the slow release agent is configured to completely block the contact between the reagent and the sample. For instance, the exemplary cross-linked polymer forms a tight waterproof structure so that no water penetrate the polymer and dissolve the reagent covered under the polymer. In this case, the slow release agent is capable of being dissolved into the sample at a relatively slow speed, so that the reagent is be released and dissolved into the sample until the slow release agent becomes fully or partially dissolved in the sample. In other embodiments, the slow release agent is configured to partially block the contact between the reagent and the sample, limiting the dissolution speed of the reagent that is covered underneath it. For instance, the above-mentioned exemplary cross-linked polymer has porous structure and the pores are water-permeable but small enough so that the penetration of both water molecule and the reagent molecule is limited at a certain level. In this case, the slow release agent is soluble in the sample with a relatively slow dissolution speed, or alternatively, insoluble whatsoever. Such a configuration should contribute the delay of the release of the reagent into the sample, as compared to the release of the reagent in the absence of the slow release agent.

In some embodiments, the slow release agent is made from a group of polymers including, but not limited to, PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

As discussed above, the stimulus-sensitive release agent regulates the release of the detection agent in a stimulus-dependent manner. In some embodiments, the stimulus-sensitive release agent is configured to form cross-links with the detection agent in the absence of the stimulus. The cross-link between the stimulus-sensitive release agent and the detection agent is configured to serve as an intermediate for or strengthen the attachment of the detection agent to the storage site. For instance, the detection agent is not directly attached to the plate, while the stimulus-sensitive release agent exists between the inner surface of the plate and the detection agent and form interactions with both two, thereby bridging the detection agent with the inner surface. Alternatively, the detection agent is attached to the plate itself and the interaction between the stimulus-sensitive release agent and the inner surface as well as the detection agent further tightens the attachment of the detection agent to the plate. Upon the receipt of the stimulus, however, the cross-link between the stimulus-sensitive release agent and the detection agent and optionally the interaction between the stimulus-sensitive release agent and the inner surface are altered to an extent that the attachment of the detection agent to the inner surface is no longer strong enough to retain the detection agent. The detection agent is thereby released from the plate and dissolved in the sample if it exists.

In some embodiments, the stimulus-sensitive release agent forms a polymer autonomously and depolymerizes upon the receipt of the stimulus. The stimulus-sensitive release agent in the polymer state is coated on top of the detection agent or embedded in the detection agent in its polymer structure (therefore "mixed with"), so that the stimulus-sensitive release agent blocks or limits the contact of the detection agent with the liquid sample. Upon the receipt of the stimulus, the stimulus-sensitive release agent depolymerizes to a state that the detection agent is no longer blocked from the contact of the sample and thereby is released and dissolved into the sample.

In some embodiments, the stimulus that triggers the structural changes in the stimulus-sensitive release agent is selected from the group including, but not limited to, electromagnetic wave (radio wave, microwave, infrared radiation, visible light, ultraviolet radiation, X-rays, and gamma rays, etc.), temperature, pH, ion, magnetic stimulus, mechanical stimulus (e.g. mechanical compression, mechanical impact, ultrasound), and electrical stimulus.

In some embodiments, the stimulus is electromagnetic wave, e.g. light, microwave, and the stimulus-sensitive release agent is made from a compound selected from the group including, but not limited to, (E)-(2-Hydroxyphenyl) acrylates, 2-Aroylbenzoates, Xanthenoic esters, 2-Nitrobenzyl derivatives, 1-Alkoxy-9,10-anthraquinones, 2-Oxoacetates, Alkyl phenyl ketones, 4-benzoyl-phenylalanine, amino-coumarin family, Perylene, 1-Acetylperylene, 2-nitrophenyl)propryloxycarbonyl, Ruthenium complex, Chlorophyllin, Phthalocyanin, Distearoyl indocarbocyanine, Azobenzene, 2-diazo-1,2-nathoquinone, Merocyanine/spiropyran, Donor-acceptor stenhouse adducts, and coumarin-modified mesoporous bioactive glass. In some embodiments, the stimulus is temperature stimulus, and the stimulus-sensitive release agent is made from a compound selected from the group including, but not limited to, N-isopropylacrylamide, N, N-dimethylaminoethyl methacrylate (PNIPAm-co-PDMAEMA), Linear PNI-Pam-co-DMAEMA Polymer, PEI-PNIPAm polymer with 46-kDa PNIPAm grafts, Poly[2-(2-ethoxy) ethoxy ethylvinyl ether (EOEOVE), Multiblock copolymers synthesized from pluronic and di-(ethylene glycol) divinyl ether, Polyethylenimine (BPEI)/pDNA complex, Co-polymerization of PVP and acrylic acid, and Pluronic-g-PAA copolymers. In some embodiments, the stimulus is pH, and the stimulus-sensitive release agent is made from a compound selected from the group including, but not limited to, Liposomes attached with a saccharide (lecithin) vector, PEGylated liposome, Copolymer of N-isopropylacryl amide and acryloylpyrrolidine (sterically stabilized liposome), Histidine-modified galactosylated cholesterol derivative—cationic liposome, Anionic liposomes containing phosphatidylethanolamine (PE), Amphiphilic co-polymer of poly (methoxy-polyethylene glycol cyanoacrylate-c0-n-hexadecyl cyano acrylate) (PEG-PH DCA), Polyethylene Poly (phthaloyl-L-lysine), Polyamidoamine dendrimer, Poly (alkylcyanoacrylate) nanoparticles, Poly (methylmethacrylate) Nanoparticles, Poly (alkylcyanoacrylate) Polyester Nanoparticles, Albumin, Chitosan, Dextran, Poly (N-isopropylacrylamidecobutyl-methacrylate-co-acrylic acid), and Poly (N-isopropylacrylamide). In some embodiments, the stimulus is ion (e.g. $Ca^{2+}$, $Mg^{2+}$, $K^+$, $Na^+$), and the stimulus-sensitive release agent is made from a compound selected from the group including, but not limited to, polysaccharides, gelrite, alginate/HPmC, sod alginate/HPC, gelrite gellan gum, and tamarind.

In some embodiments, the stimulus is delivered for 1 sec or longer, 2 sec or longer, 5 sec or longer, 10 sec or longer, 20 sec or longer, 1 min or longer, 2 min or longer, 5 min or longer, 10 min or longer, 20 min or longer, 1 hour or longer, or within any range of any two of these values.

D.4 Methods of Utilizing the QMAX Device for Bio/Chemical Assays

Another aspect of the present invention is to provide a method for utilizing the QMAX device for bio/chemical assays.

In some embodiments, the method is for a two-step affinity binding assay and comprises the steps of:
(a) providing a first plate, a second plate, and spacers, wherein:
  i. the first plate and second plate are movable relative to each other into different configurations, including an open configuration and a closed configuration;
  ii. each of the plates comprises an inner surface for contacting a sample that contains a target analyte;
  iii. the first plate comprises, on its inner surface, a binding site that contains a binding agent capable of binding the target analyte;
  iv. the second plate comprises, on its inner surface, a storage site that contains a detection agent and a controlled release agent that is mixed with or coated on top of the detection agent;
  v. the spacers are fixed to the respective inner surface of one or both of the plates;
(b) depositing the sample on the inner surface of at least one of the two plates when the two plates are in the open configuration, in which: the two plates are partially or entirely separated apart and the spacing between the plates is not regulated by the spacing mechanism;
(c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the binding site and storage site;
(d) releasing the detection agent into the thin layer through the controlled release agent, wherein the controlled release agent is configured to render the detection agent substantially released at a first time point after the target analyte in the thin layer is substantially bound to the binding agent; and
(e) after step (d), incubating the assay for a time period no shorter than the average time it takes for the detection agent to diffuse across the thickness of the thin layer and analyzing the target analyte in the thin layer,
  wherein the detection agent and the binding agent are configured to bind either directly or indirectly, bringing about a target analyte-related signal indicative of the presence or quantity of the target analyte;
  wherein in the direct binding, the detection agent competes with the target analyte and directly binds to the binding agent; and
  wherein in the indirect binding, the binding agent and the detection agent bind to the target analyte at different locations.

In some embodiments, the controlled release agent is the slow release agent, and the controlling step (d) of the method is performed without any action from the user of the device, but rather the slow release agent works by itself to delay the release of the detection agent through the mechanism(s) as discussed above.

In some embodiments, the controlled release agent is the stimulus-dependent agent, and the controlling step (d) of the method comprises: after the target analyte in the thin layer is substantially bound to the binding agent, delivering a stimulus to the stimulus-dependent agent to trigger the release of the detection agent into the thin layer. The stimulus-dependent release of the detection agent takes place through the mechanism(s) as discussed above.

In some embodiments of the present invention, the assay is non-competitive sandwich assay, in which: the binding agent and the detection agent are configured to specifically bind to the target analyte at different locations, bringing about a target analyte-relevant signal indicative of the presence or quantity of the target analyte.

In some embodiments of the present invention, the assay is competitive binding assay, in which: the binding agent is configured to bind specifically to both the target analyte and the detection agent, and the binding between the detection agent and the binding agent competes with the binding between the target analyte and the binding agent and brings about a target analyte-related signal indicative of the presence or quantity of the target analyte.

In some embodiments, the method is for one-step bio/chemical assays and comprises the steps of:
(a) providing a first plate, a second plate, and spacers, wherein:
   i. the first plate and second plate are movable relative to each other into different configurations, including an open configuration and a closed configuration;
   ii. each of the plates comprises an inner surface for contacting a sample that contains a target analyte;
   iii. the second plate comprises, on its inner surface, a storage site that contains a detection agent and a controlled release agent that is mixed with or coated on top of the detection agent;
   iv. the spacers are fixed to the respective inner surface of one or both of the plates;
(b) depositing the sample on the inner surface of at least one of the two plates when the two plates are in the open configuration, in which: the two plates are partially or entirely separated apart and the spacing between the plates is not regulated by the spacing mechanism;
(c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the storage site;
(d) releasing the detection agent into the thin layer through the controlled release agent, wherein the controlled release agent is configured to render the detection agent substantially released at a first time point after the two plates are compressed into the closed configuration; and
(e) after step (d), incubating the assay for a time period no shorter than a relevant time and analyzing the target analyte in the thin layer,
   wherein the detection agent binds to or reacts with the target analyte, bringing out a target analyte-relevant signal indicative of the presence or quantity of the target analyte; and
   wherein the relevant time is the average time it takes for the detection agent to diffuse across the thickness of the thin layer.

D.5 Different Release Time

Another aspect of the present invention is to provide a QMAX device that is configured to control the substantial release of detection agent at different locations with different release time.

In some embodiments, the QMAX device comprises more than one type of controlled release agents that are mixed with or coated on top of the detection agent at different locations. In some embodiments, the second plate comprises a first controlled release agent at a first location and a second controlled release agent at a second location. The detection agent at the first location is of a different type than the detection agent at the second location, or they are of the same type but different amounts, or they are of the same type and same amount.

The first and second releasing control agents are configured to render the detection agents at the two locations substantially released at different time. For instance, the first and second controlled releasing control agents are both soluble slow release agents but have different dissolution rate, and the detection agents are not substantially released until the partial or full dissolution of the first or second slow release agent at the respective location. Or in another case, the first and second controlled release agents are both insoluble slow release agents and regulate the release time of the detection agent by limiting its contact with the sample through its porous polymer structure, and the first and second slow release agents have different "pore" sizes so that their permeability to the sample is different and the detection agent at the two locations are substantially released at different time. Or in another case, the first and second controlled release agents are both stimulus-sensitive release agents, and yet they are responsive to different stimuli or different intensity of the same type of stimulus, thereby rendering different release time for detection agents at different locations. Or in another case, the first and second releasing control agents are different species and regulate the release time of the detection agent through different mechanisms, and yet the release time for the detection agent rendered by them are different.

In some embodiments, the device for releasing detection agent into a portion of a liquid sample at different time, comprising:
a first plate, a second plate, and spacers, wherein:
   i. the plates are movable relative to each other into different configurations, including an open configuration and a closed configuration;
   ii. each of the plates comprises an inner surface for contacting a sample that contains a target analyte;
   iii. the second plate comprises, on its inner surface, a first storage site that contains a first detection agent and a first controlled release agent, and a second storage site that contains a second detection agent and a second controlled release agent, wherein the first and second controlled release agent are mixed with or coated on top of the first and second detection agent, respectively;
   iv. the spacers are fixed to the respective inner surface of one or both of the plates;
wherein in the open configuration: the two plates are either partially or completely separated apart, the spacing between the plates is not regulated by the spacers, allowing the sample to be deposited on one or both of the plates,
wherein the closed configuration is configured after the sample deposition in the open configuration; and in the closed configuration: at least part of the sample is compressed by the two plates into a thin layer that is confined by the two plates and regulated by the spacers,
wherein at least a part of the thin layer is in touch with the storage site;
wherein the detection agent binds to or reacts with the target analyte; and wherein the first and second controlled release agent are configured to render the first and second detection agent substantially released into the sample at different first time points, respectively.

In some embodiments, the QMAX device comprises more than two controlled release agents at different locations and each of them render a different release time for the detection agent at the respective location. In some embodiments, the number of different types of controlled release is 3 or more, 4 or more, 5 or more, 10 or more, 20 or more, 50 or more, 100 or more, 200 or more, 500 or more, 1000 or more, or within any range of any two of these values.

Another aspect of the present invention is to provide a method of utilizing QMAX device for bio/chemical assays with controlled detection agents release at different time.

In some embodiments, the method comprises the steps of:
(a) providing a first plate and a second plate, wherein:
   i. the first plate and second plate are movable relative to each other into different configurations, including an open configuration and a closed configuration;
   ii. each of the plates comprises an inner surface for contacting a sample that contains a target analyte;
   iii. the first plate comprises, on its inner surface, a binding site that contains a binding agent capable of binding the target analyte;
   iv. the second plate comprises, on its inner surface, a storage site that contains a detection agent, a first and a second controlled release agents that are mixed with or coated on top of the detection agent at a first location and a second location, respectively;
   v. one or both of the plates have spacers that are fixed to the respective inner surface;
(b) depositing the sample on the inner surface of at least one of the two plates when the two plates are in the open configuration, in which: the two plates are partially or entirely separated apart and the spacing between the plates is not regulated by the spacing mechanism;
(c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the binding site and the storage site;
(d) controlling the release of the detection agent into the thin layer through the controlled release agent, wherein the controlled release agent is configured to render the substantial release of the detection agent after the target analyte in the thin layer is substantially bound to the binding agent; and
(e) after step (d), incubating the assay for a time period no shorter than a relevant time and analyzing the target analyte in the thin layer.

In some embodiments, the method is for a one-step bio/chemical assay and comprises the steps of:
(a) providing a first plate and a second plate, wherein:
   i. the first plate and second plate are movable relative to each other into different configurations, including an open configuration and a closed configuration;
   ii. each of the plates comprises an inner surface for contacting a sample that contains a target analyte;
   iii. the second plate comprises, on its inner surface, a storage site that contains a detection agent, a first and a second controlled release agents that are mixed with or coated on top of the detection agent at a first location and a second location, respectively;
   iv. one or both of the plates have spacers that are fixed to the respective inner surface;
(b) depositing the sample on the inner surface of at least one of the two plates when the two plates are in the open configuration, in which: the two plates are partially or entirely separated apart and the spacing between the plates is not regulated by the spacing mechanism;
(c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the storage site;
(d) releasing the detection agent into the thin layer through the controlled release agent, wherein the controlled release agent is configured to render the substantial release of the detection agent after the two plates are compressed into the closed configuration; and
(e) after step (d), incubating the assay for a time period no shorter than a relevant time and analyzing the target analyte in the thin layer,
   wherein the detection agent binds to or reacts with the target analyte, bringing out a target analyte-relevant signal indicative of the presence or quantity of the target analyte.

D.6 Examples of Present Invention

DA1. A device for slow release of a reagent into a liquid sample, comprising:
   a first plate, a second plate, and spacers, wherein:
      iii. the plates are movable relative to each other into different configurations, including an open configuration and a closed configuration;
      iv. each of the plates comprises an inner surface for contacting a sample that contains a target analyte;
      v. the first plate comprises, on its inner surface, a binding site that contains a binding agent;
      vi. the second plate comprises, on its inner surface, a storage site that contains a detection agent and a slow release agent that is mixed with or coated on top of the detection agent;
      vii. the spacers are fixed to the respective inner surface of one or both of the plates;
   wherein in the open configuration: the two plates are either partially or completely separated apart, the spacing between the plates is not regulated by the spacers, allowing the sample to be deposited on one or both of the plates,
   wherein the closed configuration is configured after the sample deposition in the open configuration; and in the closed configuration: at least part of the sample is compressed by the two plates into a thin layer that is confined by the two plates and regulated by the spacers, wherein at least a part of the thin layer is in touch with the binding site and storage site;
   wherein the detection agent and the binding agent are configured to bind either directly or indirectly;
   wherein in the direct binding, the detection agent competes with the target analyte and directly binds to the binding agent;
   wherein in the indirect binding, the binding agent and the detection agent bind to the target analyte at different locations; and
   wherein the slow release agent is configured to autonomously render the detection agent substantially released at a first time point after the target analyte is substantially bound to the binding agent.

DA2. A device for slow release of a reagent into a liquid sample, comprising:
   a first plate, a second plate, and spacers, wherein:
      i. the plates are movable relative to each other into different configurations, including an open configuration and a closed configuration;
      ii. each of the plates comprises an inner surface for contacting a sample that contains a target analyte;
      iii. the second plate comprises, on its inner surface, a storage site that contains a detection agent and a slow release agent that is mixed with or coated on top of the detection agent; and
      iv. the spacers are fixed to the respective inner surface of one or both of the plates;

wherein in the open configuration: the two plates are either partially or completely separated apart, the spacing between the plates is not regulated by the spacers, allowing the sample to be deposited on one or both of the plates, wherein the closed configuration is configured after the sample deposition in the open configuration; and in the closed configuration: at least part of the sample is compressed by the two plates into a thin layer that is confined by the two plates and regulated by the spacers, wherein at least a part of the thin layer is in touch with the storage site;

wherein the detection agent is configured to bind to or react with the target analyte; and wherein the slow release agent is configured to autonomously render the detection agent substantially released at a first time point after the two plates are compressed into the closed configuration.

DB1. A device for temporally and spatially controlled release of a reagent into a liquid sample, comprising:
- a first plate, a second plate, and spacers, wherein:
  - i. the plates are movable relative to each other into different configurations, including an open configuration and a closed configuration;
  - ii. each of the plates comprises an inner surface for contacting a sample that contains a target analyte;
  - iii. the first plate comprises, on its inner surface, a binding site that contains a binding agent;
  - iv. the second plate comprises, on its inner surface, a storage site that contains a detection agent and a slow release agent that is mixed with or coated on top of the detection agent; and
  - v. the spacers are fixed to the respective inner surface of one or both of the plates;

wherein in the open configuration: the two plates are either partially or completely separated apart, the spacing between the plates is not regulated by the spacers, allowing the sample to be deposited on one or both of the plates, wherein the closed configuration is configured after the sample deposition in the open configuration; and in the closed configuration: at least part of the sample is compressed by the two plates into a thin layer that is confined by the two plates and regulated by the spacers, wherein at least a part of the thin layer is in touch with the binding site and storage site;

wherein the detection agent and the binding agent are configured to bind either directly or indirectly;

wherein in the direct binding, the detection agent competes with the target analyte and directly binds to the binding agent;

wherein in the indirect binding, the binding agent and the detection agent bind to the target analyte at different locations; and wherein the stimulus-dependent release agent is configured to be specifically responsive to a stimulus, retaining the detection agent on the plate in the absence of the stimulus and releasing the detection agent upon receipt of the stimulus.

DB2. A device for temporally and spatially controlled release of a reagent into a portion of a liquid sample, comprising:
- a first plate, a second plate, and spacers, wherein:
  - i. the plates are movable relative to each other into different configurations, including an open configuration and a closed configuration;
  - ii. each of the plates comprises an inner surface for contacting a sample that contains a target analyte;
  - iii. the second plate comprises, on its inner surface, a storage site that contains a detection agent and a stimulus-sensitive release agent that is mixed with or coated on top of the detection agent; and
  - iv. the spacers are fixed to the respective inner surface of one or both of the plates;

wherein in the open configuration: the two plates are either partially or completely separated apart, the spacing between the plates is not regulated by the spacers, allowing the sample to be deposited on one or both of the plates, wherein the closed configuration is configured after the sample deposition in the open configuration; and in the closed configuration: at least part of the sample is compressed by the two plates into a thin layer that is confined by the two plates and regulated by the spacers, wherein at least a part of the thin layer is in touch with the storage site;

wherein the detection agent is configured to bind to or react with the target analyte; and wherein the stimulus-dependent release agent is configured to be specifically responsive to a stimulus, retaining the detection agent on the plate in the absence of the stimulus and releasing the detection agent upon receipt of the stimulus.

DC1. A method for a two-step affinity binding assay, comprising the steps of:
- (a) providing a first plate, a second plate, and spacers, wherein:
  - i. the first plate and second plate are movable relative to each other into different configurations, including an open configuration and a closed configuration;
  - ii. each of the plates comprises an inner surface for contacting a sample that contains a target analyte;
  - iii. the first plate comprises, on its inner surface, a binding site that contains a binding agent capable of binding the target analyte;
  - iv. the second plate comprises, on its inner surface, a storage site that contains a detection agent and a controlled release agent that is mixed with or coated on top of the detection agent; and
  - v. the spacers are fixed to the respective inner surface of one or both of the plates;
- (b) depositing the sample on the inner surface of at least one of the two plates when the two plates are in the open configuration, in which: the two plates are partially or entirely separated apart and the spacing between the plates is not regulated by the spacing mechanism;
- (c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the binding site and storage site;
- (d) releasing the detection agent into the thin layer through the controlled release agent, wherein the controlled release agent is configured to render the detection agent substantially released at a first time point after the target analyte in the thin layer is substantially bound to the binding agent; and
- (e) after step (d), incubating the assay for a time period no shorter than the average time it takes for the detection agent to diffuse across the thickness of the thin layer and analyzing the target analyte in the thin layer,
  - i. wherein the detection agent and the binding agent are configured to bind either directly or indirectly, bringing about a target analyte-related signal indicative of the presence or quantity of the target analyte;

ii. wherein in the direct binding, the detection agent competes with the target analyte and directly binds to the binding agent; and iii. wherein in the indirect binding, the binding agent and the detection agent bind to the target analyte at different locations.

DC2. A method for a one-step assay, comprising the steps of:
(a) providing a first plate, a second plate, and spacers, wherein:
  i. the first plate and second plate are movable relative to each other into different configurations, including an open configuration and a closed configuration;
  ii. each of the plates comprises an inner surface for contacting a sample that contains a target analyte;
  iii. the second plate comprises, on its inner surface, a storage site that contains a detection agent and a controlled release agent that is mixed with or coated on top of the detection agent; and
  iv. the spacers are fixed to the respective inner surface of one or both of the plates;
(b) depositing the sample on the inner surface of at least one of the two plates when the two plates are in the open configuration, in which: the two plates are partially or entirely separated apart and the spacing between the plates is not regulated by the spacing mechanism;
(c) compressing at least part of the deposited sample by bringing the two plates into a closed configuration, in which: the thickness of said at least part of the deposited sample is reduced, compared to that in the open configuration of the plates, into a thin layer that is confined by the inner surfaces of the plates and in touch with the storage site;
(d) releasing the detection agent into the thin layer through the controlled release agent, wherein the controlled release agent is configured to render the detection agent substantially released at a first time point after the two plates are compressed into the closed configuration; and
(e) after step (d), incubating the assay for a time period no shorter than a relevant time and analyzing the target analyte in the thin layer,
  i. wherein the detection agent binds to or reacts with the target analyte, bringing out a target analyte-relevant signal indicative of the presence or quantity of the target analyte; and
  ii. wherein the relevant time is the average time it takes for the detection agent to diffuse across the thickness of the thin layer.

DD1. A device for releasing detection agent into a portion of a liquid sample at different time, comprising:
a first plate, a second plate, and spacers, wherein:
  i. the plates are movable relative to each other into different configurations, including an open configuration and a closed configuration;
  ii. each of the plates comprises an inner surface for contacting a sample that contains a target analyte;
  iii. the second plate comprises, on its inner surface, a first storage site that contains a first detection agent and a first controlled release agent, and a second storage site that contains a second detection agent and a second controlled release agent, wherein the first and second controlled release agent are mixed with or coated on top of the first and second detection agent, respectively; and
  iv. the spacers are fixed to the respective inner surface of one or both of the plates;

wherein in the open configuration: the two plates are either partially or completely separated apart, the spacing between the plates is not regulated by the spacers, allowing the sample to be deposited on one or both of the plates, wherein the closed configuration is configured after the sample deposition in the open configuration; and in the closed configuration: at least part of the sample is compressed by the two plates into a thin layer that is confined by the two plates and regulated by the spacers, wherein at least a part of the thin layer is in touch with the storage site;

wherein the detection agent binds to or reacts with the target analyte; and wherein the first and second controlled release agent are configured to render the first and second detection agent substantially released into the sample at different first time points, respectively.

DA3. The device of embodiment DA1 or DA2, wherein the slow release agent is soluble in the sample and configured to be substantially dissolved in the sample no earlier than the first time point.

DA4. The device of any one of prior embodiments, wherein the slow release agent is insoluble in the sample and limits the contact of the detection agent by the sample.

DA5. The device of any one of prior embodiments, wherein the slow release agent is made from a material selected from the group consisting of: PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

DA6. The device of any one of prior embodiments, wherein the spacers have a maximum height of 250 μm or less.

DA7. The device of any one of prior embodiments, wherein the spacers have a predetermined substantially uniform height that is 250 μm or less.

DA8. The device of any one of prior embodiments, wherein the spacers have a predetermined constant inter-spacer distance.

DA9. The device of any one of prior embodiments, wherein the spacers are fixed with the respective inner surface of one or both of the plates.

DA10. The device of any one of prior embodiments, wherein at least one of the spacers is inside the sample contact area.

DA11. The device of any one of embodiments DA7-DA10, wherein the thin layer has a substantially uniform thickness that is about the uniform height of the spacers.

DB3. The device of embodiment DB1 or DB2, wherein the stimulus-dependent release agent forms cross-links with the detection agent that retain the detection agent in the absence of the stimulus, and wherein the cross-links are altered by the stimulus, resulting in the release of the detection agent.

DB4. The device of any one of prior embodiments, wherein the stimulus-dependent release agent is configured to form polymer autonomously that retains the detection agent in the absence of the stimulus, and wherein the polymer is depolymerized by the stimulus, resulting in the release of the detection agent.

DB5. The device of any one of prior embodiments, wherein the stimulus is selected from the group consisting of: radio wave, microwave, infrared radiation, visible light, ultraviolet radiation, X-rays, and gamma rays, temperature, pH, ion, magnetic stimulus, mechanical stimulus (e.g. mechanical compression, mechanical impact, ultrasound), and electrical stimulus.

DB6. The device of any one of prior embodiments, wherein the stimulus-dependent release agent is made from a material selected from the group consisting of: (E)-(2-Hydroxyphenyl)acrylates, 2-Aroylbenzoates, Xanthenoic esters, 2-Nitrobenzyl derivatives, 1-Alkoxy-9,10-anthraquinones, 2-Oxoacetates, Alkyl phenyl ketones, 4-benzoyl-phenylalanine, amino-coumarin family, Perylene, 1-Acetylperylene, 2-nitrophenyl)propryloxycarbonyl, Ruthenium complex, Chlorophyllin, Phthalocyanin, Distearoyl indocarbocyanine, Azobenzene, 2-diazo-1,2-nathoquinone, Merocyanine/spiropyran, Donor-acceptor stenhouse adducts, coumarin-modified mesoporous bioactive glass, N-isopropylacrylamide, N, N-dimethylaminoethyl methacrylate (PNIPAm-co-PDMAEMA), Linear PNI-Pam-co-DMAEMA Polymer, PEI-PNIPAm polymer with 46-kDa PNIPAm grafts, Poly [2-(2-ethoxy) ethoxy ethylvinyl ether (EOEOVE), Multi-block copolymers synthesized from pluronic and di-(ethylene glycol) divinyl ether, Polyethylenimine (BPEI)/pDNA complex, Co-polymerization of PVP and acrylic acid, Pluronic-g-PAA copolymers, Liposomes attached with a saccharide (lecithin) vector, PEGylated liposome, Copolymer of N-isopropylacryl amide and acryloylpyrrolidine (sterically stabilized liposome), Histidine-modified galactosylated cholesterol derivative—cationic liposome, Anionic liposomes containing phosphatidylethanolamine (PE), Amphiphilic co-polymer of poly (methoxy-polyethylene glycol cyanoacrylate-cO-n-hexadecyl cyano acrylate) (PEG-PH DCA), Polyethylene Poly (phthaloyl-L-lysine), Polyamidoamine dendrimer, Poly (alkylcyanoacrylate) nanoparticles, Poly (methylmethacrylate) Nanoparticles, Poly (alkylcyanoacrylate) Polyester Nanoparticles, Albumin, Chitosan, Dextran, Poly (N-isopropylacrylamidecobutyl-methacrylate-co-acrylic acid), Poly (N-isopropylacrylamide, polysaccharides, gelrite, alginate/HPmC, sod alginate/HPC, gelrite gellan gum, and tamarind.

DB7. The device of any one of prior embodiments, wherein the spacers have a maximum height of 250 μm or less.

DB8. The device of any one of prior embodiments, wherein the spacers have a predetermined substantially uniform height that is 250 μm or less.

DB9. The device of any one of prior embodiments, wherein the spacers have a predetermined constant inter-spacer distance.

DB10. The device of any one of prior embodiments, wherein the spacers are fixed with the respective inner surface of one or both of the plates.

DB11. The device of any one of prior embodiments, wherein at least one of the spacers is inside the sample contact area.

DC3. The method of embodiment DC1 or DC2, wherein the controlled release agent is a slow release agent that is configured to autonomously render the detection agent substantially released at the first time point, and wherein the releasing step (d) is performed without external actions.

DC4. The method of any one of embodiments DC1 or DC2, wherein the controlled release agent is a stimulus-sensitive agent that is configured to be specifically responsive to a stimulus, retaining the detection agent on the plate in the absence of the stimulus and releasing the detection agent upon receipt of the stimulus, and wherein the releasing step (d) comprises: after the target analyte in the thin layer is substantially bound to the binding agent, delivering the stimulus to the stimulus-dependent agent to trigger the release of the detection agent into the thin layer.

DD2. The device of embodiment DD1, wherein at least one of the controlled release agents is a slow release agent that is configured to autonomously render the detection agent substantially released at the respective first time point.

DD3. The device of embodiment DD1 or DD2, wherein at least one of the controlled release agents is a stimulus-sensitive agent that is configured to be specifically responsive to a stimulus, retaining the detection agent on the plate in the absence of the stimulus and releasing the detection agent upon receipt of the stimulus.

E. Uniform Sample Thickness Pressed by an Imprecise Force.

In some embodiments of devices or methods of forming uniform sample thickness by pressing with an imprecise force described herein and in the provisional 62/456,504, filed on Feb. 8, 2017, which is incorporated herein in the its entirety for all purposes.

In some embodiments, the imprecise force is around 0.01 kg, 0.05 kg, 0.1 kg, 0.25 kg, 0.5 kg, 1 kg, 2.5 kg, 5 kg, 7.5 kg, 10 kg, 20 kg, 25 kg, 30 kg, 40 kg, 50 kg, 60 kg, 70 kg, 80 kg, 100 kg, 200 kg, or in a range between any two of these values; and a preferred range of 0.5-2 kg, 2-5 kg, 5-7.5 kg, 7.5-10 kg, 10-20 kg, 20-40 kg, 40-60 kg, or 60-100 kg.

In some embodiments, the imprecise force is applied by human hand, for example, e.g., by pinching an object together between a thumb and index finger, or by pinching and rubbing an object together between a thumb and index finger.

In some embodiments, the hand pressing force is around 0.05 kg, 0.1 kg, 0.25 kg, 0.5 kg, 1 kg, 2.5 kg, 5 kg, 7.5 kg, 10 kg, 20 kg, 25 kg, 30 kg, 40 kg, 50 kg, 60 kg, or in a range between any two of these values; and a preferred range of 0.5-1 kg, 1-2 kg, 2-4 kg, 4-6 kg, 6-10 kg, 10-20 kg, 20-40 kg, or 40-60 kg.

In some embodiments, the hand pressing has a pressure of 0.01 $kg/cm^2$, 0.1 $kg/cm^2$, 0.5 $kg/cm^2$, 1 $kg/cm^2$, 2 $kg/cm^2$, 2.5 $kg/cm^2$, 5 $kg/cm^2$, 10 $kg/cm^2$, 20 $kg/cm^2$, 30 $kg/cm^2$, 40 $kg/cm^2$, 50 $kg/cm^2$, 60 $kg/cm^2$, 100 $kg/cm^2$, 150 $kg/cm^2$, 200 $kg/cm^2$, or a range between any two of the values; and a preferred range of 0.1 $kg/cm^2$ to 0.5 $kg/cm^2$, 0.5 $kg/cm^2$ to 1 $kg/cm^2$, 1 $kg/cm^2$ to 5 $kg/cm^2$, or 5 $kg/cm^2$ to 10 $kg/cm^2$.

As used herein, the term "imprecise" in the context of a force (e.g. "imprecise pressing force") refers to a force that (a) has a magnitude that is not precisely known or precisely predictable at the time the force is applied;

(b) varies in magnitude from one application of the force to the next; and (c) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

EA. Imprecise Force, Specify IGS^4/hE

EA1. A device for forming a thin fluidic sample layer with a uniform predetermined thickness by pressing with an imprecise pressing force, comprising:

a first plate, a second plate, and spacers, wherein:
 i. the plates are movable relative to each other into different configurations;
 ii. one or both plates are flexible;
 iii. each of the plates comprises an inner surface that has a sample contact area for contacting a fluidic sample;
 iv. each of the plates comprises, on its respective outer surface, a force area for applying an imprecise pressing force that forces the plates together;
 v. one or both of the plates comprise the spacers that are permanently fixed on the inner surface of a respective plate;

vi. the spacers have a predetermined substantially uniform height that is equal to or less than 200 microns, and a predetermined fixed inter-spacer-distance;
vii. the fourth power of the inter-spacer-distance (IDS) divided by the thickness (h) and the Young's modulus (E) of the flexible plate (ISD$^4$/(hE)) is $5\times10^6$ um$^3$/GPa or less; and
viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

EA2. A method of forming a thin fluidic sample layer with a uniform predetermined thickness by pressing with an imprecise pressing force, comprising the steps of:
(a) obtaining a first plate, a second plate, and spacers, wherein:
  i. the plates are movable relative to each other into different configurations;
  ii. one or both plates are flexible;
  iii. each of the plates comprises an inner surface that has a sample contact area for contacting a fluidic sample;
  iv. each of the plates comprises, on its respective outer surface, a force area for applying an imprecise pressing force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined fixed inter-spacer-distance;
  vii. the fourth power of the inter-spacer-distance (IDS) divided by the thickness (h) and the Young's modulus (E) of the flexible plate (ISD$^4$/(hE)) is $5\times10^6$ um$^3$/GPa or less; and
  viii. at least one of the spacers is inside the sample contact area;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

EB. Hand Pressing, Specify Spacer Hardness-Contact Area Product

EB1. A device for forming a thin fluidic sample layer with a uniform predetermined thickness by pressing with an imprecise force, comprising:
a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein the force that presses the two plates into the closed configuration is an imprecise pressing force provided by human hand.

EB2. A method of forming a thin fluidic sample layer with a uniform predetermined thickness by pressing with an imprecise pressing force, comprising the steps of:
(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;

iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger; and
viii. at least one of the spacers is inside the sample contact area;

(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

EC. Hand pressing, Specify IDS/hE & Spacer Hardness-Contact Area Product

EC1. A device for forming a thin fluidic sample layer with a uniform predetermined thickness by pressing with an imprecise force, comprising:
a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger; and
viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
wherein the force that presses the two plates into the closed configuration is imprecise, and is provided by human hand.

EC2. A method of forming a thin fluidic sample layer with a uniform predetermined thickness by pressing with an imprecise pressing force, comprising the steps of:
(a) obtaining a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger; and
viii. at least one of the spacers is inside the sample contact area;

(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

ED. Hand pressing, Specify Pillar Spacer and Ratio of IDS/W

ED1. A device for forming a thin fluidic sample layer with a uniform predetermined thickness by pressing with an imprecise force, comprising:

a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger.
  viii. at least one of the spacers is inside the sample contact area; and wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the force that presses the two plates into the closed configuration is imprecise, and is provided by human hand.

ED2. A method of forming a thin fluidic sample layer with a uniform predetermined thickness by pressing with an imprecise pressing force, comprising the steps of:

(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger.
  viii. at least one of the spacers is inside the sample contact area; and (b) obtaining a fluidic sample;

(c) depositing the sample on one or both of the plates; when the plates are configured in an open configuration, wherein the open configuration is a configuration in which the two plates are partially or completely separated apart and the spacing between the plates is not regulated by the spacers;

(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

EE. Volume Determination, Specify IGS^4/hE

EE1. A device for determining a relevant sample volume by pressing with an imprecise force provided by human hand, comprising:

a first plate, a second plate, spacers, and an area-determination device, wherein:
  i. the plates are movable relative to each other into different configurations;
  ii. one or both plates are flexible;
  iii. each of the plates comprises, on its respective inner surface, a sample contact area for contacting and/or compressing a fluidic sample that has a relevant volume to be measured;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined constant inter-spacer-distance;

vii. a fourth power of the inter-spacer-distance (IDS) divided by the thickness (h) and the Young's modulus (E) of the flexible plate (ISD$^4$/(hE)) is $5 \times 10^6$ um$^3$/GPa or less.

viii. at least one of the spacers is inside the sample contact area; and ix. the area-determination device is configured to determine the lateral area of the relevant volume;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the relevant volume of the sample is a partial or entire volume of the uniform thickness layer and the value of the relevant volume is determined by the uniform thickness and the determined lateral area; and wherein the force that presses the two plates into the closed configuration is imprecise, and is provided by human hand.

The device of any prior embodiment, wherein the area-determination device is a camera.

The area-determination device comprises an area in the sample contact area of a plate, wherein the area is less than $\frac{1}{100}$, $\frac{1}{20}$, $\frac{1}{10}$, $\frac{1}{6}$, $\frac{1}{5}$, $\frac{1}{4}$, $\frac{1}{3}$, $\frac{1}{2}$, $\frac{2}{3}$ of the sample contact area, or in a range between any of the two values.

The area-determination device comprises a camera and an area in the sample contact area of a plate, wherein the area is in contact with the sample.

EE2. A method of forming a thin fluidic sample layer with a uniform predetermined thickness by pressing with an imprecise pressing force, comprising the steps of:

(a) obtaining a first plate, a second plate, and spacers, wherein:

i. the plates are movable relative to each other into different configurations;

ii. one or both plates are flexible;

iii. each of the plates comprises, on its respective inner surface, a sample contact area for contacting and/or compressing a fluidic sample that has a relevant volume to be measured;

iv. each of the plates comprises, on its respective outer surface, an area for applying a force that forces the plates together;

v. one or both of the plates comprise the spacers that are permanently fixed on the inner surface of a respective plate;

vi. the spacers have a predetermined substantially uniform height that is equal to or less than 200 microns, and a predetermined constant inter-spacer-distance;

vii. a fourth power of the inter-spacer-distance (IDS) divided by the thickness (h) and the Young's modulus (E) of the flexible plate (ISD$^4$/(hE)) is $5 \times 10^6$ um$^3$/GPa or less.

viii. at least one of the spacers is inside the sample contact area; and ix. the area-determination device is configured to determine the lateral area of the relevant volume;

(b) obtaining a fluidic sample;

(c) depositing the sample on one or both of the plates; when the plates are configured in an open configuration, wherein the open configuration is a configuration in which the two plates are partially or completely separated apart and the spacing between the plates is not regulated by the spacers;

(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

EF. Volume Determination, Specify IGS^4/hE

EF1. A device for determining a relevant sample volume by pressing with an imprecise force provided by human hand, comprising:

a first plate, a second plate, spacers, and area-determination device, wherein:

i. the plates are movable relative to each other into different configurations;

ii. one or both plates are flexible;

iii. each of the plates comprises, on its respective inner surface, a sample contact area for contacting and/or compressing a fluidic sample that has a relevant volume to be measured;

iv. each of the plates comprises, on its respective outer surface, an area for applying a force that forces the plates together;

v. one or both of the plates comprise the spacers that are permanently fixed on the inner surface of a respective plate;

vi. the spacers have a predetermined substantially uniform height that is equal to or less than 200 microns, and a predetermined constant inter-spacer-distance;

vii. a fourth power of the inter-spacer-distance (IDS) divided by the thickness (h) and the Young's modulus (E) of the flexible plate (ISD$^4$/(hE)) is $5 \times 10^6$ um$^3$/GPa or less.

viii. at least one of the spacers is inside the sample contact area; and ix. the area-determination device is configured to determine the lateral area of the relevant volume;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the relevant volume of the sample is a partial or entire volume of the uniform thickness layer and the value of the relevant volume is determined by the uniform thickness and the determined lateral area; and wherein the force that presses the two plates into the closed configuration is imprecise, and is provided by human hand.

EF2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;
    iii. each of the plates comprises, on its respective inner surface, a sample contact area for contacting and/or compressing a fluidic sample that has a relevant volume to be measured;
    iv. each of the plates comprises, on its respective outer surface, an area for applying a force that forces the plates together;
    v. one or both of the plates comprise the spacers that are permanently fixed on the inner surface of a respective plate;
    vi. the spacers have a predetermined substantially uniform height that is equal to or less than 200 microns, and a predetermined constant inter-spacer-distance;
    vii. a fourth power of the inter-spacer-distance (IDS) divided by the thickness (h) and the Young's modulus (E) of the flexible plate ($ISD^4/(hE)$) is $5 \times 10^6$ um$^3$/GPa or less.
    viii. at least one of the spacers is inside the sample contact area; and
    ix. the area-determination device is configured to determine the lateral area of the relevant volume;
  (b) obtaining a fluidic sample;
  (c) depositing the sample on one or both of the plates; when the plates are configured in an open configuration, wherein the open configuration is a configuration in which the two plates are partially or completely separated apart and the spacing between the plates is not regulated by the spacers;
  (d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
    bringing the two plates together; and
    conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
  wherein the force that presses the two plates into the closed configuration is an imprecise pressing force provided by human hand.

EG. Extra

The term "imprecise force" refers to a force that has a magnitude that is completely unknown, known only in a magnitude range but not in a particular magnitude value (the magnitude range varies at least 20% from the minimum to the maximum of the range), or unpredictable at the time that a force is applied. Examples of an imprecise force include that the magnitude of an imprecise force may vary from one application of the force to the next, may be uneven across the area upon which the force is applied, and may vary over the time that the force is being applied. An imprecise force does not need to be measured at the time that it is applied.

The devices or methods of any prior embodiment, wherein the deformable sample is a fluidic sample.

The devices or methods of any prior embodiment, wherein the deformable sample is a liquid sample.

The devices or methods of any prior embodiment, wherein the imprecision force has a variation at least 30% of the total force that actually is applied.

The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.

1. The device of any prior embodiment, wherein spacers have a flat top.
2. The device of any prior embodiment, wherein the device is further configured to have, after the pressing force is removed, a sample thickness that is substantially the same in thickness and uniformity as that when the force is applied.
3. The device of any prior embodiment, wherein the imprecise force is provided by human hand.
4. The device of any prior embodiment, wherein the inter spacer distance is substantially constant.
5. The device of any prior embodiment, wherein the inter spacer distance is substantially periodic in the area of the uniform sample thickness area.
6. The device of any prior embodiment, wherein the multiplication product of the filling factor and the Young's modulus of the spacer is 2 MPa or larger.
7. The device of any prior embodiment, wherein the force is applied by hand directly or indirectly.
8. The device of any prior embodiment, wherein the force applied is in the range of 5 N to 20 N.
9. The device of any prior embodiment wherein the highly uniform layer has a thickness that varies by less than 15%, 10%, or 5% of an average thickness.
10. The device of any prior embodiment, wherein the imprecise force is applied by pinching the device between a thumb and forefinger.
11. The device of any prior embodiment, wherein the predetermined sample thickness is larger than the spacer height.
12. The device of any prior embodiment, wherein the device holds itself in the closed configuration after the pressing force has been removed.
13. The device of any prior embodiment, wherein the uniform thickness sample layer area is larger than that area upon which the pressing force is applied.

14. The device of any prior embodiment, wherein the spacers do not significantly deform during application of the pressing force.

15. The device of any prior embodiment, wherein the pressing force is not predetermined beforehand and is not measured.

F. Binding Site and Storage Site on the Same Plate

Another aspect of the present invention provides devices and methods for bio/chemical assays using QMAX device in which binding site and storage site are on the same plate, meaning both capture agent and second agent are coated on the same plate.

FA1. A method for assaying a sample, comprising
  (a) obtaining a first plate comprising, on its inner surface, a sample contact area for contacting a sample that contains a target analyte;
  (b) obtaining a second plate comprising a sample contact area that comprises an assaying area, wherein the assaying area comprises
    (i) an immobilized capture agent that binds a target analyte in a sample, and
    (ii) a second agent that is capable of, upon contacting the sample, diffusing in the sample;
    wherein the first plate and second plate are movable relative to each other into different configurations, including an open and a closed configurations;
  (c) depositing, in the open configuration, the sample on one or both of the sample contact areas of the plates, wherein in the open configuration, the sample contact areas of the plates are separated larger than 200 um;
  (d) after (c), bringing the two plates to a closed configuration, wherein, in the closed configuration, at least part of the sample deposited in (c) is confined between the sample contact areas of the two plates, and has an average thickness in the range of 0.01 to 200 μm; and
  (e) detecting a signal related to an analyte that is captured by the binding site.

FB1. A device for performing a competitive assay, comprising:
  a first plate comprising, on its inner surface, a sample contact area for contacting a sample that contains a target analyte;
  a second plate comprising a sample contact area that comprises an assaying area, wherein the assaying area comprises
    (i) an immobilized capture agent that binds a target analyte in a sample, and
    (ii) a second agent that is capable of, upon contacting the sample, diffusing in the sample;
    wherein the first plate and second plate are movable relative to each other into different configurations;
    wherein one of the configurations is an open configuration, in which the plates are partially or entirely separated apart, and the average spacing between the sample contact areas of the plates is larger than 300 um; and
    wherein another configuration is a closed configuration in which the average spacing between the sample contact areas of the plates is 200 μm or less.

The method or device of any prior embodiment, wherein the capture agents and the second agents are separated by a distance that is at least 2 times less than the average spacing between the sample contact area of the two plates.

The method or device of any prior embodiment, wherein the capture agents and the second agents are separated by a distance that is at least 2 times, 3 times, 5 times, 10 times, 20 times, 30 times, 50 times, 100 times, 200 times, 300 times, 500 times, 1000 times, 2000 times, 5000 times, 10000 times, 5000 times, less than the average spacing between the sample contact area of the two plates, or in a range of any two values.

The method or device of any prior embodiment, wherein the signal related to the analyte captured by the capture agent are the signals coming from (i) the analyte captured by the capture agent, (ii) the label attached an analyte that is captured by the binding site, or (iii) both (i) and (ii).

The method or device of any prior embodiment, wherein one or both of the sample contact areas comprise spacers, wherein the spacers regulate the spacing between the sample contact areas of the plates when the plates are in the closed configuration.

The method of any prior embodiment, wherein the spacing between the sample contact areas when the plates are in a closed configuration is regulated by spacers.

The device of any prior embodiment, wherein the device further comprises spacers that regulate the spacing between the sample contact areas when the plates are in a closed configuration.

The method or device of any prior embodiment, wherein the storage site further comprises another reagent.

The method or device of any prior embodiment, wherein the binding site comprises, in addition to immobilized capture agent, another reagent that is, upon contacting the sample, capable of diffusion in the sample, The method or device of any prior embodiment, wherein the detection of the signal is electrical, optical, or both. (Will add more on the detection later. Fluorescence, SPR, etc.).

The method or device of any prior embodiment, wherein the sample is a blood sample (whole blood, plasma, or serum).

The method or device of any prior embodiment, wherein the material of fluorescent microsphere is dielectric, (e.g. SiO2, Polystyrene,) or the combination of dielectric materials thereof.

The method or device of any prior embodiment, which comprises steps of adding the detection agent of said fluorescence label to the first plate to bind competitive agent.

The method or device of any prior embodiment, which comprises steps of washing after the detection agent is added.

G. QMAX Assay with Textured Light Scattering Surface
Another aspect of the present invention provides a device for enhancing optical signal in assaying a thin sample layer.

In some embodiments, the device comprises:
  a first plate, a second plate, spacers, and a light scattering layer, wherein:
    i. the first and second plates are movable relative to each other into different configurations, and have, on its respective inner surface, a sample contact area for contacting a sample that contains an analyte;
    ii. one or both of the plates are flexible;
    iii. the first plate is transparent to the light, and
    iv. the second plate substantially reflect light and comprises an inner surface a light scattering layer that has a rough topology;
  wherein one of the configurations is an open configuration, in which the average spacing between the inner surfaces of the two plates is at least 200 um, and the sample is deposited on one or both of the plates;
  wherein another of the configurations is a close configuration, which is configured after the sample deposition in the open configuration, and in the closed configuration: at least part of the sample is between the two plates and the average spacing between the inner surfaces of the plates is less than 200 um; and wherein in the closed configuration, the light scattering layer enhances trapping a probe light between the inner surface of the two plates.

In some embodiments, in the device, the light scattering surface of the second plate comprises:
i. the textured surface can be, but is not limited to a bumpy, wavy roughly surface;
ii. the textured surface can be periodic or aperiodic;
iii. the textured surface's average roughness range is preferred to be, but is not limited to 2 um-5 um; or
iv. the spacers are fixed to the inner surface of the first plate and have a predetermined uniform height;

B. Assay Improvement (II)
Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

One embodiment of the method of CROF, comprises:
(a) obtaining a sample, that is flowable;
(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;
(c) depositing, when the plates are configured in an open configuration, the sample on one or both of the plates; wherein the open configuration is a configuration in which the two plates are either partially or completely separated apart and the spacing between the plates is not regulated by the spacers; and
(d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average.).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

A. Testing System with QMAX Device

One aspect of the present invention provides systems and methods of analyzing a bio/chemical sample using QMAX device.

AA1. A method for analyzing a sample, comprising:
a) depositing a sample on a Q-card and closing the Q-card;
b) inserting the closed Q-card into an adaptor that connects to a camera of a handheld mobile communication device;
c) taking image(s) of the closed Q-card using the camera of the handheld mobile communication device;
d) transmitting, to a remote location, the image(s) and/or an analysis result of the images from the handheld mobile communication device;
e) analyzing, at the remote location, the image(s) and/or the analysis result transmitted from the mobile communication device; and
f) notifying a third party and/or the handheld mobile communication device if an anomaly is detected;
wherein the Q-card comprises two plates that are movable relative to each other and have an open configuration and a closed configuration;
wherein the sample is deposited on one or both plates of the Q-Card at the open configuration, and at the closed configuration at least a part of the sample is between the two plates,
wherein the mobile communication device is configured to produce an image of the Q card in the adaptor and transmit the image and/or an analysis result of the same to a remote location.

AA2. The method of any prior embodiment, wherein the sample deposited onto the Q-card is from a subject, and the subject performs step a).

AA3. The method of any prior embodiment, wherein the anomaly is identified if the analysis result of the sample is not within a normal range.

AA4. The method of any prior embodiment, wherein the anomaly is identified if the analysis results produced by the remote device and the mobile handheld communication device differ by a pre-defined value.

AA5. The method of any prior embodiment, wherein the sample comprises a body fluid selected from the group consisting of: amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

AA6. The method of any prior embodiment, wherein the sample comprises an environmental specimen that is obtained from: river, lake, pond, ocean, glaciers, icebergs, rain, snow, sewage, reservoirs, tap water, drinking water, soil, compost, sand, rocks, concrete, wood, brick, sewage; air, heat vents, industrial exhaust, or vehicular exhaust.

AA7. The method of any prior embodiment, wherein the sample comprises a foodstuff specimen that includes: raw food ingredients, cooked or processed food, plant and animal sources of food, preprocessed food, or fully processed food.

AA8. The method of any prior embodiment, wherein, in step (a), the Q-card is pressed by human hand.

AA9. The method of any prior embodiment, wherein step e) comprises comparing the result to a threshold or normal range to identify samples that contain an anomaly.

AA10. The method of any prior embodiment, wherein the method further comprises updating the handheld mobile communication device if the analysis at the remote location produces a result that is significantly different.

AA11. The method of any prior embodiment, wherein the sample deposited onto the Q-card is from a subject, and the analysis result is not transmitted to the subject.

AA12. The method of any prior embodiment, wherein the third party is a medical professional.

AA13. The method of embodiment AA12, wherein the medical professional is a doctor or nurse practitioner.

AA14. The method of any of embodiments AA1-AA12, wherein third party is an insurance company.

AA15. The method of any prior embodiment, wherein the result from the mobile communication device and/or the result from the remote location are sent to an emergency room.

AA16. The method of embodiment AA1, wherein, based on the results, the handheld mobile communication device or the remote location transmits follow-up information to the subject.

AA17. The method of embodiment AA16, wherein the follow-up information comprises an explanation of the result, education about a disease or condition, information related to a possible treatment, information on the location of a suitable physician, information related to change of diet and/or exercises, or an advertisement.

AA18. The method of any prior embodiment, wherein the Q-card comprises spacers that have a substantially uniform height and a predetermined constant inter spacer distance, and in the closed configuration: at least part of the sample is compressed by the two plates of the Q-card into a layer of highly uniform thickness and is substantially stagnant relative to the plates, wherein the uniform thickness of the layer is confined by the inner surfaces of the two plates and is regulated by the plates and the spacers.

AA19. The method of embodiment AA18, wherein at least one of the plates is flexible.

AA20. The method of embodiment AA19, wherein for the flexible plate, the thickness of the flexible plate times the Young's modulus of the flexible plate is in the range 60 to 750 GPa-um.

AA21. The method of embodiment AA19, wherein for the flexible plate, the fourth power of the inter-spacer-distance (ISD) divided by the thickness of the flexible plate (h) and the Young's modulus (E) of the flexible plate, ISD4/(hE), is equal to or less than 106 um3/GPa, AA22. The method of embodiment AA18, wherein spacers regulating the layer of uniform thickness have a filling factor of at least 1%, wherein the filling factor is the ratio of the spacer area in contact with the layer of uniform thickness to the total plate area in contact with the layer of uniform thickness.

AA23. The method of embodiment AA18, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness..

AA24. The method of any prior embodiment, wherein one or both plates comprises a location marker, either on a surface of or inside the plate, that provide information of a location of the plate.

AA25. The method of any prior embodiment, wherein one or both plates comprises a scale marker, either on a surface of or inside the plate, that provide information of a lateral dimension of a structure of the sample and/or the plate.

AA26. The method of any prior embodiment, wherein one or both plates comprises an imaging marker, either on surface of or inside the plate, that assists an imaging of the sample.

AA27. The method of embodiment AA18, wherein the spacers functions as a location marker, a scale marker, an imaging marker, or any combination of thereof.

AA28. The method of embodiment AA18, wherein the average thickness of the layer of uniform thickness is in the range of 0.2 μm to 3.8 μm and the sample is blood.

AA29. The method of embodiment AA18, wherein the inter-spacer distance is in the range of 7 μm to 50 μm.

AA30. The method of embodiment AA18, wherein the inter-spacer distance is in the range of 50 μm to 120 μm.

AA31. The method of embodiment AA18, wherein the inter-spacer distance is in the range of 120 μm to 200 μm.

AA32. The method of embodiment AA18, wherein the inter-spacer distance is substantially periodic.

AA33. The method of embodiment AA18, wherein the spacers are pillars with a cross sectional shape selected from round, polygonal, circular, square, rectangular, oval, elliptical, or any combination of the same.

AA34. The method of embodiment AA18, wherein the spacers have are pillar shape and have a substantially flat top surface, wherein, for each spacer, the ratio of the lateral dimension of the spacer to its height is at least 1.

AA35. The method of embodiment AA18, wherein each spacer has the ratio of the lateral dimension of the spacer to its height is at least 1.

AA36. The method of embodiment AA18, wherein the minimum lateral dimension of spacer is less than or substantially equal to the minimum dimension of an analyte in the sample.

AA37. The method of embodiment AA18, wherein the minimum lateral dimension of spacer is in the range of 0.5 um to 100 um.

AA38. The method of embodiment AA18, wherein the spacers have a pillar shape, and the sidewall corners of the spacers have a round shape with a radius of curverture at least 1 μm.

AA39. The method of embodiment AA18, wherein the spacers have a density of at least 1000/mm2.

AA40. The method of any prior embodiment, wherein at least one of the plates is transparent.

AA41. The method of any prior embodiment, wherein at least one of the plates is made from a flexible polymer.

AA42. The method of embodiment AA18, wherein, for a pressure that compresses the plates, the spacers are not compressible and/or, independently, only one of the plates is flexible.

AA43. The method of any prior embodiment, wherein the flexible plate has a thickness in the range of 10 um to 200 um.

AA44. The method of embodiment AA18, wherein the variation of the uniform thickness is less than 30%.

AA45. The method of embodiment AA18, wherein the variation of the uniform thickness is less than 10%.

AA46. The method of embodiment AA18, wherein the variation of the uniform thickness is less than 5%.

AA47. The method of any prior embodiment, wherein the plates are connected by a hinge and are configured to be changed from the open configuration to the closed configuration by folding the plates along the hinge.

AA48. The method of any prior embodiment, wherein the layer of uniform thickness sample is uniform over a lateral area that is at least 1 mm2.

AB1. A system for analyzing a sample, comprising:
  a) a Q-card for manipulating a sample for analysis comprising two plates that are movable relative to each other and have an open configuration and a closed configuration; b) a handheld mobile communication device that comprises a camera;
  c) an adaptor having a slot that is configured to hold a closed Q-Card, wherein the adaptor connects to the handheld mobile communication device and permits the camera to take an image of closed Q-Card; and
  d) a remote device that is capable of storing information and communicating with the mobile communication device;
    wherein the sample is deposited on one or both plates of the Q-Card at the open configuration, and at the closed configuration at least a part of the sample is between the two plates,
    wherein the system is configured to produce an image of the Q card in the adaptor and transmit the image and/or an analysis result of the same to a remote location.

AB2. The system of embodiment AB1, wherein the Q-card can be placed in the closed configuration by folding.

AB3. The system of embodiment AB1, wherein the remote device is configured to analyze the image and/or the analysis result of the same.

AB4. The system of embodiment AB1, wherein the remote device is configured to communicate with other remote devices.

AB5. The system of embodiment AB1, wherein the remote device is configured to notify a third if an anomaly in a sample placed in the Q card is detected.

AC1. A method for providing healthcare recommendations to a subject, comprising:
  a) using Q-cards and an associated mobile communication device to analyze one or a plurality of analytes in samples from a subject;
  b) transmitting, to a remote location, the analysis results of the analytes from the mobile communication device;
  c) storing the analysis results in a data set;

d) generating, at the remote location, a series of healthcare recommendations based on accumulated analysis results in the data set; and
e) providing the healthcare recommendations to the subject by sending messages to the mobile communication device;

wherein the healthcare recommendations comprise suggestions related to medicine, nutrition/diet, exercise, and/or treatment for the subject.

AC2. The method of paragraph AC1, further comprising identifying the subject's needs before providing the healthcare recommendations to the subject.

B. Cholesterol Testing with QMAX Device

Another aspect of the present invention provides devices and methods of cholesterol testing using QMAX device.

BA1. A method of analyzing a liquid sample, comprising:
(d) obtaining the liquid sample;
(e) obtaining a device, which comprises a first plate, a second plate, and spacers fixed on one or both of the plates; wherein:
 i. the plates are movable relative to each other into different configurations, including an open configuration and a closed configuration;
 ii. each plate respectively comprises an inner surface that has a sample contact area, and
 iii. the spacers have a predetermined substantially uniform height, and at least one of the spacers is inside the sample contact area;
(f) depositing the sample on one or both of the plates when the plates are in an open configuration,
 wherein in the open configuration the two plates are partially or entirely separated apart and the spacing between the plates is not regulated by the spacers; and
(g) after (c), bringing the two plates together and pressing the plates into a closed configuration,
 wherein in the closed configuration: at least part of the sample is compressed by the two plates into a layer of highly uniform thickness, which is confined by the inner surfaces of the two plates and is regulated by the spacers;
 wherein one or both sample contact surfaces comprise one or more storage sites that store one or more reagents, which are configured to dissolve and diffuse in the sample in the closed configuration, and react with cholesterol in the sample to produce or alter a luminescence signal;
(h) reading the luminescence signal from the layer of highly uniform thickness, thereby obtaining a measurement of total cholesterol in the sample.

BA2. The method of paragraph BA1, wherein the one or more reagents are configured to react with cholesterol to generate or alter a colormetric luminescence signal, wherein the reading step (e) comprises detecting and quantifying the colormetric luminescence signal from the analyte in the layer of highly uniform thickness.

BA3. The method of paragraph BA1, wherein the one or more reagents comprise cholesteryl ester hydrolase and cholesterol oxidase.

BA4. The method of paragraph BA3, wherein the one or more reagents further comprise peroxidase and a color probe.

BA5. The method of paragraph BA4, wherein the color probe comprises 4-aminophenazone and phenol.

BA6. The method of paragraph BA1, wherein the one or more storage sites comprise a first storage site located on the first plate and a second storage site located on the second plate.

BA7. The method of paragraph BA6, wherein:
 i. the first storage site comprises cholesteryl ester hydrolase and cholesterol oxidase; and
 ii. the second storage site comprises 4-aminophenazone, phenol and peroxidase.

C. Heavy Metal Testing

Another aspect of the present invention provides devices and methods of heavy metal testing in bio/chemical samples. More specifically, the invention provides a process for detecting heavy metal ions in an aqueous system, a device comprising the heavy metal ion test piece and a sensor. A portable test method provided by the device according to the invention, so as to detect the heavy metal ions in a convenient, efficient and rapid manner.

The heavy metal (ion) pollution refers to the environmental pollution caused by heavy metals or their compounds. The increase of the heavy metal content in the environment, especially in the case of heavy metal pollution in an aqueous system, is mainly due to human factors, such as mining, waste gas emission, sewage irrigation and the use of heavy metal-containing products, which results in the deterioration of environmental quality. Currently there is still a need for a heavy metal ion test piece which can be used to detect the small amount, even trace amount of heavy metal ions in an aqueous system in a simple, low cost, highly sensitive, highly reliable and stable manner. Meanwhile, it is required that the test piece is available for in situ detection, and is capable of detecting heavy metal ions with high sensitivity. Moreover, it is desired that the heavy metal ions can be not only qualitatively detected, but also quantitatively or semi-quantitatively detected. The current invention provides devices and methods for achieving these goals.

C-1. Devices and Methods for Heavy Metal Testing

Figure 5:
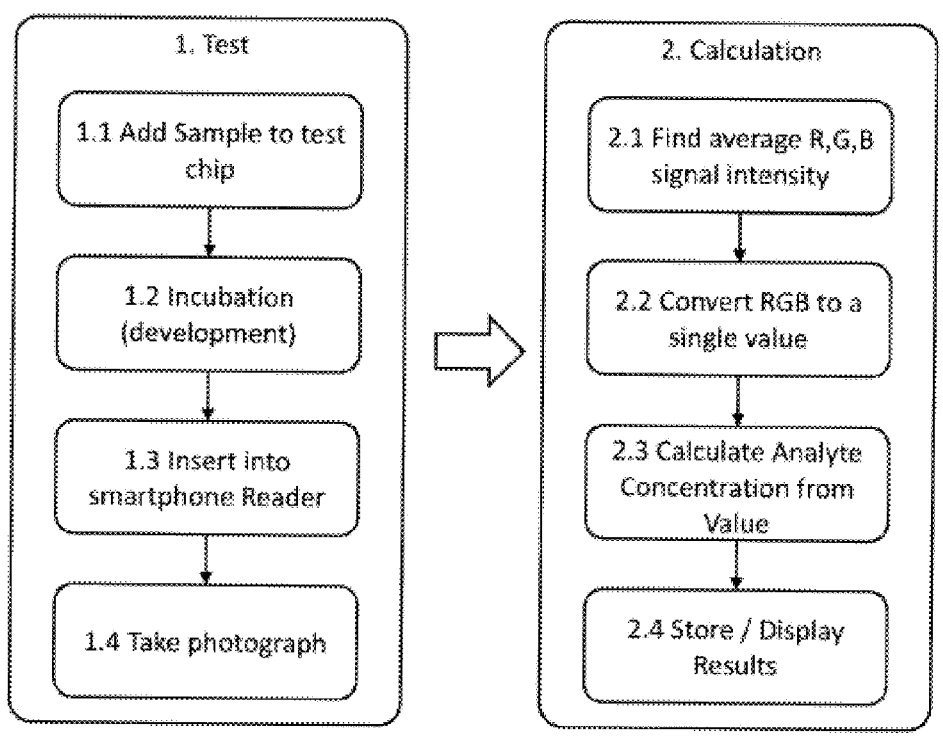
FIG. 5 A diagram of a process of testing heavy metal in water.

FIG. 5 shows that the invention comprises two parts: 1. Test, which comprises a test card that has dried reagent in a volume-controlled sample chamber, and can be inserted into a smartphone-based reader for measurement; 2. Calculation, which comprises a method to convert the photograph taken by smartphone and convert to signal for calculating analyte concentrations.

Figure 6:
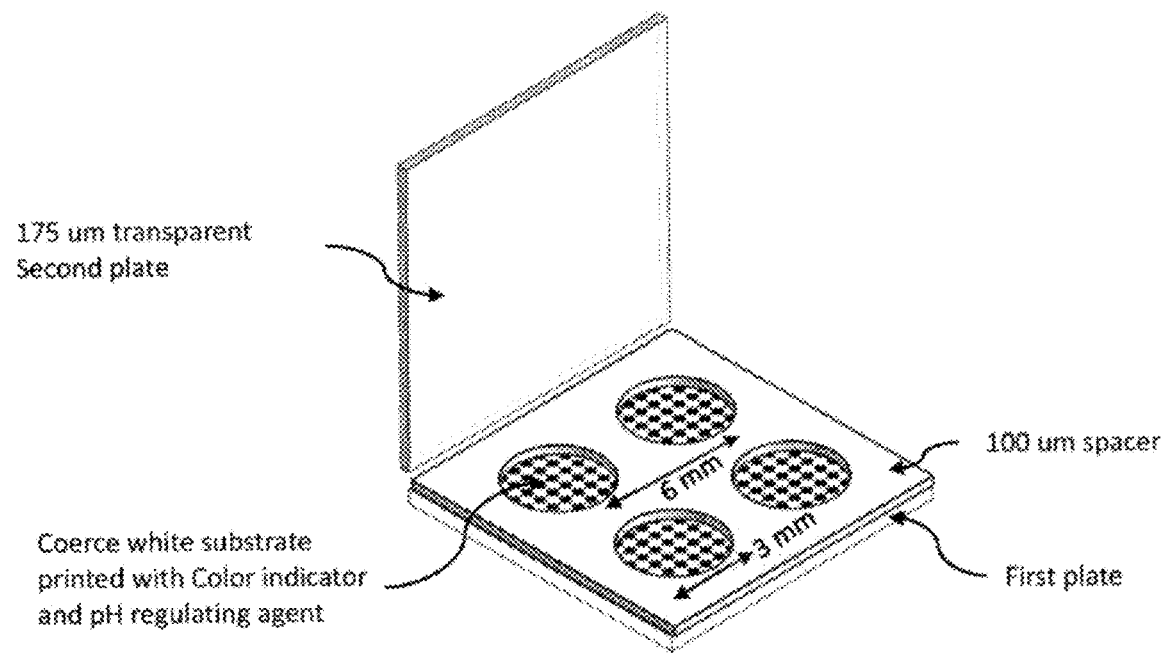
FIG. 6 Schematics of the Test plate used for heavy metal test.

As demonstrated by FIG. 5, This invention is a device and method for obtaining a point-of-collection, selected quantitative indicia of an analyte on a test platform, comprising:
1. providing a modular, colorimetric reactive test platform having a test region and calibration region;
2. providing an analyte to be tested on the test region of the modular, colorimetric test platform, wherein the test region is adapted to enable a colorimetric reaction to the analyte;
3. obtaining a color image of the test region containing the analyte and the calibration region;
4. selecting an array of pixels in each of the color images of the test region containing the analyte and the calibration region;
5. determining a median RGB color value for each of the arrays of pixels;
6. converting the median RGB color value for each of the arrays of pixels to a characteristic value;
7. providing a calibration indicia that relates a selected quantitative indicia of the characteristic value;
8. associating the characteristic value to determine the selected quantitative indicia of the analyte As shown in FIG. 6, a first plate, which is a coerce white substrate, is printed uniformly with color indicator as well as pH regulating agent. The color indicator is bio/chemical reagent that shows specific reaction to heavy metals in liquid sample. The liquid sample includes, but is not limited to, water, soil sample, oil, body fluid and food. In certain embodiments, the sample is drinking water. In certain embodiments, the sample is food. In some embodiments, the first plate is a coerce white polystyrene plate. In some embodiments, the color indicator is dried on the first plate. In some embodiments, the pH regulating agent is dried on the first plate. In some embodiments, the concentration of dried color indicator is 1 uM to 10 mM. In some embodiments, the concentration of dried pH regulating agent is 1 uM to 10 mM.

As shown in FIG. 6, the surface of the first plate facing the second plate is defined as the inner surface of the first plate; the surface of the second plate that faces the first plate are also defined as the inner surface of the second plate. In some embodiments, the inner surfaces of the respective plates comprise a sample contact area for contacting a sample that comprises an analyte. The sample contact area can occupy part or the entirety of the respective inner surface.

As shown in FIG. 6, for testing heavy metal in water using colorimetric tests, a pH regulating agent must add to the sample to adjust the pH level to optimum condition. This is because the chemical reaction rate of color indicator to heavy metal ions changes significantly at different pH level, which leads to large color variation within tests if the pH is unregulated. For heavy metal test, a pH regulating agent, or a combination of multiple combination of them, is dried on the plate for adjusting sample PH level includes, but is not limited to: Formic acid (methanoic acid), Oxalic acid (ethanedioic acid), Lactic acid (2-hydroxypropanoic acid), Malic acid (2-hydroxybutanedioic acid), Citric acid (2-hydroxypropane-1,2,3-tricarboxylic acid), Carbonic acid (hydroxymethanoic acid, not an IUPAC name), Aminomethylphosphonic acid.

As shown in FIG. 6, the second plate comprises spacers that are fixed on the inner surface of the second plate. It should be noted, however, that in some embodiments the spacers are fixed on the inner surface of the first plate and in other embodiments on the inner surfaces of both the second plate and the first plate As shown in FIG. 6, the spacer is between 1 um, 2 um, 5 um, 10 um, 20 um, 50 um, 100 um, 200 um, 500 um, 1000 um or in a range between any of the two values. The diameter of hole in the spacer is around 0.5 mm, 1 mm, 2 mm, 3 mm 4 mm, 5 mm, or in a range between any of the two values. The center-to-center spacing between holes is 1 mm, 2 mm, 3 mm, 4 mm, 5 mm, 6 mm, 7 mm, 8 mm, 9 mm, 10 mm, 20 mm, 50 mm, or in a range between any of the two values. The second plate is a transparent flat film, with thickness around 1 um, 2 um, 5 um, 10 um, 20 um, 50 um, 100 um, 200 um, 500 um, 1000 um or in a range between any of the two values.

As shown in FIG. 6, the first plate and the second plate are moveable relative to each other into different configuration. One of the configurations is an open configuration, in which the two plates are partially or entirely separated apart and the spacing between the plates are not regulated by the spacers. FIG. 5 shows the plates in the open configuration, in which a sample, such as but not limited to blood, can be added to first plate, the second plate, or both of the plates.

In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

As shown in FIG. 6 The second plate is a transparent thin film with smooth surface. It is necessary that the absorption of second plate does not interfere with the absorption of color indicator. Depends on the flexibility of the material, thickness from 10 um~300 um can be used as second plate, as long as no distortion of sample chamber will happen after second plate is pressed onto the sample.

Figure 7:
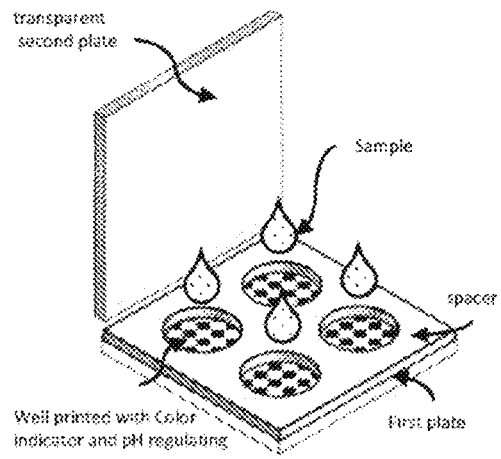
FIG. 7 Schematics of test procedure. 1. First, minute samples are added to each well printed with color indicator and pH regulating agent. 2. The transparent second plate is then pressed on top of the spacer to form a closed sample chamber. 3. Incubation to allow each individual sample to develop color.
Figure 7:
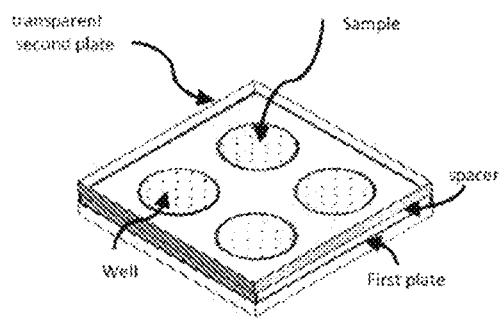
Figure 7:
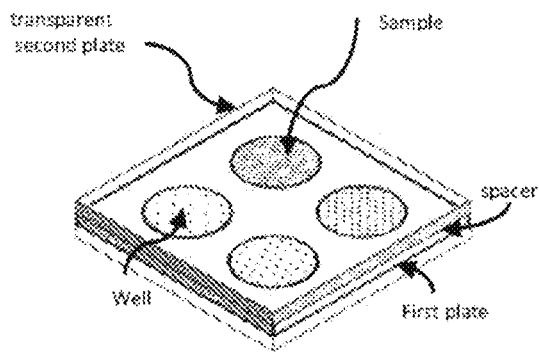

As shown in FIG. 7, a white polystyrene (PS) substrate printed with home-made color indicator and pH regulating agent. The color indicator and pH regulating agent amount on the sensing area is carefully controlled according to the dimension of the well, so that when each well is filled full with sample, the desired pH level and color indicator concentration can be achieved.

Depends on the type of heavy metal or their combinations, different chemicals are used as color indicator. Color Indicator can be: (1) For lead detection, the color indicator is 0.01%~0.2% Sodium Rhodizonate (preferable 0.2% after dissolved in sample), or (2) For Copper, Cadmium, Chromium, Mercury, 10 uM~1 mM Dithizone (preferable 30 uM after dissolved in sample)

As shown in FIG. 7, the printing parameter for Color Indicator agent can vary as long as uniform drying is achieved on the first plate. The printing conditions, i.e., droplet volume, speed, depends on the surface wetting property of the first plate, which is well-known to skilled person, thus do not require elucidation. In this invention, the printing condition is droplet diameter 500~600 um, pitch ~1 mm, print speed ~10 mm/sec.

As shown in FIG. 7, the well dimension is determined by dimensions of holes array on the spacer. The thickness of the spacer, the diameter of the holes and their spacing determines the sample volume. Their configuration is flexible but it is crucial to avoid distortion of sample chamber under certain configurations, i.e. small aspect ratio. Here, the thickness of the spacer can be 2 um~1 mm (preferably 100 um), and the well diameter can be 100 um~10 mm (preferably, 3 mm), and the center-to-center spacing can be 100 um~10 mm, (preferably, 6 mm).

As shown in FIG. 7, In some embodiments, the method of the present invention, after step (2) and before step (3), further comprise incubating the layer of uniform thickness for a predetermined period of time. In certain embodiments, the predetermined period of time is equal to or longer than the time needed for the detection antibody to diffuse into the sample across the layer of uniform thickness. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

Figure 8:
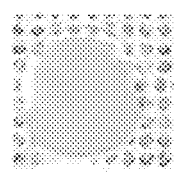
FIG. 8 A diagram of a chemical reaction that is used to test lead in water.
Figure 8:
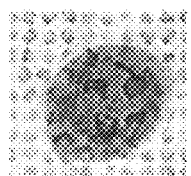
Figure 8:
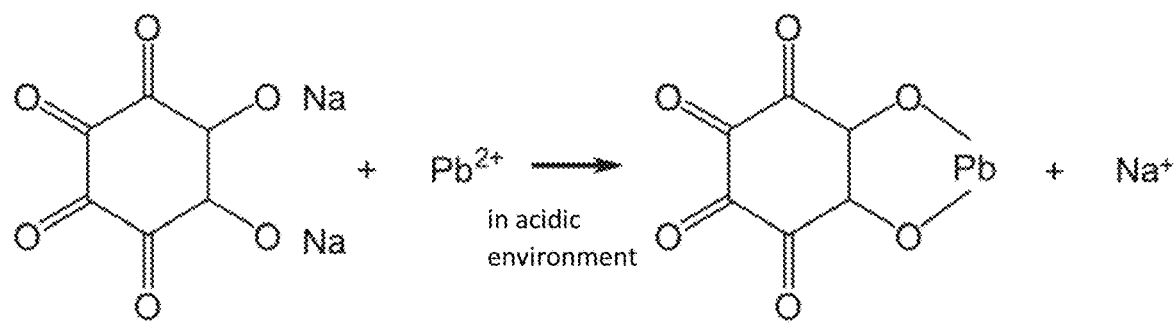

FIG. 8 shows the diagram of a chemical reaction that is used to test lead in water. The lead ion reacts with Sodium Rhodizonate (dark yellow color) dissolved in sample, which form a insoluable lead Rhodizonate that has a red-crimson color. The color absorption can be analyzed to calculate the lead concentration in water.

Figure 9:
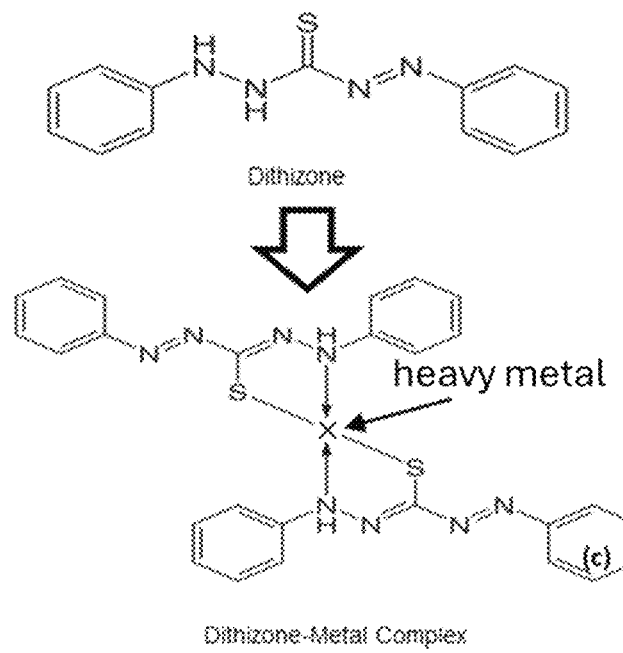
FIG. 9 A diagram of a chemical reaction that is used to test heavy metals in water.
Figure 9:
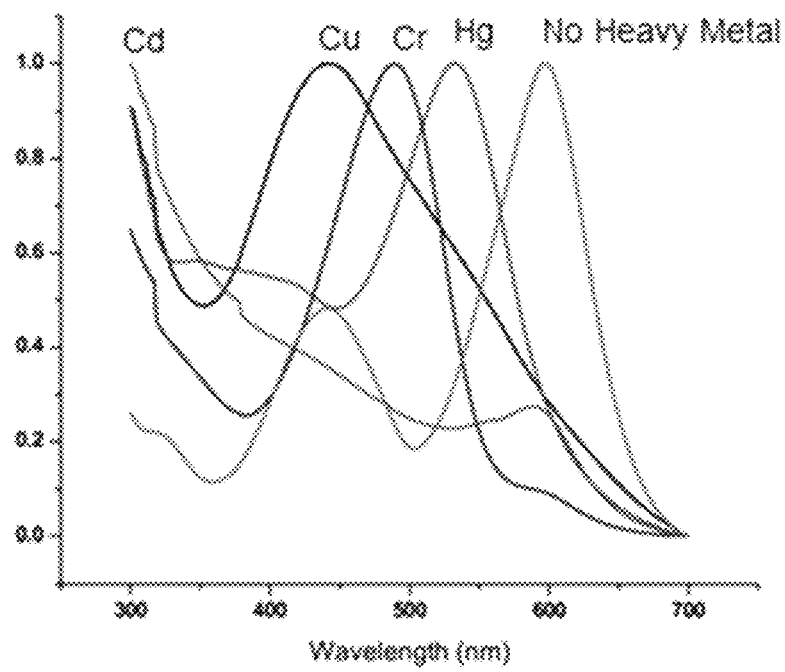

FIG. 9 A diagram of a chemical reaction that is used to test heavy metals in water. The heavy metals can be Cd, Cu, Cr, Hg. The heavy metal ion reacts with Dithiozone dissolved in sample, which form a Dithizone-Metal complex that yield a different color for different heavy metals. The color can be used to identify the type of heavy metals and the color absorption can be analyzed to calculate the heavy metal concentration in water.

Figure 10:
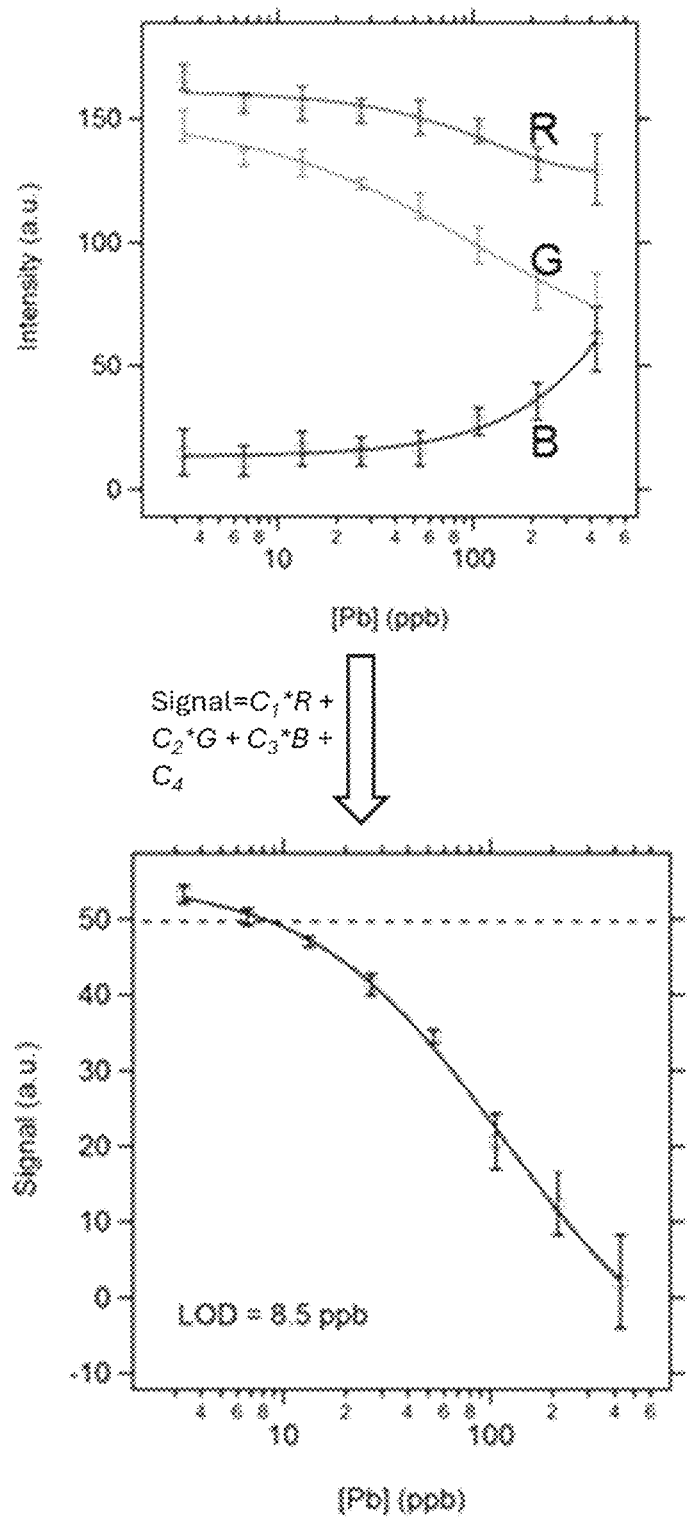
FIG. 10 A schematics of converting colorimetric Lead in water test standard curve of individual R, G, B channel to a single standard curve.

FIG. 10 shows schematics of converting colorimetric Lead in water test standard curve of individual R, G, B channel to a single standard curve. For each sample contains different concentration of heavy metals, the R, G, B signal are different. A combination of R, G, B channel signal at different Lead concentration is used for this conversion. In some embodiment, the method of combination is linear combination. In some embodiment, the coefficient for combining RGB channel signal, is a constant. In some embodiment, the coefficient for combining RGB channel signal, is a matrix. In some embodiment, the coefficient for combining RGB channel signal, is a function of lead concentration in water.

Figure 11:
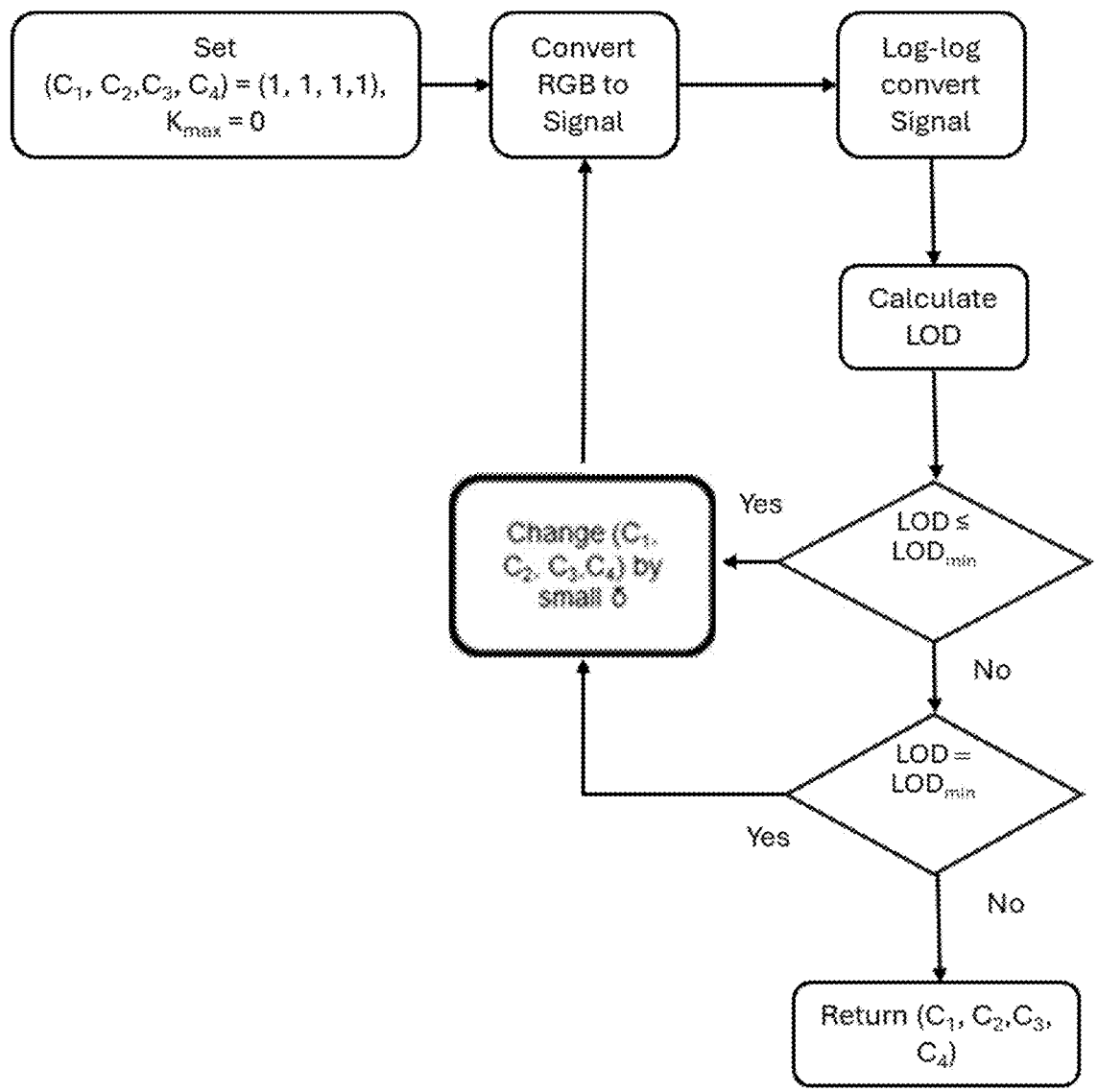
FIG. 11 A diagram of algorithm to converting standard curve of individual R, G, B channel to a single standard curve.

As shown in FIG. 11 the algorithm to converting standard curve of individual R, G, B channel to a single standard curve is a process to find the best coefficient of combing R, G, B signals so that best sensitivity of assay can be achieved. In some embodiment, a linear combination of R, G, B channel signal at different Lead concentration is used for this conversion.

In some embodiment, the linear coefficient is trained using a Generalized Reduced Gradient Algorithm. Such algorithm is open source and known to skilled person and does not require elucidation. Here, the process of this algorithm is shown in a diagram, briefly:

1. First, we define 4 constant: C1, C2, C3, and C4 so that $$Signal = C_1 * R + C_2 G + C_3 * B + C_4$$

2. Change the linear coefficient by a small amount with pre-defined amount
3. Calculate the limit of detection (LOD),
4. keep changing the linear coefficient until the minimum LOD can be achieved In this invention, we trained the data using 48 different tests. It is expected that the precision can be further improved with more training data. This well known among skilled person and does not require further elucidation.

C-2. Example: Test Lead Concentration in Tap Water

As an example, we Prepare a chip for testing lead in water. On a white coerce PS substrate we printed with home-made color indicator. The color Indicator is 0.2% Sodium Rhodizonate (this is the saturated concentration) and the pH regulating agent is pH ~3.0 by adding citric acid (this pH was optimized by our own experiment). We printed the reagent mixture with a parameter of droplet diameter 500~600 um, pitch ~1 mm and Print speed ~10 mm/sec.

For this example, we fabricated a plate, each plate has 48 wells, well diameter is 3 mm Center-to-center distance is 6 mm, well height is ~100 um (controlled using double-sided tape from Adhesive Research). We then drop 0.7 uL of sample in each well. Then we cover the well using 175 um thick PET film and wait for 1 min. Each well is immediately measured after 1 min incubation. For the test, the light source used is the smartphone camera flash light. And the image is taken using the smartphone's camera.

As assay validation, we calculate 4 key performances: 1. Limit of Detection (LOD) of each plate; 2. Intra-assay CV % of each plate, 3. Inter-assay CV % of each test day, and 4. Day-to-day CV %. For this example we prepared a total of 8 plates, each prepared at a different time using different batch of reagent. We perform the test on 2 different days and, for each day, we perform the tests on 4 different plates. On each plates, we perform the assay with 8 different concentration from 417 ppb, 213 ppb, 106 ppb, 53.4 ppb, 26.7 ppb, 13.3 ppb, 6.7 ppb and 0 ppb. For each concentration, we perform 6 replicates.

Figure 12:
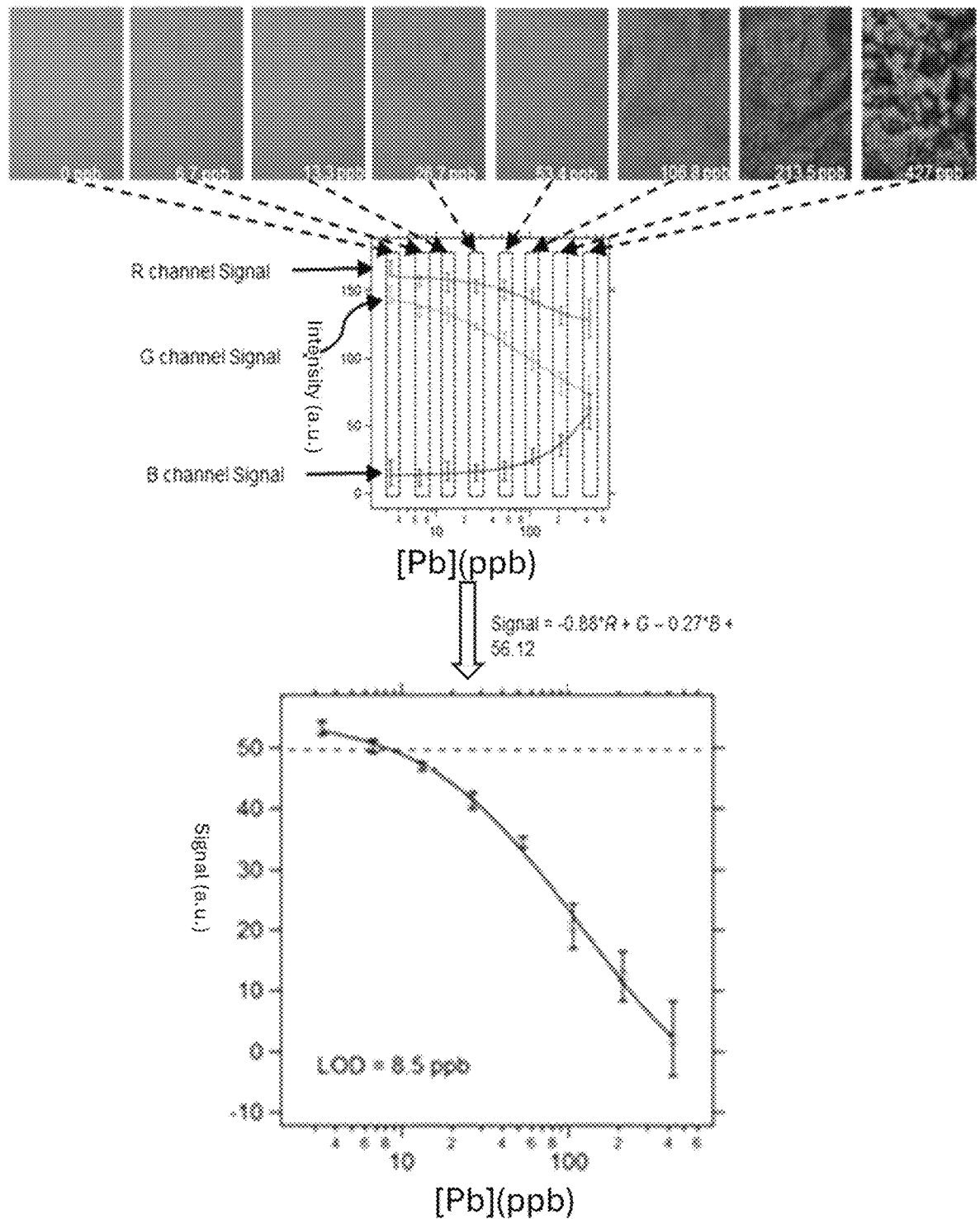
FIG. 12 An example of colorimetric Lead in water test standard curve of individual R, G, B channel converting to single standard curve and fitted with 5-PL logistic fitting.

FIG. 12 shows the Lead in water test standard curve of individual R, G, B channel. RGB channel signals changes with $Pb^{2+}$ concentration Curve and converted to a single standard curve using a conversion euqation Signal=−0.88*R+G−0.27*B+56.12. The converted data is fitted with 5PL logistic fitting. Error bar is Standard deviation of 6 replicate wells. The LOD, after conversion is 8.5 ppb.

Figure 13:
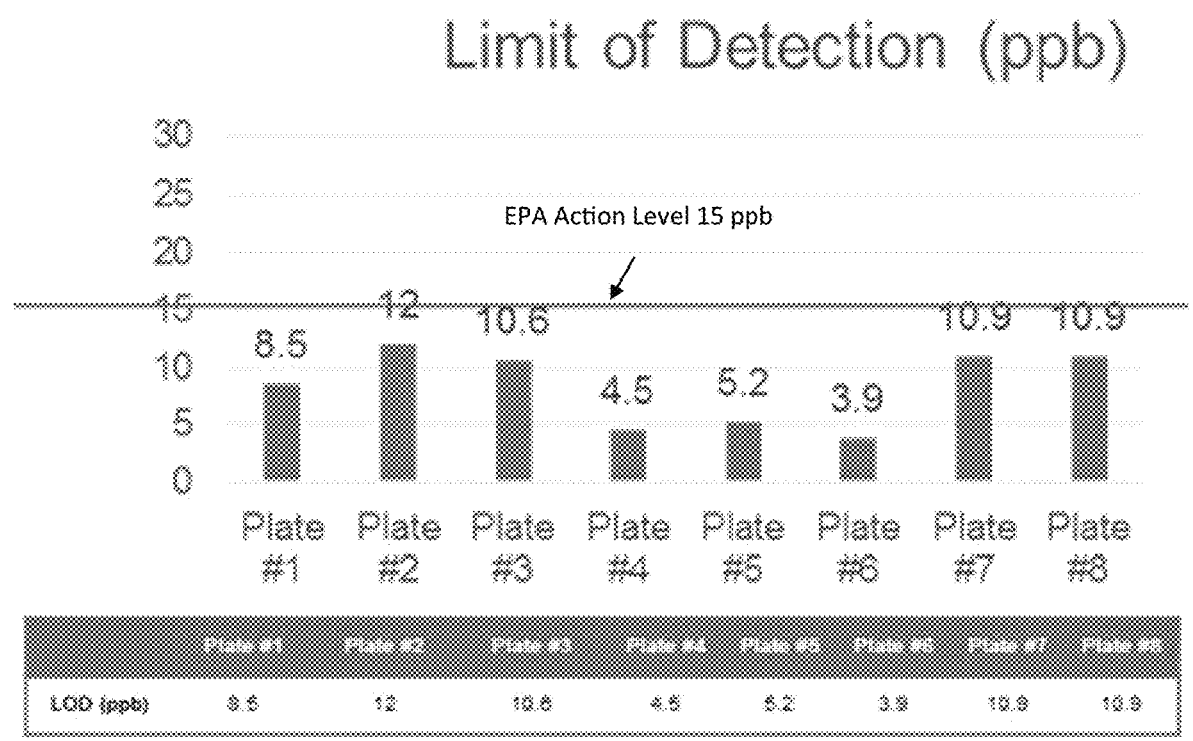
FIG. 13 An example of colorimetric Lead in water sensitivity of 8 different test plate.

FIG. 13 shows the sensitivity of all 8 different test plates in this example of the invention. Each test plate is prepared separately with different reagent and tested at different time. The average LOD achieved is 8 ppb, which is below the EPA action level at 15 ppb.

Figures 14, 15:
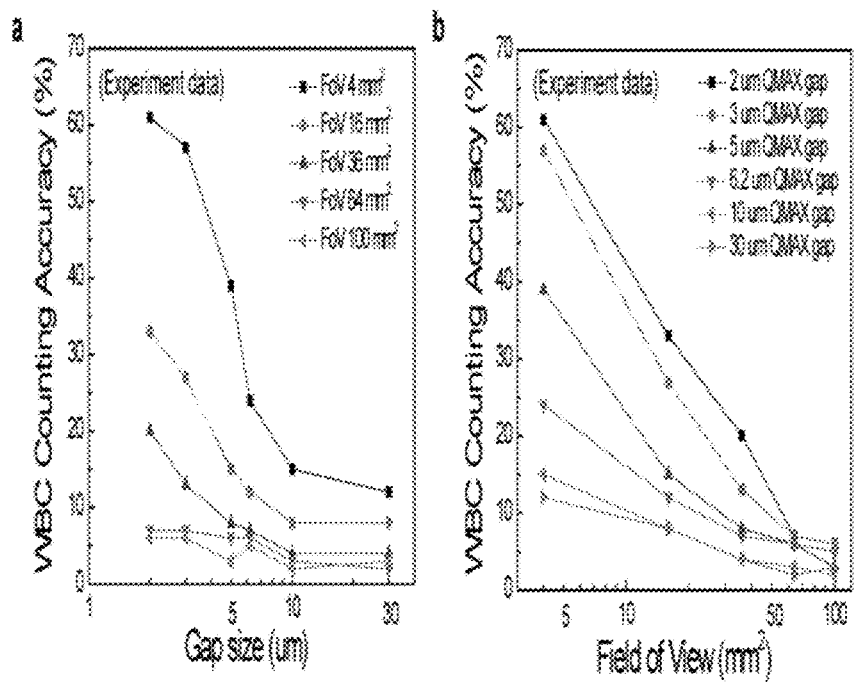
FIG. 14 Table of Intra-assay, Inter Assay and Day-to-day CV % of lead in water test.
FIG. 15 shows experimental observation of WBC counting accuracy vs. FoV vs. QMAX device gap.

FIG. 14 Table of Intra-assay, Inter Assay and Day-to-day CV % of lead in water test. Near LOD, of each tests, the Intra-assay CV %~4%, the Inter-assay CV %~4% and the Day-to-day CV %~1.1%

In summary, this example shows a test of lead concentration in tap water that shows (1) Sensitivity: average LOD~8 ppb. All test plates show LOD that meets EPA standard (15 ppb), with the best LOD achieved is 3.9 ppb. (2) Repeatability: Intra-assay CV % at LOD~4%, Inter-assay CV % at LOD~4% and Day-to-day CV % at LOD~1.1%

D Foodstuff Safety and Allergen Test Using QMAX Device

Another aspect of the present invention provides devices and methods for safety and allergen test in foodstuff samples.

As summarized above, the devices, systems and methods in the present invention may find use in analyzing a foodstuff sample, e.g., a sample from raw food, processed food, cooked food, drinking water, etc., for the presence of foodstuff markers. A foodstuff marker may be any suitable marker, such as those shown in Table B9, below, that can be captured by a capturing agent that specifically binds the foodstuff marker in a CROF device configured with the capturing agent. The environmental sample may be obtained from any suitable source, such as tap water, drinking water, prepared food, processed food or raw food, etc. In some embodiments, the presence or absence, or the quantitative level of the foodstuff marker in the sample may be indicative of the safety or harmfulness to a subject if the food stuff is consumed. In some embodiments, the foodstuff marker is a substance derived from a pathogenic or microbial organism that is indicative of the presence of the organism in the foodstuff from which the sample was obtained. In some embodiments, the foodstuff marker is a toxic or harmful substance if consumed by a subject. In some embodiments, the foodstuff marker is a bioactive compound that may unintentionally or unexpectedly alter the physiology if consumed by the subject. In some embodiments, the foodstuff marker is indicative of the manner in which the foodstuff was obtained (grown, procured, caught, harvested, processed, cooked, etc.). In some embodiments, the foodstuff marker is indicative of the nutritional content of the foodstuff. In some embodiments, the foodstuff marker is an allergen that may induce an allergic reaction if the foodstuff from which the sample is obtained is consumed by a subject.

In some embodiments, the devices, systems and methods in the present invention further includes receiving or providing a report that indicates the safety or harmfulness for a subject to consume the food stuff from which the sample was obtained based on information including the measured level of the foodstuff marker. The information used to assess the safety of the foodstuff for consumption may include data other than the type and measured amount of the foodstuff marker. These other data may include any health condition associated with the consumer (allergies, pregnancy, chronic or acute diseases, current prescription medications, etc.).

The report may be generated by the device configured to read the CROF device, or may be generated at a remote location upon sending the data including the measured amount of the foodstuff marker. In some cases, a food safety expert may be at the remote location or have access to the data sent to the remote location, and may analyze or review the data to generate the report. The food safety expert may be a scientist or administrator at a governmental agency, such as the US Food and Drug Administration (FDA) or the CDC, a research institution, such as a university, or a private company. In certain embodiments, the food safety expert may send to the user instructions or recommendations based on the data transmitted by the device and/or analyzed at the remote location.

A list of foodstuff markers is available in Table D1. In some embodiments of the present invention, the QMAX device is used to detect the presence and/or quantity of analyte, including, but not limited to, the foodstuff markers listed in Table D1.

TABLE D1

Foodstuff Markers

| Source/Class | Marker/target |
|---|---|
| Pathogens/microbes | Bacillus anthracis (LF), Giardia lamblia, Legionella, Total Coliforms (including fecal coliform and E. Coli), Viruses (enteric) stapylococci (e.g., Staphylococcus epidermidis and Staphylococcus aureus (enterotoxin A, B, C, G, I, cells, TSST-1), Enterrococcus faecalis, Pseudomonas aeruginosa, Escherichia coli (Shiga-like toxin, F4, F5, H, K, O, bacteriophage K1, K5, K13), other gram-positive bacteria, and gram-negative bacilli. Clostridium difficile (Toxin A, B), Bacteroidetes, Cryptosporidium parvum (GP900, p68 or cryptopain, oocyst), Candida albicans, Bacillus anthracis, Bacillus stearothermophilus, Bacillus cereus, Bacillus licheniformis, Bacillus subtilis, Bacillus pumilus, Bacillus badius, Bacillus globigii, Salmonella typhimurium, Escherichia coli O157:H7, Norovirus, Listeria monocytogenes (internalin), Leptospira interrogans, Leptospira biflexa, Campylobacter jejuni, Campylobacter coli, Clostridium perfringens, Aspergillus flavus (aflatoxins), Aspergillus parasiticus (aflatoxins), Ebola virus (GP), Histoplasma capsulatum, Blastomyces dermatitidis (A antigen), Gram-positive bacteria (teichoic acid), Gram-ngative bacteria (such as Pseudomonas aeruginosa, Klebsiella pneumoniae, Salmonella enteriditis, Enterobacter aerogenes, Enterobacter hermanii, Yersinia enterocolitica and Shigella sonnei)(LPS), Polio virus, Influenza type A virus, Disease specific prion (PrP-d), Hepatitis A virus, Toxoplasma gondii, Vibrio cholera, Vibrio parahaemolyticus, Vibrio vulnificus, Enterococcus faecalis, Enterococcus faecium, Angiostrongylus Cantonensis, Cyclospora cayetanensis, Entamoeba histolytica, Trichinella spiralis, |
| Toxins/carcinogens | N-methylamino-L-alanine (BMAA), Clostridium botulinum neurotoxins, BoNT A, B, Ricin A, B; diphtheria toxin; Aristolochic acid; Colchicine, Ochratoxin A, Sterigmatocystin, Ergotamine, Fumonisins, Fusarin C, domoic acid, Brevetoxin, Mycotoxins, Antimony, Ciguatera fish poisoning, museinol, muscarine, psilocybin, coprius artemetrais, ibotenic acid, amanitin, Nitrite poisoning, Puffer fish (tetrodotoxin), histamine, amnesic, |
| Halogenated hydrocarbons | Heptachlor, chlordane |
| Heavy metals | Lead, mercury, cadmium, Chromium, Arsenic, Copper, Tin, Zinc, Thallium |
| Allergens | peanut (Ara h 1, Ara h 2, Ara h 6), fish, shellfish, mollusks, shrimp (D. pteronyssinus tropomyosin allergen, Der p 10) Cod (Gadc1); Atlantic salmon (Sals1); domestic cattle milk (Bosd4, Bosd5, Bosd6, Bosd7, Bosd8); chicken/egg (Gald1, Gald2, Gald3, Gald4, Gald5); shrimp (Mete1); shrimp (Pena1, Peni1); black tiger shrimp (Penm1, Penm2); squid (Todp1), brown garden snail (Helas1); abalone (Halm1); edible frog (Rane1, Rane2); oriental mustard (Braj1); rapeseed (Bran1); cabbage (Brao3); turnip (Brar1, Brar2); barley (Horv15, Horv16, Horv17, Horv21); rye (Secc20); wheat (Tria18, Tria19, Tria25, Tria26, gliadin); corn (Zeam14, Zeam25); rice (Orys1), celery (Apig1, Apig4, Apig5); carrot (Dauc1, Dauc4); hazelnut (Cora1.04, Cora2, Cora8); strawberry (Fraa1, Fraa3, Fraa4); apple (Mald1, Mald2, Mald3, Mald4); pear (Pyrc1, Pyrc4, Pyrc5); avocado (Persa1); apricot (Pruar1, Pruar3); sweet cherry (Pruav1, Pruav2, Pruav3, Pruav4); European plum (Prud3); almond (Prudu4); peach (Prup3, Prup4); asparagus (Aspao1); saffron crocus (Cros1, Cros2); lettuce (Lacs1); grape (Vitv1); banana (Musxp1); pineapple (Anac1, Anac2); lemon (Citl3); sweet orange (Cits1, Cits2, Cits3); litchi (Litc1); yellow mustard (Sina1); soybean (Glym1, Glym2, Glym3, Glym4); mung bean (Vigr1); peanut (Arah1, Arah2, Arah3, Arah4, Arah5, Arah6, Arah7, Arah8); lentil (Lenc1, Lenc2); pea (Piss1, Piss2); kiwi (Actc1, Actc2); bell pepper (Capa1w, Capa2); tomato (Lyce1, Lyce2, Lyce3); potato (Solat1, Solat2, Solat3, |

TABLE D1-continued

Foodstuff Markers

| Source/Class | Marker/target |
|---|---|
| | Solat4); Brazil nut (Bere1, Bere2); black walnut (Jugn1, Jugn2); English walnut (Jugr1, Jugr2, Jugr3); Cashew (Anao1, Anao2, Anao3); Castor bean (Ricc1); sesame (Sesi1, Sesi2, Sesi3, Sesi4, Sesi5, Sesi6); muskmelon (Cucm1, Cucm2, Cucm3); Chinese-date (Zizm1); *Anacardium occidentale* (Anao1.0101, Anao1.0102); *Apium graveolens* (Apig1.0101, Apig1.0201); *Daucus carota* (Dauc1.0101, Dauc1.0102, Dauc1.0103, Dauc1.0104, Dauc1.0105, Dauc1.0201); *Citrus sinensis* (Cits3.0101, Cits3.0102); *Glycine max* (Glym1.0101, Glym1.0102, Glym3.0101, Glym3.0102); *Lens culinaris* (Lenc1.0101, Lenc1.0102, Lenc1.0103); *Pisum sativum* (Piss1.0101, Piss1.0102); *Lycopersicon esculentum* (Lyce2.0101, Lyce2.0102); *Fragaria ananassa* (Fraa3.0101, Fraa3.0102, Fraa3.0201, Fraa3.0202, Fraa3.0203, Fraa3.0204, Fraa3.0301); *Malus domestica* (Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302); *Prunus avium* (Pruav1.0101, Pruav1.0201, Pruav1.0202, Pruav1.0203); and *Prunus persica* (Prup4.0101, Prup4.0201) |
| Synthetic hormone analogues | 17beta-estradiol (E2), estrone (EI), estrogen (ES: EI + E2 + estradiol (E3)), 1 7alfa-ethynylestradiol (EE2), 4-nonylphenpol, testosterone, Diethylstilbestrol (DES), recombinant bovine growth hormone (rBGH) |
| Pesticides | Dieldrin, carbaryl, chlorpyrifos, parathion, aldrin, endosulfan I, endrin, toxaphene, O-ethyl O-4-nitrophenyl phenylphosphono-thioate (EPN), fenitrothion, pirimiphos-methyl, thiabendazole, methiocarb, Carbendazim, deltamethrin, Avermectin, Carbaryl, Cyanazine, Kresoxim, resmethrin, kadethrin, cyhalothrin, biphenthrin, fenpropathrin, allethrin and tralomethrin; aromatic-substituted alkanecarboxylic acid esters such as fenvarerate, flucythrinate, fluvalinate and cycloprothrin; and non-ester compounds such as etofenprox, halfenprox (MTI-732), 1-(3-phenoxyphenyl)-4-(4-ethoxyphenyl)-4-methylpentane (MTI-790), 1-(3-phenoxy-4-fluorophenyl)-4-(4-ethoxyphenyl)-4-methylpentane (MTI-800), dimethyl-(4-ethoxyphenyl)-(3-phenoxybenzyloxy)silane (SSI-116), silafluofen and PP-682, carbofuran, triazophos |
| Herbicide | atrazine, deethylatrazine, cyanazine, terbuthylazine, terbutryn, molinate, simazine, prometon, promteryn, hydroxyatrazine, 2,6-dichlorobenzamide (BAM), N-dealkylated triazines, mecoprop, thiram, acetochlor, alachlor, Chlorothalonil, Chlorsulfuron, Fenoxaprop ethyl, Linuron, monuron, diuron, Quizalofop-ethyl, Imazalil, Iprodione, Iprovalicarb, Myclobutanil |
| Industrial material/waste | Dioxin (2,3,7,8-TCDD), 4-tert-octylphenol, bisphenol A (BPA), Styrene, Di(2-ethylhexyl) phthalate, Dibutyl phthalate (DBP), benzophenone, benzene, trichloroethylene, polychlorinated biphenyl (PCB), nonylphenol, p-cresol, melamine, xylene, Sodium Fluoride |
| Antibiotics | 3-Amino-5-morpholinomethyl-2-oxazolidone (AMOZ; tissue bound metabolite of furaltadone), oxytetracycline, rolitetracycline, Actinomycin D, Amikacin sulfate, Aminoglycosides, nitrofuran (AOZ), Chloramphenicol, Doxycycline, Streptomycin, gentamicin, neomycin, kanamycin, sulfamethazine, enrofloxacin, sulfadiazine, enrofloxacin |
| Food coloring/additive/preservative | Tartrazine, ethoxyquin, erythritol, penicillin, Fluoroquinolone, Malachite Green/Leucomalachite Green, C.I. Solvent Yellow 14 (Sudan I), |
| Food preparation | Acrylamide, 2-amino-3-methylimidazo(4,5-f)quinolone, Benzo[a]pyrene |
| Nutritional content | Vitamins A (retinol), B12 (cobalmins), B6 (pyridoxine), B1 (thiamin), B2 (riboflavin), B3 (niacin), B5 (D-pantothenic acid), B7 (biotin), B9 (folic acid), C, D, E (alpha-tocopherol); |
| Other | Caffeine, Ovine myofibril proteins, Etodolac |

C. Assay, Particularly for Blood Tests (II)

Among other things, the present invention provides devices, systems, and methods of performing biological and chemical assays using a QMAX card. The exemplary embodiments herein disclosed are combined with the bio/chemical assays including, but not limited to, the assays as disclosed, described, and/or referred to in the following applications:

PCT Application No. PCT/US2016/045437, which was filed on Aug. 10, 2016,

PCT Application No. PCT/US2016/051775, which was filed on Sep. 14, 2016,

PCT Application No. PCT/US2016/051794, which was filed on Sep. 14, 2016,

U.S. Provisional Application No. 62/369,181, which was filed on Jul. 31, 2016,

U.S. Provisional Application No. 62/412,006, which was filed on Oct. 24, 2016,
U.S. Provisional Application No. 62/437,339, which was filed on Dec. 21, 2016,
U.S. Provisional Application No. 62/431,639, which was filed on Dec. 9, 2016,
U.S. Provisional Application No. 62/456,065, which was filed on Feb. 7, 2017,
U.S. Provisional Application No. 62/456,488, which was filed on Feb. 8, 2017,
U.S. Provisional Application No. 62/456,287, which was filed on Feb. 8, 2017,
U.S. Provisional Application No. 62/456,528, which was filed on Feb. 8, 2017,
U.S. Provisional Application No. 62/456,537, which was filed on Feb. 8, 2017,
U.S. Provisional Application No. 62/456,612, which was filed on Feb. 8, 2017,
U.S. Provisional Application No. 62/456,631, which was filed on Feb. 8, 2017,
U.S. Provisional Application No. 62/456,596, which was filed on Feb. 8, 2017,
U.S. Provisional Application No. 62/456,590, which was filed on Feb. 8, 2017,
U.S. Provisional Application No. 62/456,638, which was filed on Feb. 8, 2017,
U.S. Provisional Application No. 62/456,598, which was filed on Feb. 8, 2017,
U.S. Provisional Application No. 62/456,552, which was filed on Feb. 8, 2017,
U.S. Provisional Application No. 62/456,603, which was filed on Feb. 8, 2017,
U.S. Provisional Application No. 62/456,585, which was filed on Feb. 8, 2017,
U.S. Provisional Application No. 62/456,628, which was filed on Feb. 8, 2017,
U.S. Provisional Application No. 62/456,504, which was filed on Feb. 8, 2017,
U.S. Provisional Application No. 62/456,988, which was filed on Feb. 9, 2017,
U.S. Provisional Application No. 62/457,084, which was filed on Feb. 9, 2017,
U.S. Provisional Application No. 62/457,031, which was filed on Feb. 9, 2017,
U.S. Provisional Application No. 62/456,904, which was filed on Feb. 9, 2017,
U.S. Provisional Application No. 62/457,075, which was filed on Feb. 9, 2017,
U.S. Provisional Application No. 62/457,009, which was filed on Feb. 9, 2017,
U.S. Provisional Application No. 62/457,133, which was filed on Feb. 9, 2017,
U.S. Provisional Application No. 62/457,103, which was filed on Feb. 9, 2017,
U.S. Provisional Application No. 62/459,267, which was filed on Feb. 15, 2017,
U.S. Provisional Application No. 62/459,303, which was filed on Feb. 15, 2017,
U.S. Provisional Application No. 62/459,337, which was filed on Feb. 15, 2017,
U.S. Provisional Application No. 62/459,232, which was filed on Feb. 15, 2017, and
U.S. Provisional Application No. 62/459,160, which was filed on Feb. 15, 2017,
which are all hereby incorporated in reference by their entireties.

The embodiments in these applications herein incorporated can be regarded in combination with one another or as a single invention, rather than as discrete and independent filings.

Moreover, the exemplary embodiments disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in the aforementioned applications, all of which are hereby incorporated in reference by their entireties.

Exemplary Embodiments for Using a Gap 1.8 to 3.8 um

A1. A device for manipulating and analyzing a thin fluidic sample layer, comprising:
  a first plate, a second plate, and spacers, wherein:
    ix. the plates are movable relative to each other into different configurations;
    x. one or both plates are flexible;
    xi. each of the plates comprises an inner surface that has a sample contact area for contacting a fluidic sample;
    xii. each of the plates comprises, on its respective outer surface, a force area for applying an pressing force that forces the plates together;
    xiii. one or both of the plates comprise the spacers that are permanently fixed on the sample contact area of a respective plate;
    xiv. the spacers have:
      (a) a predetermined substantially uniform height that has a value selected in the range of 1.8 um to 3.8 um,
      (b) a shape of pillar with substantially uniform cross-section and a flat top surface;
      (c) a ratio of the width to the height equal or larger than one;
      (d) a predetermined fixed, non-random, inter-spacer distance that is in the range of 10 um to 200 um (micron);
      (e) a filling factor of equal to 1% or larger; and
      (f) the filling factor multiplies the Young's modulus of the spacer is equal to 2 MPa or larger;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A2. A device for manipulating and analyzing a thin fluidic sample layer, comprising:
  a first plate, a second plate, spacers, and adaptor wherein:
    i. the plates are movable relative to each other into different configurations;
    ii. one or both plates are flexible;
    iii. each of the plates comprises an inner surface that has a sample contact area for contacting a fluidic sample;

iv. each of the plates comprises, on its respective outer surface, a force area for applying an pressing force that forces the plates together;
v. one or both of the plates comprise the spacers that are permanently fixed on the sample contact area of a respective plate;
vi. the spacers have:
(a) a predetermined substantially uniform height that has a value selected in the range of 1.8 um to 3.8 um,
(b) a shape of pillar with substantially uniform cross-section and a flat top surface;
(c) a ratio of the width to the height equal or larger than one;
(e) a predetermined fixed, non-random, inter-spacer distance that is in the range of 10 um to 200 um;
(e) a filling factor of equal to 1% or larger; and
(f) the filling factor multiplies the Young's modulus of the spacer is equal to 2 MPa or larger;
vii. the adaptor comprising: (a) a housing, (b) attachment on the housing that allows the adaptor to attached to a mobile phone with a camera, (c) a slot in the housing that allows (1) the plates in a closed configuration to slide into the slot and (2) when the plates are in the slot, at least a part of the sample area is less 2 cm away from the outer surface of the camera, and (d) an optical system in the housing configured to have at least a part of the sample contact area be imaged by the camera;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A3. A method for manipulating and analyzing a fluidic sample, comprising:
(a) obtaining a blood sample;
(b) obtaining a first and second plates that are movable relative to each other into different configurations, wherein each plate has a sample contact area for contact a fluidic sample and the sample contact area is substantially planar, one or both plates are flexible, and one or both of the sample contact area comprise spacers that are fixed with a respective sample contacting surface, and wherein the spacers have:
i. a predetermined substantially uniform height that has a value selected in the range of 1.8 um to 3.8 um,
ii. a shape of pillar with substantially uniform cross-section and a flat top surface;
iii. a ratio of the width to the height equal or larger than one;
iv. a predetermined constant inter-spacer distance that is in the range of 10 um to 200 um;
v. a filling factor of equal to 1% or larger; and
vi. the filling factor multiplies the Young's modulus of the spacer is equal to 2 MPa or larger; and
(c) depositing the blood sample on one or both of the plates when the plates are configured in an open configuration, wherein the open configuration is a configuration in which the two plates are either partially or completely separated apart and the spacing between the plates is not regulated by the spacers;
(d) after (c), forcing the two plates into a closed configuration, in which: at least part of the blood sample is compressed by the two plates into a layer of substantially uniform thickness, wherein the uniform thickness of the layer is confined by the sample contact surfaces of the plates and is regulated by the plates and the spacers; and
(e) analyzing the analyte in the layer of uniform thickness while the plates are the closed configuration.

wherein the filling factor is the ratio of the spacer contact area (on the plate) to the total plate area.

A4. A method for manipulating and analyzing a blood sample, comprising:
(a) obtaining a blood sample;
(b) obtaining a first and second plates that are movable relative to each other into different configurations, wherein each plate has a sample contact area for contact a fluidic sample and the sample contact area is substantially planar, one or both plates are flexible, and one or both of the sample contact area comprise spacers that are fixed with a respective sample contacting surface, and wherein the spacers have:
i. a predetermined substantially uniform height that has a value selected in the range of 1.8 um to 3.8 um,
ii. a shape of pillar with substantially uniform cross-section and a flat top surface;
iii. a ratio of the width to the height equal or larger than one;
iv. a predetermined constant inter-spacer distance that is in the range of 10 um to 200 um;
v. a filling factor of equal to 1% or larger; and
vi. the filling factor multiplies the Young's modulus of the spacer is equal to 2 MPa or larger; and
(c) depositing the blood sample on one or both of the plates when the plates are configured in an open configuration, wherein the open configuration is a configuration in which the two plates are either partially or completely separated apart and the spacing between the plates is not regulated by the spacers;
(d) after (c), forcing the two plates into a closed configuration, in which: at least part of the blood sample is compressed by the two plates into a layer of substantially uniform thickness, wherein the uniform thickness of the layer is confined by the sample contact surfaces of the plates and is regulated by the plates and the spacers; and
(e) analyzing the analyte in the layer of uniform thickness while the plates are the closed configuration.

wherein the filling factor is the ratio of the spacer contact area (on the plate) to the total plate area, and wherein the analyzing in step (e) imaging and counting the red blood cells, white blood cells and/or platelets.

The methods of embodiments A3 and A4, wherein the method further comprises, between step (d) and (e), a step of inserting the plates in a closed configuration into the slot in an adaptor, wherein the adaptor comprises: (a) a housing, (b) attachment on the housing that allows the adaptor to attached to a mobile phone with a camera, (c) a slot in the housing that allows (1) the plates in a closed configuration to slide into the slot and (2) when the plates are in the slot, at least a part of the sample area is less 2 cm away from the outer surface of the camera, and (d) an optical system in the housing configured to have at least a part of the sample contact area be imaged by the camera.

The devices or methods of any prior embodiment, wherein a fourth power of the inter-spacer-distance (IDS) divided by the thickness (h) and the Young's modulus (E) of the flexible plate (ISD^4/(hE)) is 5×10^6 um^3/GPa or less.

The devices or methods of any prior embodiment, wherein a fourth power of the inter-spacer-distance (IDS) divided by the thickness (h) and the Young's modulus (E) of the flexible plate (ISD^4/(hE)) is 1×10^6 um^3/GPa or less.

The devices or methods of any prior embodiment, wherein a fourth power of the inter-spacer-distance (IDS) divided by the thickness (h) and the Young's modulus (E) of the flexible plate (ISD^4/(hE)) is 5×10^5 um^3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD^4/(hE)) is 1×10^5 um^3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD^4/(hE)) is 1×10^4 um^3/GPa or less.

16. The devices or methods of any prior embodiments, wherein the flexible plates and the spacers are configured, such that the fourth power of the inter-spacer-distance (IDS) divided by the thickness (h) and the Young's modulus (E) of the flexible plate (ISD$^4$/(hE)) is 5×10$^6$ um$^3$/GPa or less.

17. The devices or methods of any prior embodiments, wherein the sample has a viscosity in the range of 0.1 to 4 (mPa s).

18. The devices or methods of any prior embodiments, wherein the spacer height is in the range of 2 um to 2.5 um.

19. The devices or methods of any prior embodiments, wherein the spacer height is in the range of 1.8 um to 2.2 um.

20. The devices or methods of any prior embodiments, wherein the spacer height is in the range of 2 um to 3 um.

21. The devices or methods of any prior embodiments, wherein the spacer height is 2 um, 2.2 um, 2.4 um, 2.6 um, 2.8 um, 3 um, 3.2 um, 3.4 um, 3.6 um, or in a range of any two values.

22. The devices or methods of any prior embodiment, wherein the uniform thickness sample area has an area of 5 mm2 (millimeter square) to 10 mm2.

23. The devices or methods of any prior embodiment, wherein the uniform thickness sample area has an area of 10 mm2 (millimeter square) to 20 mm2.

24. The devices or methods of any prior embodiment, wherein the uniform thickness sample area has an area of 20 mm2 (millimeter square) to 40 mm2.

25. The devices or methods of any prior embodiment, wherein the uniform thickness sample area has an area of 40 mm2 (millimeter square) to 60 mm2.

26. The devices or methods of any prior embodiment, wherein the uniform thickness sample area has an area of 60 mm2 (millimeter square) to 80 mm2.

27. The devices or methods of any prior embodiment, wherein the uniform thickness sample area has an area of 80 mm2 (millimeter square) to 150 mm2.

28. The devices or methods of any prior embodiment, wherein inter-spacer distance that is at least about 2 times larger than the size of the analyte, up to 200 um.

29. The devices or methods of any prior embodiment, wherein a ratio of the inter-spacer-distance to the spacer width is 1.5 or larger.

30. The devices or methods of any prior embodiment, wherein a ratio of the width to the height of the spacer is 1 or larger.

31. The devices or methods of any prior embodiment, wherein a ratio of the width to the height of the spacer is 1.5 or larger.

32. The devices or methods of any prior embodiment, wherein a ratio of the width to the height of the spacer is 2 or larger.

33. The devices or methods of any prior embodiment, wherein a ratio of the width to the height of the spacer is larger than 2, 3, 5, 10, 20, 30, 50, or in a range of any two the value.

34. The methods of any prior embodiment, wherein the force that presses the two plates into the closed configuration is an imprecise pressing force.

35. The devices or methods of any prior embodiment, wherein the spacers are configured, such that the filling factor is in the range of 1% to 5%.

36. The devices or methods of any prior embodiment, wherein the spacers are configured, such that the filling factor is in the range of 5% to 10%.

37. The devices or methods of any prior embodiment, wherein the spacers are configured, such that the filling factor is in the range of 10% to 20%.

38. The devices or methods of any prior embodiment, wherein the spacers are configured, such that the filling factor is in the range of 20% to 30%.

39. The devices or methods of any prior embodiment, wherein the spacers are configured, such that the filling factor is 5%, 10%, 20%, 30%, 40%, 50%, or in a range of any two of the values.

40. The devices or methods of any prior embodiment, wherein the spacers are configured, such that the filling factor is 50%, 60%, 70%, 80%, or in a range of any two of the values.

41. The devices or methods of any prior embodiment, wherein the spacers are configured, such that the filling factor multiplies the Young's modulus of the spacer is in the range of 2 MPa and 10 MPa.

42. The devices or methods of any prior embodiment, wherein the spacers are configured, such that the filling factor multiplies the Young's modulus of the spacer is in the range of 10 MPa and 20 MPa.

43. The devices or methods of any prior embodiment, wherein the spacers are configured, such that the filling factor multiplies the Young's modulus of the spacer is in the range of 20 MPa and 40 MPa.

44. The devices or methods of any prior embodiment, wherein the spacers are configured, such that the filling factor multiplies the Young's modulus of the spacer is in the range of 40 MPa and 80 MPa.

45. The devices or methods of any prior embodiment, wherein the spacers are configured, such that the filling factor multiplies the Young's modulus of the spacer is in the range of 80 MPa and 120 MPa.

46. The devices or methods of any prior embodiment, wherein the spacers are configured, such that the filling factor multiplies the Young's modulus of the spacer is in the range of 120 MPa to 150 MPa.

47. The devices or methods of any prior embodiment, wherein the device further comprises a dry reagent coated on one or both plates.

48. The devices or methods of any prior embodiment, wherein the device further comprises, on one or both plates, a dry binding site that has a predetermined area, wherein the dry binding site binds to and immobilizes an analyte in the sample.
49. The devices or methods of any prior embodiment, wherein the device further comprises, on one or both plates, a releasable dry reagent and a release time control material that delays the time that the releasable dry regent is released into the sample.
50. The device of any prior embodiment, wherein the release time control material delays the time that the dry regent starts is released into the sample by at least 3 seconds.
51. The device of any prior embodiment, wherein the regent comprises anticoagulant and/or staining reagent(s) 52. The device of any prior embodiment, wherein the reagent comprises cell lysing reagent(s).
53. The devices or methods of any prior embodiment, wherein the device further comprises, on one or both plates, one or a plurality of dry binding sites and/or one or a plurality of reagent sites.
54. The device of any prior device embodiment, wherein the analyte comprises a molecule (e.g., a protein, peptides, DNA, RNA, nucleic acid, or other molecule), cells, tissues, viruses, and nanoparticles with different shapes.
55. The device of any prior device embodiment, wherein the analyte comprises white blood cells, red blood cells and platelets.
56. The device of any prior device embodiment, wherein the analyte is stained.
57. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.
58. The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.
59. The devices or methods of any prior embodiment, wherein for a flexible plate, the thickness of the flexible plate times the Young's modulus of the flexible plate is in the range 60 to 750 GPa-um.
60. The devices or methods of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$,
61. The devices or methods of any prior embodiment, wherein one or both plates comprises a location marker, either on a surface of or inside the plate, that provide information of a location of the plate.
62. The devices or methods of any prior embodiment, wherein one or both plates comprises a scale marker, either on a surface of or inside the plate, that provide information of a lateral dimension of a structure of the sample and/or the plate.
63. The devices or methods of any prior embodiment, wherein one or both plates comprises an imaging marker, either on surface of or inside the plate, that assists an imaging of the sample.
64. The devices or methods of any prior embodiment, wherein the spacers functions as a location marker, a scale marker, an imaging marker, or any combination of thereof.
65. The devices or methods of any prior embodiment, wherein the average thickness of the layer of uniform thickness is in the range of 2 um to 2.2 um and the sample is blood.
66. The devices or methods of any prior embodiment, wherein the average thickness of the layer of uniform thickness is in the range of 2.2 um to 2.6 um and the sample is blood.
67. The devices or methods of any prior embodiment, wherein the average thickness of the layer of uniform thickness is in the range of 1.8 um to 2 um and the sample is blood.
68. The devices or methods of any prior embodiment, wherein the average thickness of the layer of uniform thickness is in the range of 2.6 um to 3.8 um and the sample is blood.
69. The devices or methods of any prior embodiment, wherein the average thickness of the layer of uniform thickness is in the range of 1.8 um to 3.8 um and the sample is whole blood without a dilution by another liquid.
70. The devices or methods of any prior embodiment, wherein the average thickness of the layer of uniform thickness is about equal to a minimum dimension of an analyte in the sample.
71. The devices or methods of any prior embodiment, wherein the inter-spacer distance is in the range of 7 um to 50 um.
72. The devices or methods of any prior embodiment, wherein the inter-spacer distance is in the range of 50 um to 120 um.
73. The devices or methods of any prior embodiment, wherein the inter-spacer distance is in the range of 120 um to 200 um (micron).
74. The devices or methods of any prior embodiment, wherein the inter-spacer distance is substantially periodic.
75. The devices or methods of any prior embodiment, wherein the spacers are pillars with a cross-sectional shape selected from round, polygonal, circular, square, rectangular, oval, elliptical, or any combination of the same.
76. The devices or methods of any prior embodiment, wherein the spacers have are pillar shape and have a substantially flat top surface, wherein, for each spacer, the ratio of the lateral dimension of the spacer to its height is at least 1.
77. The devices or methods of any prior embodiment, wherein each spacer has the ratio of the lateral dimension of the spacer to its height is at least 1.
78. The devices or methods of any prior embodiment, wherein the minimum lateral dimension of spacer is less than or substantially equal to the minimum dimension of an analyte in the sample.
79. The devices or methods of any prior embodiment, wherein the minimum lateral dimension of spacer is in the range of 0.5 um to 100 um.
80. The devices or methods of any prior embodiment, wherein the minimum lateral dimension of spacer is in the range of 0.5 um to 10 um.

81. The devices or methods of any prior embodiment, wherein the sample is blood.
82. The devices or methods of any prior embodiment, wherein the sample is whole blood without dilution by liquid.
83. The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
84. The devices or methods of any prior embodiment, wherein the sample is a biological sample, an environmental sample, a chemical sample, or clinical sample.
85. The devices or methods of any prior embodiment, wherein the spacers have a pillar shape, and the sidewall corners of the spacers have a round shape with a radius of curvature at least 1 um.
86. The devices or methods of any prior embodiment, wherein the spacers have a density of at least $100/mm^2$.
87. The devices or methods of any prior embodiment, wherein the spacers have a density of at least $1000/mm^2$.
88. The devices or methods of any prior embodiment, wherein at least one of the plates is transparent.
89. The devices or methods of any prior embodiment, wherein at least one of the plates is made from a flexible polymer.
90. The devices or methods of any prior embodiment, wherein, for a pressure that compresses the plates, the spacers are not compressible and/or, independently, only one of the plates is flexible.
91. The device of any of any prior embodiment, wherein the flexible plate has a thickness in the range of 10 um to 200 um.
92. The devices or methods of any prior embodiment, wherein the variation is less than 30%.
93. The devices or methods of any prior embodiment, wherein the variation is less than 10%.
94. The devices or methods of any prior embodiment, wherein the variation is less than 5%.
95. The devices or methods of any prior embodiment, wherein the first and second plates are connected and are configured to be changed from the open configuration to the closed configuration by folding the plates.
96. The devices or methods of any prior embodiment, wherein the first and second plates are connected by a hinge and are configured to be changed from the open configuration to the closed configuration by folding the plates along the hinge.
97. The devices or methods of any prior embodiment, wherein the first and second plates are connected by a hinge that is a separate material to the plates, and are configured to be changed from the open configuration to the closed configuration by folding the plates along the hinge
98. The devices or methods of any prior embodiment, wherein the first and second plates are made in a single piece of material and are configured to be changed from the open configuration to the closed configuration by folding the plates.
99. The devices or methods of any prior embodiment, wherein the layer of uniform thickness sample is uniform over a lateral area that is at least 1 $mm^2$.
100. The devices or methods of any prior embodiment, wherein the device is configured to analyze the sample in 60 seconds or less.
101. The devices or methods of any prior embodiment, wherein at the closed configuration, the final sample thickness device is configured to analyze the sample in 60 seconds or less.
102. The devices or methods of any prior embodiment, wherein at the closed configuration, the final sample thickness device is configured to analyze the sample in 10 seconds or less.
103. The devices or methods of any prior embodiment, wherein the dry binding site comprises a capture agent.
104. The devices or methods of any prior embodiment, wherein the dry binding site comprises an antibody or nucleic acid.
105. The devices or methods of any prior embodiment, wherein the releasable dry reagent is a labeled reagent.
106. The devices or methods of any prior embodiment, wherein the releasable dry reagent is a fluorescently-labeled reagent.
107. The devices or methods of any prior embodiment, wherein the releasable dry reagent is a fluorescently-labeled antibody.
108. The devices or methods of any prior embodiment, wherein the releasable dry reagent is a cell stain.
109. The devices or methods of any prior embodiment, wherein the releasable dry reagent is a cell lysing.
110. The devices or methods of any prior embodiment, wherein the detector is an optical detector that detects an optical signal.
111. The devices or methods of any prior embodiment, wherein the detector is an electric detector that detect electrical signal.
112. The device of any prior device embodiment, wherein the spacing are fixed on a plate by directly embossing the plate or injection molding of the plate.
113. The device of any prior device embodiment, wherein the materials of the plate and the spacers are selected from polystyrene, PMMA, PC, COC, COP, or another plastic.
114. A system for rapidly analyzing a sample using a mobile phone comprising:
    (a) a device of any prior embodiment;
    (b) a mobile communication device comprising:
        i. one or a plurality of cameras for the detecting and/or imaging the sample;
        ii. electronics, signal processors, hardware and software for receiving and/or processing the detected signal and/or the image of the sample and for remote communication; and
    (c) a light source from either the mobile communication device or an external source;
    wherein the detector in The devices or methods of any prior embodiment is provided by the mobile communication device, and detects an analyte in the sample at the closed configuration.
115. The system of any prior system embodiment, wherein one of the plates has a binding site that binds an analyte, wherein at least part of the uniform sample thickness layer is over the binding site, and is substantially less than the average lateral linear dimension of the binding site.

116. The system of any prior system embodiment, further comprising:
(d) a housing configured to hold the sample and to be mounted to the mobile communication device.
117. The system of any prior system embodiment, wherein the housing comprises optics for facilitating the imaging and/or signal processing of the sample by the mobile communication device, and a mount configured to hold the optics on the mobile communication device.
118. The system of any prior system embodiment, wherein an element of the optics in the housing is movable relative to the housing.
119. The system of any prior system embodiment, wherein the mobile communication device is configured to communicate test results to a medical professional, a medical facility or an insurance company.
120. The system of any prior system embodiment, wherein the mobile communication device is further configured to communicate information on the test and the subject with the medical professional, medical facility or insurance company.
121. The system of any prior system embodiment, wherein the mobile communication device is further configured to communicate information of the test to a cloud network, and the cloud network process the information to refine the test results.
122. The system of any prior system embodiment, wherein the mobile communication device is further configured to communicate information of the test and the subject to a cloud network, the cloud network process the information to refine the test results, and the refined test results will send back the subject.
123. The system of any prior system embodiment, wherein the mobile communication device is configured to receive a prescription, diagnosis or a recommendation from a medical professional.
124. The system of any prior system embodiment, wherein the mobile communication device is configured with hardware and software to:
(a) capture an image of the sample;
(b) analyze a test location and a control location in in image; and
(c) compare a value obtained from analysis of the test location to a threshold value that characterizes the rapid diagnostic test.
125. The system of any prior system embodiment, wherein at least one of the plates comprises a storage site in which assay reagents are stored.
126. The system of any prior system embodiment, at least one of the cameras reads a signal from the device.
127. The system of any prior system embodiment, wherein the mobile communication device communicates with the remote location via a wifi or cellular network.
128. The system of any prior system embodiment, wherein the mobile communication device is a mobile phone.
129. A method for rapidly analyzing an analyte in a sample using a mobile phone, comprising:
(a) depositing a sample on the device of any prior system embodiment;
(b) assaying an analyte in the sample deposited on the device to generate a result; and
(c) communicating the result from the mobile communication device to a location remote from the mobile communication device.
130. The method of any prior embodiments embodiment, wherein the analyte comprises a molecule (e.g., a protein, peptides, DNA, RNA, nucleic acid, or other molecule), cells, tissues, viruses, and nanoparticles with different shapes.
131. The method of any prior embodiment, wherein the analyte comprises white blood cell, red blood cell and platelets.
132. The method of any prior embodiment, wherein the assaying comprises performing a white blood cells differential assay.
133. The method of any prior embodiments embodiment, wherein the method comprises:
analyzing the results at the remote location to provide an analyzed result; and
communicating the analyzed result from the remote location to the mobile communication device.
134. The method of any prior embodiment, wherein the analysis is done by a medical professional at a remote location.
135. The method of any prior embodiment, wherein the mobile communication device receives a prescription, diagnosis or a recommendation from a medical professional at a remote location.
136. The method of any prior embodiment, wherein the sample is a bodily fluid.
137. The method of any prior embodiment, wherein the bodily fluid is blood, saliva or urine.
138. The method of any prior embodiment, wherein the sample is whole blood without dilution by a liquid.
139. The method of any prior embodiment, wherein the assaying step comprises detecting an analyte in the sample.
140. The method of any prior embodiment, wherein the analyte is a biomarker.
141. The method of any prior embodiment, wherein the analyte is a protein, nucleic acid, cell, or metabolite.
142. The method of any prior embodiment, wherein the method comprises counting the number of red blood cells.
143. The method of any of any prior embodiment, wherein the method comprises counting the number of white blood cells.
144. The method of any prior embodiment, wherein method comprises staining the cells in the sample and counting the number of neutrophils, lymphocytes, monocytes, eosoniphils and basophils.
145. The method of any prior embodiments embodiment, wherein the assay done in step (b) is a binding assay or a biochemical assay.
146. A method for analyzing a sample comprising:
obtaining a device of any prior device embodiment;
depositing the sample onto one or both pates of the device;
placing the plates in a closed configuration and applying an external force over at least part of the plates; and
analyzing the in the layer of uniform thickness while the plates are the closed configuration.
147. The method of any prior analysis method embodiment, wherein the method comprises:
(a) obtaining a sample;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
  vii. a predetermined substantially uniform height,
  viii. a shape of pillar with substantially uniform cross-section and a flat top surface;
  ix. a ratio of the width to the height equal or larger than one;
  x. a predetermined constant inter-spacer distance that is in the range of 10 um to 200 um;
  xi. a filling factor of equal to 1% or larger; and
(c) depositing the sample on one or both of the plates when the plates are configured in an open configuration, wherein the open configuration is a configuration in which the two plates are either partially or completely separated apart and the spacing between the plates is not regulated by the spacers;
(d), after (c), using the two plates to compress at least part of the sample into a layer of substantially uniform thickness that is confined by the sample contact surfaces of the plates, wherein the uniform thickness of the layer is regulated by the spacers and the plates, and has an average value in the range of 1.8 um to 3 um with a variation of less than 10%, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
(e) analyzing the in the layer of uniform thickness while the plates are the closed configuration;
wherein the filling factor is the ratio of the spacer contact area to the total plate area;
wherein a conformable pressing is a method that makes the pressure applied over an area is substantially constant regardless the shape variation of the outer surfaces of the plates; and
wherein the parallel pressing applies the pressures on the intended area at the same time, and a sequential pressing applies the pressure on a part of the intended area and gradually move to other area.

A method for counting red blood cells, white blood cells, and platelets in a blood sample using a single device, comprising:
(a) obtaining a blood sample;
(b) obtaining any prior device;
(c) depositing the blood sample on one or both of the plates when the plates are configured in an open configuration, wherein one of the configurations is the open configuration, in which: the two plates are partially or completely separated apart, the spacing between the plates is not regulated by the spacers, and the sample is deposited on one or both of the plates;
(d) after (c), forcing the two plates into a closed configuration, wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
(e) capturing images of the sample in the layer of uniform thickness while the plates are the closed configuration; and
(f) analyzing the images to determine the number and concentration of red blood cells, white blood cells, and platelets, through the counting of cells in the images;

148. The method of any prior embodiment, wherein the blood sample is undiluted.
149. The method of any prior analysis method embodiment, wherein the method comprises
removing the external force after the plates are in the closed configuration; and
imaging the blood cells in the layer of uniform thickness while the plates are the closed configuration; and counting a number of blood cells in an area of the image.
150. The method of any prior analysis method embodiment, wherein the inter-spacer distance is in the range of 20 um to 200 um.
151. The method of any prior analysis method embodiment, wherein the inter-spacer distance is in the range of 5 um to 20 um.
152. The method of any prior analysis method embodiment, wherein a product of the filling factor and the Young's modulus of the spacer is 2 MPa or larger.
153. The method of any prior analysis method embodiment, the surface variation is less than 30 nm.
154. The method of any prior analysis method embodiment, wherein the blood sample is undiluted whole blood into which no anticoagulant has been added.
155. The method of any prior analysis method embodiment, wherein the depositing step (b) is done by:
i. pricking the skin of a human release a droplet of blood onto the skin and ii. contacting the droplet of blood with one or both of the plates without use of a blood transfer tool.
156. The method of any prior analysis method embodiment, wherein the analyzing step comprise counting the number of red blood cells.
157. The method of any prior analysis method embodiment, wherein the analyzing step comprise counting the number of white blood cells.
158. The method of any prior analysis method embodiment, wherein the analyzing step comprise staining the cells in the sample and counting the number of neutrophils, lymphocytes, monocytes, eosoniphils and basophils.
159. The method of any prior analysis method embodiment, wherein the imaging and counting is done by:
i. illuminating the cells in the layer of uniform thickness;
ii. taking one or more images of the cells using a CCD or CMOS sensor;
iii. identifying cells in the image using a computer; and
iv. counting a number of cells in an area of the image.
160. The method of any prior analysis method embodiment, wherein the external force is provided by human hand.
161. The method of any prior analysis method embodiment, further comprising measuring sodium, potassium, chloride, bicarbonate, blood urea, nitrogen, magnesium, creatinine, glucose, calcium, HDL cholesterol LDL cholesterol levels and/or triglyceride levels in the layer of uniform thickness.

162. The method of any prior analysis method embodiment, wherein it future comprises a dry reagent coated on one or both plates.
163. The method of any prior analysis method embodiment, wherein the layer of uniform thickness sample has a thickness uniformity of up to +/−5%.
164. The method of any prior analysis method embodiment, wherein the spacers are pillars with a cross-sectional shape selected from round, polygonal, circular, square, rectangular, oval, elliptical, or any combination of the same.
165. The method of any prior analysis method embodiment, wherein the spacing between the spacers is approximately the average thickness of RBCs.
166. The method of any prior analysis method embodiment, wherein the analyzing step comprises imaging cells in the blood.
167. The method of any prior analysis method embodiment, wherein cells comprises red blood cells, while blood cells, or platelets.
168. The method of any prior analysis method embodiment, wherein the analyzing the blood comprises imaging cancer cells, viruses, or bacterias in the blood.
169. The method of any prior analysis method embodiment, wherein the analyzing the blood comprises detecting of proteins or nucleic acids.
170. The method of any prior analysis method embodiment, wherein the analyzing the blood comprises measuring of hemocytes, comprising determining of the sample thickness using the spacer, determining the lateral area by imaging, and calculating the area of red blood cells using the 2D image.
171. The method of any prior analysis method embodiment, wherein the analyzing the blood comprises measuring of red cell concentration in the blood.
172. The method of any prior analysis method embodiment, wherein the analyzing the blood comprises measuring of white blood cell concentration in the blood.
173. The method of any prior analysis method embodiment, wherein the analyzing the blood comprises measuring of platelet concentration in the blood.

Exemplary Embodiments for Using a Gap 8 to 12 um

In some embodiments, different spacer height and hence different sample thickness can improve the accuracy of the counting of certain cells. For example, for counting white blood cells, our experiments show (FIG. 15 to 17) that in a undiluted blood for using a give FoV provide by mobile phone, a spacer height of 5 to 15 um gives more accurate results than 2 um to 3 um. Clearly, the embodiments in prior paragraphs can be used for pillar height of 5 to 15 um, preferred 10 um, while a same of a similar sample thickness uniformity can be achieved. Such pillar heights have advantage for imaging and counting the white blood cells in a undiluted blood.

The device and method of any prior embodiment is used to (1) count the white blood cells, (b) count the white blood cells sub-types (including neutrophils, eosinophils, basophils, lymphocytes, and monocytes), and (3) differentiate white blood cells, wherein the device further comprises spacers that regulate the spacing between the sample contact areas when the plates are in a closed configuration.

The devices or methods of any prior embodiment, wherein the average thickness of the layer of uniform thickness is in the range of 5.0 um to 8.5 um.

The devices or methods of any prior embodiment, wherein the average thickness of the layer of uniform thickness is in the range of 7.5 um to 10.5 um.

The devices or methods of any prior embodiment, wherein the average thickness of the layer of uniform thickness is in the range of 9.5 um to 12.5 um.

The devices or methods of any prior embodiment, wherein the average thickness of the layer of uniform thickness is in the range of 9.5 um to 12.5 um.

The devices or methods of any prior embodiment, wherein the average thickness of the layer of uniform thickness is in the range of 11.5 um to 13.5 um.

The devices or methods of any prior embodiment, wherein the average thickness of the layer of uniform thickness is in the range of 12.5 um to 14.5 um.

The devices or methods of any prior embodiment, wherein the average thickness of the layer of uniform thickness is in the range of 13.5 um to 16 um.

The devices or methods of any prior embodiment, wherein spacer height is in the range of 5.0 um to 8.5 um.

The devices or methods of any prior embodiment, wherein spacer height is in the range of 7.5 um to 10.5 um.

The devices or methods of any prior embodiment, wherein spacer height is in the range of 9.5 um to 12.5 um.

The devices or methods of any prior embodiment, wherein spacer height is in the range of 9.5 um to 12.5 um.

The devices or methods of any prior embodiment, wherein spacer height is in the range of 11.5 um to 13.5 um.

The devices or methods of any prior embodiment, wherein spacer height is in the range of 12.5 um to 14.5 um.

The devices or methods of any prior embodiment, wherein spacer height is in the range of 13.5 um to 16 um.

The devices or methods of any prior embodiment, wherein the preferred field of view for counting and differentiating WBCs is 0.1 mm$^2$, 10 mm$^2$, 50 mm$^2$, 100 mm$^2$ or a range between any two of the values;

The devices or methods of any prior embodiment, wherein when the gap size of device is 10 um, the FoV is larger than 36 mm$^2$, thereby the WBC counting and differentiate accuracy is less than 5%.

The devices or methods of any prior embodiment, wherein when the gap size of device is 10 um, the FoV is larger than 16 mm$^2$, thereby the WBC counting and differentiate accuracy is less than 10%.

The devices or methods of any prior embodiment, wherein when the gap size of device is 10 um, the FoV is larger than 2 mm$^2$, thereby the WBC counting and differentiate accuracy is less than 20%.

The devices or methods of any prior embodiment, wherein field of view is 0.1 mm$^2$ to 10 mm$^2$, preferred gap size of device is in the range of 10 um to 30 um, 30 um to 50 um, thereby the counting and differentiate accuracy is less than 10%.

The devices or methods of any prior embodiment, wherein field of view is 0.1 mm$^2$ to 10 mm$^2$, preferred gap size of device is in the range of 10 um to 30 um, thereby the counting and differentiate accuracy is less than 20%.

The devices or methods of any prior embodiment, wherein field of view is 10 mm$^2$ to 50 mm$^2$, preferred gap size of device is in the range of 5 um to 10 um, 10 um to 30 um, thereby the counting and differentiate accuracy is less than 10%.

The devices or methods of any prior embodiment, wherein field of view is 10 mm$^2$ to 50 mm$^2$, preferred gap size of device is in the range of 2 um to 5 um, 5 um to 10 um, 10 um to 30 um, thereby the counting and differentiate accuracy is less than 20%.

The devices or methods of any prior embodiment, wherein field of view is field of view of 50 mm$^2$ to 100 mm$^2$, preferred gap size of device is in the range of 2 um to 5 um, 5 um to 10 um, 10 um to 30 um, 30 um to 50 um thereby the counting and differentiate accuracy is less than 10%.

The devices or methods of any prior embodiment, wherein the spacer has a height of preferred range of 2 um to 5 um, thereby the WBCs missing counting is less than 15%.

The devices or methods of any prior embodiment, wherein the spacer has a height of preferred range of 2 um to 5 um, 5 um to 10 um, thereby the WBCs missing counting is less than 30%.

The devices or methods of any prior embodiment, wherein the spacer has a height of preferred range of 2 um to 5 um, 5 um to 10 um, 10 um to 30 um thereby the WBCs missing counting is less than 60%.

The devices or methods of any prior embodiment, the sample to phone lens distance is in the range of 2 mm to 5 mm.

The devices or methods of any prior embodiment, the sample to phone lens distance is in the range of 4 mm to 7 mm.

The devices or methods of any prior embodiment, the sample to phone lens distance is in the range of 6 mm to 9 mm.

The devices or methods of any prior embodiment, the sample to phone lens distance is in the range of 8 mm to 11 mm.

The devices or methods of any prior embodiment, the sample to phone lens distance is in the range of 10 mm to 13 mm.

The devices or methods of any prior embodiment, the sample to phone lens distance is in the range of 12 mm to 15 mm.

AC1 A method for white blood cell and sub-type (including neutrophils, eosinophils, basophils, lymphocytes, and monocytes) counting using a single device, comprising:
  (a) obtaining a blood sample;
  (b) obtaining any prior device wherein the spacer height is 5 um to 15 um, perferely 10 um.
  (c) depositing the blood sample on one or both of the plates when the plates are configured in an open configuration, wherein one of the configurations is the open configuration, in which: the two plates are partially or completely separated apart, the spacing between the plates is not regulated by the spacers, and the sample is deposited on one or both of the plates;
  (d) after (c), forcing the two plates into a closed configuration, wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
  (e) capturing images of the sample in the layer of uniform thickness while the plates are the closed configuration; and
  (f) analyzing the images to determine the respective number of white blood cells, neutrophils, lymphocytes, monocytes, eosinophils and basophils, through the counting of the cell number in the image and the analysis of the fluorescence color and shape for each white blood cell;
  wherein the filling factor is the ratio of the spacer contact area (on the plate) to the total plate area.

AC2. The method of embodiment AC1, wherein the blood sample is undiluted.

AC3. The device or method or embodiment AC1, wherein the staining and shape of white blood cell provide fluorescence color and dimension distinguish of white blood cell and its subtypes.

AC4. The device or method or embodiment AC1, wherein the device further comprises, on one or both plates, multi reagent layers including anti-conglutination, cell lysing, cell staining, release time control material layers, or their combinations.

FIG. 15 shows experimental observation of WBC counting accuracy vs. FoV vs. QMAX device gap. (a) Plots of WBC counting accuracy vs. QMAX gap size with effective field of view (FoV) of 4 mm$^2$, 16 mm$^2$, 36 mm$^2$, 64 mm$^2$, 100 mm$^2$; (b) Plots of WBC counting accuracy vs. field of view (FoV) with QMAX gap size of 2 um, 3 um, 5 um, 6.2 um, 10 um and 30 um.

In this set of experiment, first plate is 1 mm thick PMMA with printed acridine orange dye, and second plate is X-Plate has 30×40 um pillar size, 80 um inter spacing distance, made on 175 um thick PMMA. 1 uL fresh blood without any anticoagulant was used in the test.

Counting accuracy is defined as the counting number's standard deviation for all the fields on card with certain FoV. This counting accuracy represent the case when random pick a field of FoV on sample to measure, how it represents the average number of all the field on the device. Generally, WBC counting is more accurate with larger field of view and larger QMAX gap.

Figure 16:
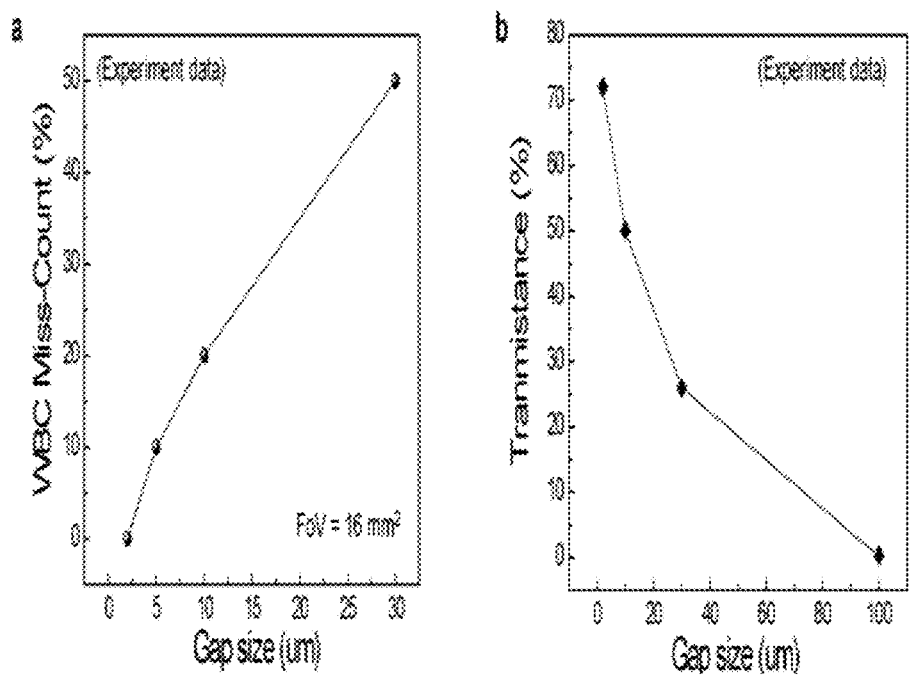
FIG. 16 shows experimental observation of (a) Plots of WBC miss count percentage vs. QMAX gap size of 2 um, 5 um, 10 um and 30 um with field of view of 4.7 mm×3.5 mm (16 mm$^2$).

FIG. 16 shows experimental observation of (a) Plots of WBC miss count percentage vs. QMAX gap size of 2 um, 5 um, 10 um and 30 um with field of view of 4.7 mm×3.5 mm (16 mm$^2$).

Here, miss count is defined as the percentage difference between the back-calculated WBC concentration (from counting number over counting area over filling factor over gap size) and sample's real WBC concentrations (measured by calibrated commercial hematology machine). (b) Plots of QMAX transmittance at 500 nm wavelength (which is close to fluorescence of WBCs) vs. QMAX gap size.

Figure 17:
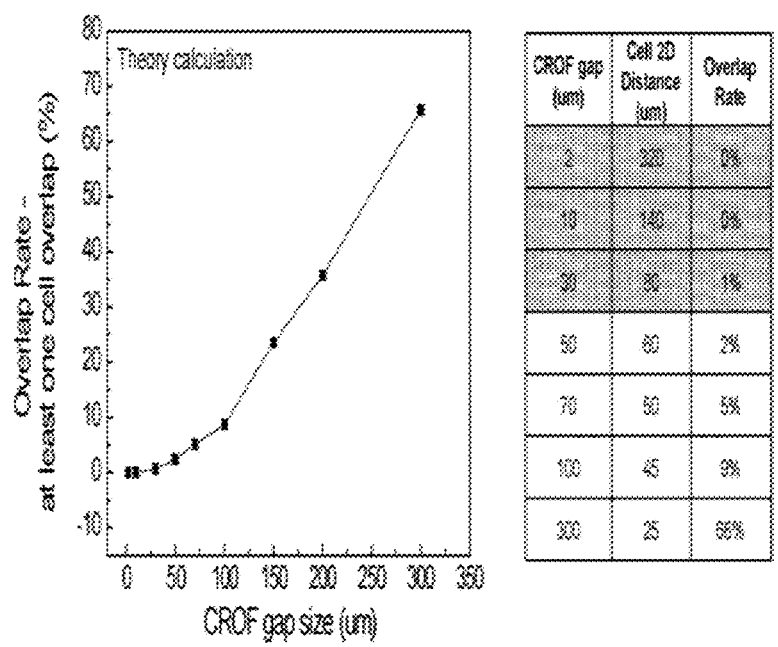
FIG. 17 shows the theory calculation of overlap rate of WBC cell self vs. QMAX gap.

More WBCs are miss counted with larger gap size (thicker blood film). One of the reason is fluorescence from WBC is dimmed and blocked by the RBCs with thicker blood film as shown in the (b) transmittance vs. gap size. For example, transmittance of 2 um QMAX device with whole blood at 500 nm wavelength is around 75%, while transmittance of 30 um QMAX device with whole blood at 500 nm wavelength drops to 25% FIG. 17 shows the theory calculation of overlap rate of WBC cell self vs. QMAX gap.

From the calculation, more WBCs are overlapped when gap size is larger, especially larger than 30 um.

The devices or methods of any prior embodiment, wherein the device further comprises, on one or both plates, a cell lysing reagent that selectively lyse the WBCs, RBCs, PLTs or any cell types in sample.

The devices or methods of any prior embodiment, wherein the device further comprises, on one or both plates, multi reagent layers including anti-conglutination, cell lysing, cell staining, release time control material layers, and their combinations;
  wherein each layer coated on the plates has a thickness of 10 nm, 100 nm, 200 nm, 500 nm, 1 um or a range between any two of the values.
  where anti-conglutination agent comprises ethylenediaminetetraacetic acid (EDTA), EDTA disodium, K2EDTA, K3EDTA, and etc.

wherein cell stain agent comprise Wright's stain (Eosin, methylene blue), Giemsa stain (Eosin, methylene blue, and Azure B), May-Grunwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride).

wherein cell lysing agent comprise ammonium chloride, sodium bicarbonate, ethylenediaminetetraacetic acid (EDTA), acetic acid, citric acid, other acid and base, and etc.

wherein release time control material comprise albumin, carbomers, carboxymethyl cellulose, carrageenan, chitosan, dextrin, polyethylene glycol, polyvinyl pyrrolidone, polyvinyl alcohol, and etc.

The methods of any prior embodiment, the RBCs, PLTs or both are lysed in sample before the detection of WBCs.

The methods of any prior embodiment, the WBCs, PLTs or both are lysed in sample before the detection of RBCs.

The methods of any prior embodiment, the RBCs, WBCs or both are lysed in sample before the detection of PLTs.

Exemplary Device and Method for Measuring White Blood Cells

AA1. A device for analyzing white blood cells in a blood sample, comprising:
a first plate, a second plate, and spacers, wherein:
  i. the plates are movable relative to each other into different configurations;
  ii. one or both plates are flexible;
  iii. each of the plates comprises an inner surface that has a sample contact area for contacting a blood sample;
  iv. one or both of the plates comprise the spacers that are permanently fixed on the sample contact area of a respective plate;
  v. the spacers have:
    (a) a predetermined substantially uniform height that has a value selected in the range of 2 um to 20 um,
    (b) a shape of pillar with substantially uniform cross-section and a flat top surface;
    (c) a ratio of the width to the height equal or larger than one;
    (g) a predetermined fixed, non-random, inter-spacer distance that is in the range of 10 um to 200 um (micron);
    (e) a filling factor of equal to 1% or larger; and
    (f) the filling factor multiplies the Young's modulus of the spacer is equal to 2 MPa or larger;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A device for analyzing white blood cells in a blood sample, comprising:
a first plate, a second plate, spacers, and adaptor wherein:
  viii. the plates are movable relative to each other into different configurations;
  ix. one or both plates are flexible;
  x. each of the plates comprises an inner surface that has a sample contact area for contacting a fluidic sample;
  xi. one or both of the plates comprise the spacers that are permanently fixed on the sample contact area of a respective plate;
  xii. the spacers have:
    (a) a predetermined substantially uniform height that has a value selected in the range of 2 um to 20 um,
    (b) a shape of pillar with substantially uniform cross-section and a flat top surface;
    (c) a ratio of the width to the height equal or larger than one;
    (h) a predetermined fixed, non-random, inter-spacer distance that is in the range of 10 um to 200 um;
    (e) a filling factor of equal to 1% or larger; and
    (f) the filling factor multiplies the Young's modulus of the spacer is equal to 2 MPa or larger;
  xiii. the adaptor comprising: (a) a housing, (b) attachment on the housing that allows the adaptor to attached to a mobile phone with a camera, (c) a slot in the housing that allows (1) the plates in a closed configuration to slide into the slot and (2) when the plates are in the slot, at least a part of the sample area is less 2 cm away from the outer surface of the camera, and (d) an optical system in the housing configured to have at least a part of the sample contact area be imaged by the camera;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA3. A method for analyzing white blood cells in a blood sample, comprising:
  (a) obtaining a blood sample;
  (b) obtaining a device of AA1 or AA2;
  (c) depositing the blood sample on one or both of the plates when the plates are configured in an open configuration,
  (d) after (c), forcing the two plates into a closed configuration; and
  (e) capturing images of sample in the layer of uniform thickness while the plates are the closed configuration; and
  (i) analyzing the images to determine the number of white blood cells;
  wherein the filling factor is the ratio of the spacer contact area (on the plate) to the total plate area.

BB1. The device or method of any AA embodiments, wherein the pillar height is in the range of 5 to 15 um, BB2. The device or method of any AA embodiments, wherein the pillar height is in the range of 8 to 12 um, BB3. The device or method of any AA embodiments, wherein the pillar height is around 10 um.
BB4. The device or method of any AA embodiments, wherein the device is configured to count the white blood cells.
BB5. The device or method of any AA embodiments, wherein the device is configured to count the white blood cells sub-types (including neutrophils, eosinophils, basophils, lymphocytes, and monocytes),
BB6. The device or method of any AA embodiments, wherein spacer height is in the range of 7.5 um to 10.5 um.
BB7. The device or method of any AA embodiments, wherein spacer height is in the range of 9.5 um to 12.5 um.
BB8. The device or method of any AA embodiments, wherein spacer height is in the range of 11.5 um to 13.5 um.
BB9. The device or method of any AA embodiments, wherein spacer height is in the range of 12.5 um to 14.5 um.
BB10. The device or method of any AA embodiments, wherein spacer height is in the range of 13.5 um to 16 um.
BB11. The device or method of any AA embodiments, wherein a preferred field of view for counting and differentiating WBCs is 0.1 $mm^2$, 10 $mm^2$, 50 $mm^2$, 100 $mm^2$ or a range between any two of the values;
BB12. The device or method of any AA embodiments, wherein when the gap size of device is 10 um, the FoV is larger than 36 $mm^2$, thereby the WBC counting and differentiate accuracy is less than 5%.
BB13. The device or method of any AA embodiments, wherein when the gap size of device is 10 um, the FoV is larger than 16 $mm^2$, thereby the WBC counting and differentiate accuracy is less than 10%.
BB14. The device or method of any AA embodiments, wherein when the gap size of device is 10 um, the FoV is larger than 2 $mm^2$, thereby the WBC counting and differentiate accuracy is less than 20%.
BB15. The device or method of any AA embodiments, wherein a field of view is 0.1 $mm^2$ to 10 $mm^2$, preferred gap size of device is in the range of 10 um to 30 um, 30 um to 50 um, thereby the counting and differentiate accuracy is less than 10%.
BB16. The device or method of any AA embodiments, wherein field of view is 0.1 $mm^2$ to 10 $mm^2$, preferred gap size of device is in the range of 10 um to 30 um, thereby the counting and differentiate accuracy is less than 20%.
BB17. The device or method of any AA embodiments, wherein field of view is 10 $mm^2$ to 50 $mm^2$, preferred gap size of device is in the range of 5 um to 10 um, 10 um to 30 um, thereby the counting and differentiate accuracy is less than 10%.
BB18. The device or method of any AA embodiments, wherein field of view is 10 $mm^2$ to 50 $mm^2$, preferred gap size of device is in the range of 2 um to 5 um, 5 um to 10 um, 10 um to 30 um, thereby the counting and differentiate accuracy is less than 20%.
BB19. The device or method of any AA embodiments, wherein field of view is field of view of 50 $mm^2$ to 100 $mm^2$, preferred gap size of device is in the range of 2 um to 5 um, 5 um to 10 um, 10 um to 30 um, 30 um to 50 um thereby the counting and differentiate accuracy is less than 10%.
BB20. The device or method of any AA embodiments, wherein the spacer has a height in the range of 2 um to 5 um, thereby the WBCs missing counting is less than 15%.
BB21. The device or method of any AA embodiments, wherein the spacer has a height of 2 um to 5 um, 5 um to 10 um, thereby the WBCs missing counting is less than 30%.
BB22. The device or method of any AA embodiments, wherein the spacer has a height of preferred range of 2 um to 5 um, 5 um to 10 um, 10 um to 30 um thereby the WBCs missing counting is less than 60%.
BB23. The device or method of any AA embodiments, wherein the sample to phone lens distance is in the range of 2 mm to 5 mm.
BB24. The device or method of any AA embodiments, wherein the sample to phone lens distance is in the range of 4 mm to 7 mm.
BB25. The device or method of any AA embodiments, wherein the sample to phone lens distance is in the range of 6 mm to 9 mm.
BB26. The device or method of any AA embodiments, wherein the sample to phone lens distance is in the range of 8 mm to 11 mm.
BB27. The device or method of any AA embodiments, wherein the sample to phone lens distance is in the range of 10 mm to 13 mm.
BB28. The device or method of any AA embodiments, wherein the sample to phone lens distance is in the range of 12 mm to 15 mm.

Other Embodiments and Related Disclosure

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

D. Test Kit, Device, and Method

It should be noted that the Figures do not intend to show the elements in strict proportion. For clarity purposes, some elements are enlarged when illustrated in the Figures. The dimensions of the elements should be delineated from the descriptions herein provided and incorporated by reference.

Figure 18:
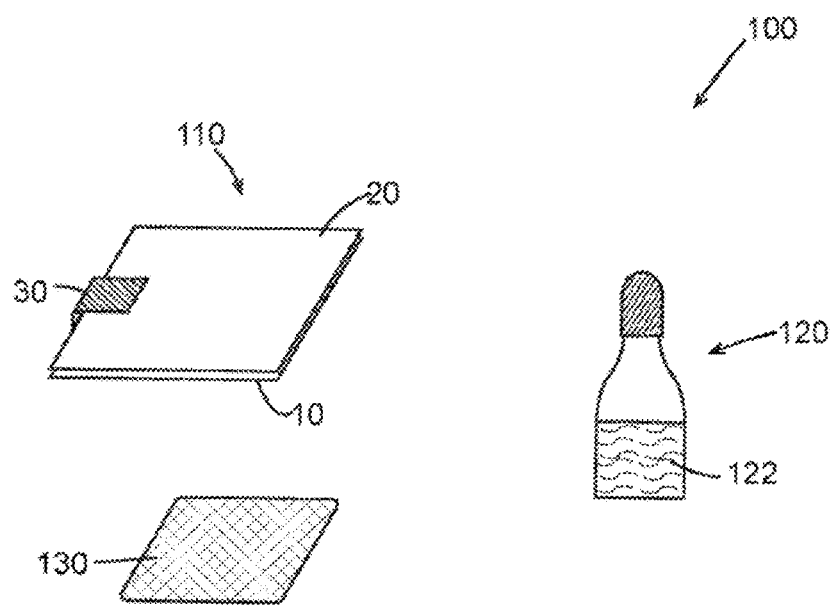
FIG. 18 shows an embodiment of the test kit of the present invention; the test kit includes a testing unit that has a first plate and a second plate, a swab, and a medium container that contains testing medium.

FIG. 18 shows an embodiment of the test kit 100 of the present invention. As shown in FIG. 18, the test kit 100 may comprise: a testing unit 110 that has a first plate 10 and a second plate 20, a swab 130, and a medium container 120 that contains testing medium 122.

The kit 100 of the present invention may be used to collect sample or specimen and perform tests of the collected sample or specimen. In some embodiments, the kit may be used for detecting a pathogenic disease in a subject. Here the term "subject" may refer to human or animal. In certain embodiments, the subject is a person.

As shown in FIG. 18, the testing unit may comprise a first plate 10, a second plate 20, wherein the first plate 10 and the second plate 20 are connected by a hinge 30 so that the two plates may pivot against each other. As shown in FIG. 18, the kit may comprise a swab 130, which may be used to collect a sample or specimen from the subject. The swab 130 may be an absorbent pad or piece of material having variable shape and size. In some embodiments, the swab may be made absorbent material such as but not limited to filter papers, absorbent polymers (e.g. polypropylene and polymethysiloxan polyhydrate), sponge, cellulose fiber, desiccant, or a combination thereof. In certain embodiments, the swab may be a cotton swab, which includes a small wad of cotton on the end of a short rod.

As shown in FIG. 18, the kit 100 of the present invention may include a container 62 that contains a testing medium 60. The container 120 may be any type of bottle, can, flask, pot, jug, cup, pouch, or any apparatus that can be used to withhold and dispense a liquid. In some embodiments, the container 62 may be a bottle or pouch. In certain embodiments, the container 120 may include a cap or seal; in certain embodiments, the container 120 may be used to directly dispense/deposit the testing medium 122 to a specific location.

In some embodiments, the swab 130 may be a swab strip, which has a flat, paper-like body. In certain embodiments, the swab strip may have a shape of rectangle, square, round, trapezoid, diamond, pentagon, hexagon, or other shapes. The lateral area of the swab strip may be less than 100 cm$^2$, 50 cm$^2$, 20 cm$^2$, 10 cm$^2$, 5 cm$^2$, 2 cm$^2$, 1 cm$^2$, 0.5 cm$^2$, 0.2 cm$^2$, 0. cm$^2$, 75 mm$^2$, 50 mm$^2$, 40 mm$^2$, 30 mm$^2$, 20 mm$^2$, 10 mm$^2$, 5 mm$^2$, 4 mm$^2$, 3 mm$^2$, 2 mm$^2$, 1 mm$^2$, 0.5 mm$^2$, or 0.1 mm$^2$, or in a range between any of the two values.

The kit 100 of the present invention may be used to detect one or more diseases. In some embodiments, the disease may be a pathogenic disease, which is caused by pathogens or infectious agents like bacteria, fungi, parasites, and viruses. In some embodiments, the disease may be a sexually transmitted disease (STD). In certain embodiments, the STD may be *Chlamydia*, gonorrhea, genital herpes, HIV/AIDS, human papillomavirus (HPV) infection, syphilis, bacterial vaginosis, trichomoniasis, or viral hepatitis.

In some embodiments, the pathogen of the disease to be detected may be bacteria, viruses, fungi, or parasites. In some embodiments, the pathogen may be *Chlamydia trachomatis, Neisseria gonorrhoeae*, herpes simplex virus (HSV), human immunodeficiency virus (HIV), human papillomavirus (HPV), *Treponema pallidum, Trichomonas vaginalis*, or hepatitis virus. In some embodiments, the pathogen is a bacterium; specifically in certain embodiments, the bacterium may be *Chlamydia trachomatis, Neisseria gonorrhoeae*, and *Treponema pallidum*. In some embodiments, the pathogen is a parasite; in certain embodiments, the parasite is *Trichomonas vaginalis*. In some embodiments, the pathogen is a virus; in certain embodiments, the virus is HSV, HIV, HPV or hepatitis virus.

Figure 19:
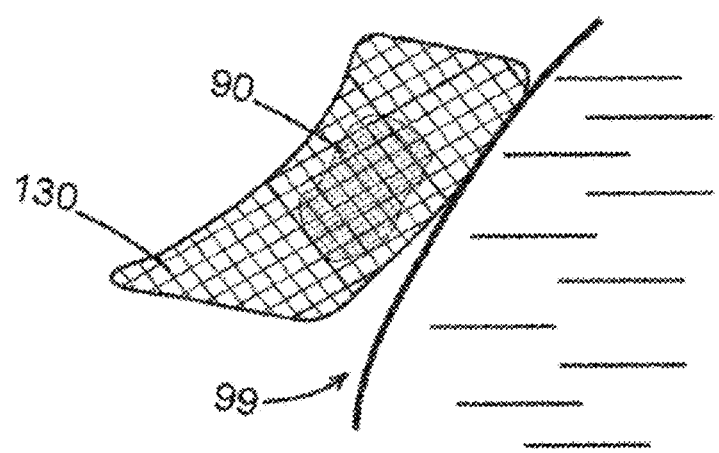
FIG. 19 illustrates a sample collection process in which the swab is used to swab a body part of a subject.
Figure 20:
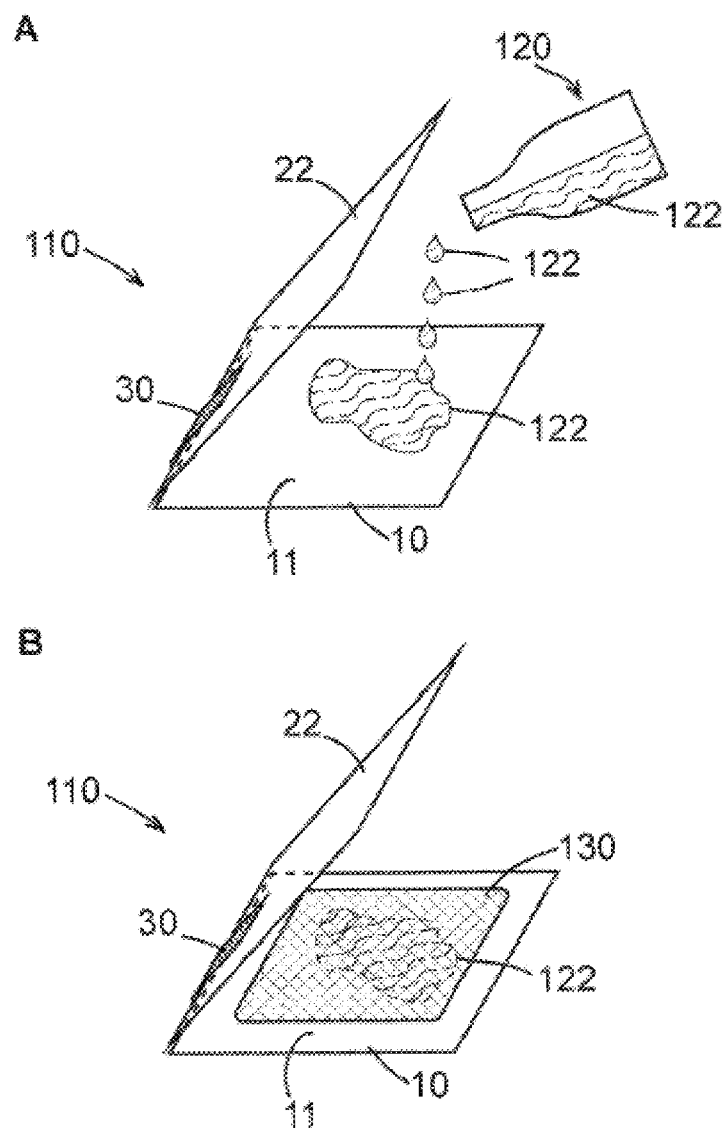
FIG. 20 shows perspective views of the testing unit in an open configuration when the sample is being deposited; panel (A) shows applying the testing medium to the first plate; and panel (B) shows placing the swab, together with the collected sample, on the first plate so that the swab is in contact with the applied testing medium.
Figure 21:
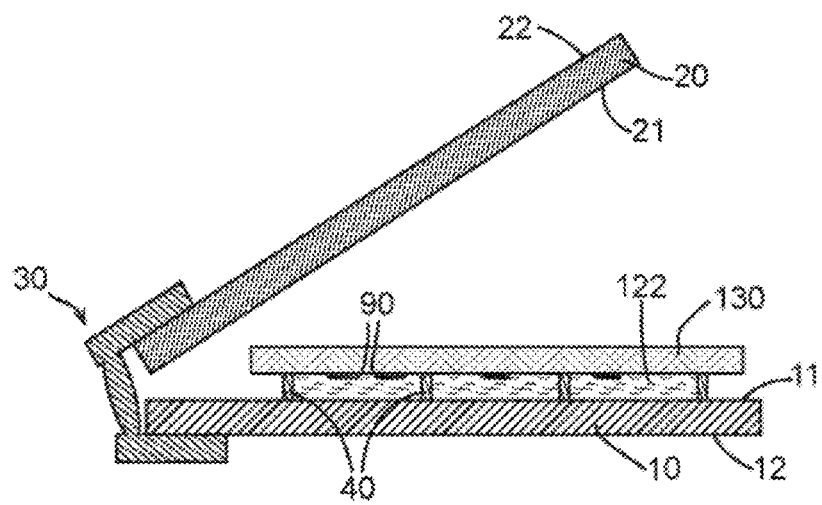
FIG. 21 shows sectional views of testing unit in the open and closed configurations after the swab has been placed and the testing medium has been applied; panel (A) shows the open configuration; and panel (B) shows the closed configuration, in which the swab has been pressed by the two plates and the testing medium has been mixed with the sample to form a mixture that is compressed into a thin layer.
Figure 21:
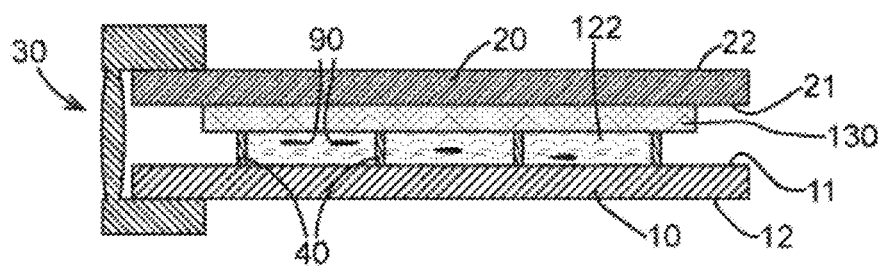

FIGS. 19-21 illustrates a process in which the kit 100 of the present invention is used to collect a sample and detect a pathogen so that a determination can be made regarding whether the subject being tested has a particular disease. In various embodiments, the specific steps in the process may be omitted, augmented, adjusted and/or altered so that the process may be more sensitive, convenient, easy to access, inexpensive, and/or accurate.

FIG. 19 illustrates a sample collection process in which the swab 130 is used to swab a body part 99 of a subject. The body part 99 may be any part of a human or animal body. In some embodiments, the swab 130 may be applied to exterior area (e.g. exposed skin) of the body or cavities (e.g. mouth or vagina) directly accessible from the exterior. In some embodiments, the body part 99 may be a genital (reproductive organ) or areas in close proximity to the genital area of a person. For example, in certain embodiments, the body part 99 may be the penis, testicles, scrotum, or skin or cavity (e.g. anus) close to the genital area of a male; in certain embodiments, the body part 99 may the cervix, clitoris, labia, vulva, vagina, or skin or cavity (e.g. anus) close to the genital area of a female. In certain embodiments, the body part 99 may be any part of the body where lesions, rashes, nodules, infection sites or body discharges are likely to be located or has been located. For example, in female gonorrhea patients or females suspected of having gonorrhea, the swab 130 may be used to swab the vagina of the subject being tested to collect vaginal fluid as a sample to be deposited on one or both of the plates in the testing unit 110.

As shown in FIG. 19, the swab 130 may be used to collect the sample 90 from the body part 99 of a subject. The specific process of collecting the sample may vary according to the type, location and structure of the body part 99, the size, shape and material of the swab 130, and/or the condition (e.g. liquid or solid) of the sample. For example, certain STD may result in lesions around the genital area; in such cases a swab strip may be used to wipe the genital area to collect excreted body fluids that may contain the pathogen.

FIG. 20 shows perspective views of the testing unit 110 in an open configuration when the testing medium 122 is being applied and the sample is being deposited; panel (A) shows applying the testing medium 122 to the first plate 10; and panel (B) shows placing the swab 130, together with the collected sample (not marked), on the first plate 10 so that the swab 130 (an the sample attached thereto) is in contact with the applied testing medium 122.

As shown in panel (A) of FIG. 20, the first plates 10 has an inner surface 11 and an outer surface (not shown) and the second plate 20 has an inner surface (not shown) and an outer surface 22. Referring to panels (A) and (B) of FIG. 20, in an open configuration, the first plate 10 and the second plate 20 are partially or entirely separated apart, allowing a sample and/or medium to be deposited on one or both of the plates.

The testing unit 110 may also include spacers (not shown) that may control the spacing between the plates when the testing unit 110 is in a closed configuration, in which the inner surfaces of the first plate 10 and the second plate 20 face each and the spacing between the plates is a thin gap, the height of which is regulated by the height of the spacers. In some embodiments, the testing unit 110 of the present invention may include but not be limited to the QMAX device (also termed as "CROF" device) described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

As shown in panels (A) and FIG. 20 and also referring to FIG. 18, the first plate 10 and the second plate 20 are connected by a hinge 30, which allows the first plate 10 and the second plate 20 to pivot against each other. It should also be noted that the specific design of the testing unit 110 may vary. For example, in some embodiments, the testing unit 110 may comprise the first plate 10 and the second plate 20 that not connected by any structure in an open configuration; the hinge 30 may be optional. In addition, the specific design the hinge 30 may vary; while FIGS. 18 and 20 shows that the hinge 30 covers the aligned edges of the first plate 10 and the second plate 20, the positioning and connection of the hinge 30 may be changed as long as the first plate 10 and the second plate 20 can be switched between an open configuration and a closed configuration, in which inner surfaces of the two plates face each other and are capable of compressing a sample into a thin layer. For example, in certain embodiments the hinge 30 include a first leaf that is connected to the outer surface of the second plate 20 and a second leaf that is connected to the inner surface of the first plate 10, while there are no aligned edges in the plates. As long as the hinge 30 permits effective switch between the open configuration and the closed configuration, the relative positioning and connectivity of the hinge 30 with the first plate 10 and the second plate 20 may vary.

As shown by panel (A) of FIG. 20, the container 120 may be used to apply the testing medium 122 onto the inner surface 11 of the first plate 10. The term "apply" here may mean deposit, drip, project, emit, smear or wipe. In some embodiments, the testing medium 122 may be applied directed from the container 120; in other embodiments, a transfer device, e.g. pipette, may be used to transfer the testing medium 122 from the container 120 to the specified location, e.g. the inner surface of the first plate 10. In some embodiments, the testing medium 122 may be applied directed by human hand exerting a force on the container 120. For example, in certain embodiments, the container 120 may be a flexible bottle and a user (e.g. the subject being tested or a person administering the test) may squeeze the container 120 and apply the testing medium 122 to the plate.

The inner surfaces of the first plate 10 and the second plate 20 may respectively include sample contact areas (not marked in FIG. 20) that may occupy a part or an entirety of the inner surfaces. The testing medium may be applied to the sample contact areas. Although panel (A) of FIG. 20 shows that testing medium 122 is applied to the first plate 10, it should be noted that the testing medium 122 may also be applied to the second plate 20 or to both of the plates. In some embodiments, one or both of the plates may comprise spacers (not shown) that are fixed to one or both of the plates. In certain embodiments, the spacers are in the sample contact areas and at least a portion of the spacers are in the area covered by the testing medium 122 applied to the plate(s).

Panel (B) of FIG. 20 shows that the swab 130 is placed on the first plate 10. The swab 130 may be swab strip that is a thin, absorbent layer. In some embodiments, the sample has been collected and are attached to the swab 130; in certain embodiments, the sample may be body fluid that has been absorbed into the swab 130; in certain embodiments, the sample may be in a solid condition and may be attached to a surface of the swab 130. In some embodiments, the swab 130 may be placed on the first plate 10 so that the surface of the swab 130 that directly contacted the body part is facing the inner surface 11 of the first plate 10; in some embodiment, the swab 130 may be placed on the first plate 10 so that the surface of the swab 130 that did not directly contact the body part is facing the inner surface 11 of the first plate 10. In some embodiments, the swab 130 may be placed on the second plate 20. For example, in certain embodiments the testing medium 122 is applied to the first plate 10 and the swab 130 is placed on the second plate 20 in the open configuration; the testing medium 122 and the swab 130 (and thus the sample on the swab) get into contact only after the first plate 10 and the second plate 20 are being switched to the closed configuration.

Although panel (B) of FIG. 20 shows that the swab 130 covers the testing medium 122 on the first plate 10, the swab 130 may be placed on the first plate 10 before or after the testing medium 122 is applied. For example, in certain embodiments the swab 130 may first be placed on the inner surface 11 of the first plate 10, then the testing medium 122 may be applied directly on top of the swab 130; in other embodiments, the swab 130 may be placed on the inner surface 11 of the first plate 10, the testing medium 122 may be applied to the second plate 20, and the swab 130 (and thus the sample) gets into contact with the testing medium 122 when the plates are being switched to the closed configuration.

In some specific embodiments, the testing medium 122 is applied to the inner surface 11 of the second plate 20; the swab 130 is placed on top of the testing medium 122, with the surface of the swab 130 that directly contacted the body part 99 facing the testing medium 122. In other specific embodiments, the swab 130 is placed first on the first plate 10, with the surface of the swab 130 that directly contacted the body part 99 facing the inner surface 11; then the testing medium 122 is applied to the surface of the swab 130 that did not contact the body part 99.

As indicated above, the size, shape and material of the swab 130 may vary. In addition, the specific process to deposit the collected sample onto one or both of the plates may also vary. For example, in certain embodiments, since it may be unnecessary to place the entire swab 130 onto the plate(s), the user may place only part of the swab 130 on the plate(s). In some embodiments, the swab 130 is not placed onto the plate(s); instead, the user may touch one or both of the plates with the swab 130 and transfer and/or smear part or all of the sample 90 onto the plate(s). In certain embodiments, the user may dip the swab 130 into a liquid, which may or may not be the testing medium 122, so that part or all of the sample 90 may be mixed into the liquid; then part of the mixture may be transferred/smeared onto one or both of the plates.

FIG. 21 shows sectional views of the testing unit 110 in the open and closed configurations after the swab 130 has been placed and the testing medium 122 has been applied. As shown in FIG. 21, the testing unit 110 may comprise a first plate 10, a second plate 20, and a hinge 30 that connects the first plate 10 and the second plate 20; the first plate 10 may comprise an outer surface 12 and an inner surface 11; the second plate 20 may comprise and outer surface 22 and an inner surface 21; the first plate 10 may further comprise spacers 40. It should be noted, however, the spacers 40 may be part of either the first plate 10, the second plate 20, or both plates. In some embodiments, the spacers 40 are fixed on one or both of the plates.

Panel (A) of FIG. 21 shows the first plate 10 and the second plate 20, which are movable relative to each other into different configurations, in the open configuration. As shown in panel (A), in the open configuration, the first plate 10 and the second plate 20 are partially or entirely separately apart, and the spacing between the two plates are not regulated by the spacers 40.

Panel (A) shows a specific embodiment, in which the testing medium 122 has been applied to the inner surface 11 of the first plate 10 and the swab 130 has been placed on top of the testing medium 122; in this specific embodiment, at least part of the sample 90 is present on the lower surface of the swab 130 because that is the surface that directly contacted the body part 99 during swabbing. It should be noted, however, that the specific sequence of apply testing medium 122 and placing the swab 130 may vary, as indicated above. In addition, in certain embodiments the swab 130 may be used to transfer and/or smear the sample 90 onto the plate(s) and the swab 130 is not placed on top of the plate(s).

Panel (B) of FIG. 21 shows the testing unit 110 in the closed configuration, in which the swab 130 has been pressed by the two plates 10 and 20 and the testing medium 122 has been mixed with the sample 90 to form a mixture that is compressed into a thin layer. It should be noted that, as soon as when the testing medium 122 is in contact with the sample 90, the mixing has started without pressing the plates. In some embodiments, however, switching the plates to the closed configuration may speed up the mixing process because the thickness of the liquid layer has been reduced. The mixing may rely on diffusion or other mechanism (e.g. specific binding between components of the testing medium and the components of the sample) or a combination thereof.

In some embodiments, to facilitate the mixing of the sample 90 and the testing medium 122, the inner surface 11 of the first plate 10 may be hydrophilic. In certain embodiments, the inner surface 11 of the first plate 10 may be hydrophilic and the inner surface 21 of the second plate 20 may be hydrophobic. If the testing medium 122 is not water-based, in some embodiments the inner surface 11 of the first plate 10 may be hydrophobic.

The testing medium 122 may be used to facilitate the distribution, imaging, visualization, identification, quantification and/or analysis of the pathogen that may or may not be present in the sample 90. In some embodiments, the testing medium 122 may comprise a staining reagent, which may stain the target pathogen so that the pathogen may be imaged, visualized, identified, quantified and/or analyzed. For example, in certain embodiments the testing medium may comprise Gram staining reagents which may be used to stain and differentiate bacteria species; further imaging, visualization, identification, quantification and/or analysis may be conducted after the staining without or without further differentiation based on cell size and/or morphology.

After the analyte (e.g. cells) is stained, or in any way produces a detectable signal, the signal is to be detected. For example, when the analyte is stained with the staining reagent, either with a color metric method or with a fluorescent label, the image(s) of the analyte can be taken by a camera, and the image(s) can be analyzed, e.g. by counting the number of stained analytes and/or measuring the intensity of the signal.

In some embodiments, the testing medium 122 may comprise a specific binding reagent to the pathogen. For example, in certain embodiments the specific binding reagent may be an antibody (e.g. monoclonal antibody) that specifically binds to the pathogen. In some embodiments, the testing medium 122 may further comprise a signaling reagent, e.g. a detectable label; for example, in certain embodiments an antibody may be conjugated with an optical detectable label so that a signal may be produced upon the being between the antibody and the pathogen. In certain embodiments, the analyte can be detected and/or measured with an immunoassay. In some embodiments, the specific binding reagent may be a modified or unmodified nucleotide, e.g. DNA. In certain embodiments, the analyte can be detected and/or measured with a nucleic acid (e.g. DNA) hybridization assay.

In some embodiments, the testing medium 122 may be used to facilitate the distribution of the sample 90, and in particular the pathogen in the sample 90. For example, in some embodiments the testing medium 122 may be a buffer solution that dilutes the sample 90 or allow the pathogen in the sample 90 to be distributed more freely. In certain embodiments, the testing unit 110 may comprise binding/detection sites on the inner surfaces of the plates, e.g. inner surface 11 of the first plate 10. Such binding/detection sites may be coated with binding/detection reagents, e.g. antibodies or antibody conjugated with detectable labels, so that when the sites are in contact with the mixture of the sample 90 and the testing medium 122, the pathogen in the sample 90 may be bound and/or detected. In some embodiments, the pathogen may be immobilized on the binding/detection sites; in certain embodiments, the binding/detections sites may be washed to remove non-specific binding.

In some embodiments, the detection of the pathogen in the sample 90 may require reagents from both the testing medium 122 and the bind/detection sites on one or both of the inner surfaces of the plates. For example, in certain embodiments the binding/detection sites may comprise a first antibody that specifically binds to the pathogen, and the testing medium 122 may comprise a signaling reagent to produces a signal upon recognizing/binding of the first antibody/pathogen complex.

In some embodiments, after the compressing of the first plate 10 and the second plate 20 with the swab 130 in between, the mixture of the sample 90 and the testing medium 122 may be analyzed directly without removing the swab 130. In the closed configuration, the mixture of the sample 90 and the testing medium 122 may be compressed into a thin layer, facilitating the mixing and the analysis.

In some embodiments, after the compressing of the first plate 10 and the second plate 20 with the swab 130 in between, the testing unit 110 may be again reverted to an open configuration, allowing the removal of the swab 130; in certain embodiments, washes may or may not be conducted to reduce signaling from non-specific binding. After the removal of the swab 130 and/or washing, the testing unit 110 may be changed to the closed configuration, wherein the mixture of the sample 90 and the testing medium 122 may be compressed into a thin layer.

In some embodiments, the spacers 40 may regulate the thickness of the layer of mixture. In some embodiments, the thickness may be less than 5 mm, 2 mm, 1 mm, 900 µm, 800 µm, 700 µm, 600 µm, 500 µm, 400 µm, 300 µm, 200 µm, 175 µm, 150 µm, 125 µm, 100 µm, 90 µm, 80 µm, 75 µm, 70 µm, 60 µm, 50 µm, 40 µm, 30 µm, 25 µm, 20 µm, 15 µm, 10 µm, 9 µm, 8 µm, 7 µm, 6 µm, 5 µm, 4 µm, 3 µm, 2.5 µm, 2 µm, 1.8 µm, 1.5 µm, 1 µm, 0.8 µm, 0.5 µm, 0.2 µm, 0.1 µm, or 0.05 µm, or in a range between any of the two values.

Examples of Present Invention

A1. A test kit for detecting a pathogenic disease in a subject, comprising:
   i. a first plate and a second plate, wherein the plates are configured to move relative to each other into different configurations;
   ii. a swab configured to collect a sample by swabbing a body part of the subject; and
   iii. a container that contains a testing medium,
     wherein one of the configurations is an open configuration, in which the two plates are partially or entirely separated apart, allowing the swab with the collected sample to be placed on the first plate, the swab being in contact with the testing medium, which is applied before or after the placement of the swab;
     wherein another of the configuration is a closed configuration, which is configured after the swab and the testing medium are in contact; and in the closed configuration: the two plates are pressed against the swab and the testing medium, forming a mixture of the sample and the testing medium, wherein the mixture is compressed into a thin layer; and
     wherein the testing medium is configured to detect a pathogen in the sample.

A2. The test kit of embodiment A1, wherein the disease is an infectious disease.

A3. The test kit of embodiment A1 or A2, wherein the disease is a sexually transmitted disease (STD).

A4. The test kit of any prior embodiments, wherein the disease is selected from the group consisting of: *Chlamydia*, gonorrhea, genital herpes, HIV/AIDS, human papillomavirus (HPV) infection, syphilis, bacterial vaginosis, trichomoniasis, and viral hepatitis.

A5. The test kit of any prior embodiments, wherein the pathogen is a selected from the group consisting of: *Chlamydia trachomatis, Neisseria gonorrhoeae*, herpes simplex virus (HSV), human immunodeficiency virus (HIV), human papillomavirus (HPV), *Treponema pallidum, Trichomonas vaginalis*, and hepatitis virus.

A6. The test kit of embodiment A1, wherein the pathogen is a bacterium.

A7. The test kit of embodiment A6, wherein the bacterium is selected from the group consisting of: *Chlamydia trachomatis, Neisseria gonorrhoeae*, and *Treponema pallidum*.

A8. The test kit of embodiment A1, wherein the pathogen is a virus.

A9. The test kit of embodiment A8, wherein the virus is selected from the group consisting of: herpes simplex virus (HSV), human immunodeficiency virus (HIV), human papillomavirus (HPV), and hepatitis virus.

A10. The test kit of any prior embodiments, wherein the swab is a swab strip.

A11. The test kit of any prior embodiments, wherein the body part is the genital of the subject.

A12. The test kit of any prior embodiments, wherein the testing medium comprises a specific binding reagent to the pathogen.

A13. The test kit of embodiment A12, wherein the specific binding reagent is an antibody.

A14. The test kit of embodiment A12, wherein the testing medium further comprises a signaling reagent.

A15. The test kit of embodiment A1, wherein an inner surface of the first plate or the second plate is coated with a signaling reagent.

A16. The test kit of embodiment A14 or A15, wherein the signaling reagent is configured to produce a signal upon the binding of the binding reagent to the pathogen.

A17. The test kit of any prior embodiments, wherein the testing medium comprises a staining reagent.

A18. The test kit of embodiment A1, wherein an inner surface of the first plate or the second plate is coated with a staining reagent.

A19. The kit of embodiment A17 or A18, wherein the staining reagent is configured to stain the pathogen to: (1) product a detectable signal, or (2) allow the pathogen to be bound by another reagent that produce a detectable signal.

A20. The test kit of any prior embodiments, wherein one of the plates comprises spacers that are fixed to one of the plates, and in the closed configuration: the spacing between the plates are regulated by the spacers.

A21. The test kit of embodiment A17, wherein the thickness of the thin layer is regulated by the spacers and is less than 200 μm.

A22. The test kit of any prior embodiments, wherein the kit is configured to conduct diagnostic testing, health monitoring, and/or preventive testing.

A23. The test kit of any prior embodiments, further comprising hardware that are configured to receive and process a detected signal from the mixture of the sample and the testing medium.

A24. The test kit of any prior embodiments, wherein the testing medium is applied to an inner surface of the first plate, and the inner surface is hydrophilic.

A25. The test kit of any prior embodiments, wherein the testing medium comprises a nucleic acid configured to bind to the analyte.

B1. A method of detecting a pathogenic disease in a subject, comprising:
- (a) providing a first plate and a second plate, wherein the plates are configured to move relative to each other into different configurations;
- (b) collecting a sample by swabbing a body part of the subject;
- (c) placing the swab with the collected sample on the first plate when the two plates are in an open configuration, wherein the two plates are partially or entirely separated apart;
- (d) applying a testing medium before or after the placement of the swab, making the testing medium contact the swab and forming a mixture of the sample and the testing medium;
- (e) after steps (c) and (d), changing the plates into a closed configuration by pressing the plates against the mixture of the sample and the testing medium,
  - i. wherein the mixture is compressed into a thin layer, and
  - ii. the testing medium is configured to detect a pathogen in the sample and produce a signal upon detection of the signal,
- (f) determining if the subject has the disease by checking for the signal.

B2. The method of embodiment B1, wherein the testing medium comprises a binding reagent that specifically binds to the pathogen and signaling reagent that produces the signal upon binding of the binding reagent and the pathogen.

B3. The method of embodiment B1, further comprising removing the swab after steps (c) and (d).

B4. The method of embodiment B3, wherein the swab is removed after the testing medium and the sample are in contact for a time period sufficient for a substantial portion of the collected sample to mix with the testing medium.

B5. The method of embodiment B1, wherein the swab is not removed before step (e).

B6. The method of embodiment B1, further comprising removing the swab after step (e) and changing the plates into the closed configuration after the removal of the swab.

B7. The method of any B embodiments, further comprising imaging the analyte in the sample in the closed configuration.

E. Assays with Surface Patterns

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

A. Examples of QMAX Card that has Surface Guiding Patterns

To facilitate an assay, the present invention provides surface guiding patterns on the inner surface of the plates of QMAX Card. The function of the surface guiding pattern is to drop a sample in one place, and use lateral flow guiding patterns to flow a sample laterally from sample deposition zone to a reaction zone. Optionally, lateral filters can be placed between the sample deposition zone and the reaction zone.

The surface guiding patterns can have a height less the spacers or the sample as the spacers. In some embodiments, the spacers are a part of the surface guiding patterns.

Figure 22:
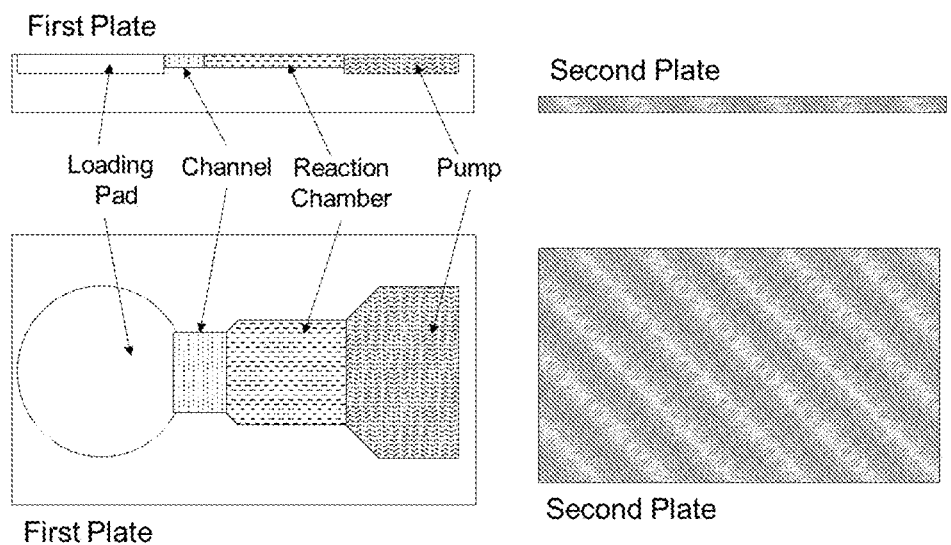
FIG. 22 shows a schematic drawing for an exemplary embodiment of the device with surface guiding pattern provided by the present invention.

FIG. 22. shows a schematic drawing for an exemplary embodiment of the device. (a) Side view and (b) top view show the device comprising a first plate, a second plate, and loading pad, channel, reaction chamber, and pump on the first plate.

Figure 23:
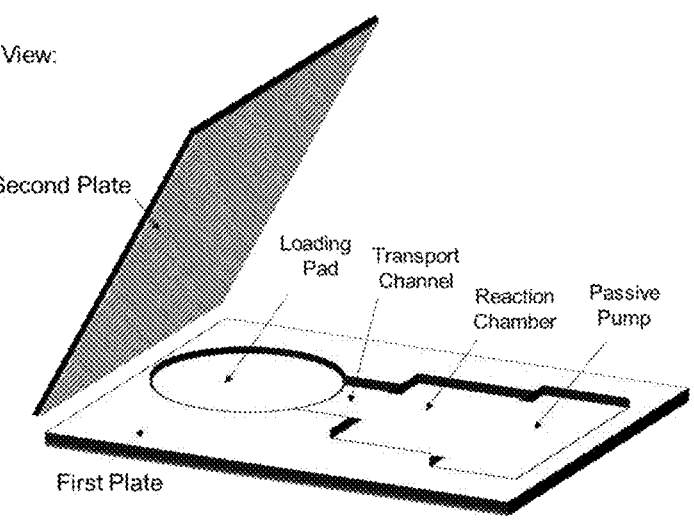
FIG. 23 shows another schematic drawing for an exemplary embodiment of the device with surface guiding pattern provided by the present invention.

FIG. 23 shows a schematic drawing for an exemplary embodiment of the device comprising a first plate, a second plate, and loading pad, channel, reaction chamber, and pump on the first plate.

Figure 24:
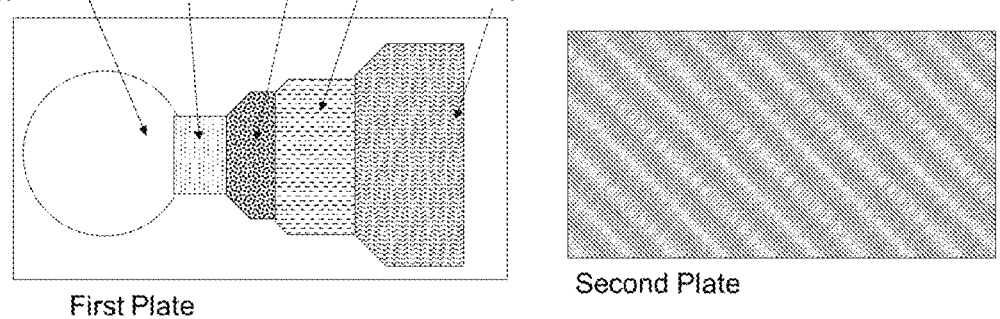
FIG. 24 shows another schematic drawing for an exemplary embodiment of the device with surface guiding pattern, which further comprises a filter.

FIG. 24 shows a schematic drawing for another exemplary embodiment of the device with a filter. (a) Side view and (b) top view show the device comprising a first plate, a second plate, and loading pad, channel, filter, reaction chamber, and passive pump (optional) on the first plate.

A method for using the QMAX card with surface guiding patterns for performing assay comprises (a) depositing a sample in the sample deposition zone, (b) letting the sample flow from the sample deposition zone to an reaction zone, and (c) close the second plate on top of the first plate.

Afterward, in some embodiments, the QMAX card is inserted into an optical adaptor for further measurement. The second plate that covers the first plate prevents a sample flowing out of the QMAX card.

Figure 25:
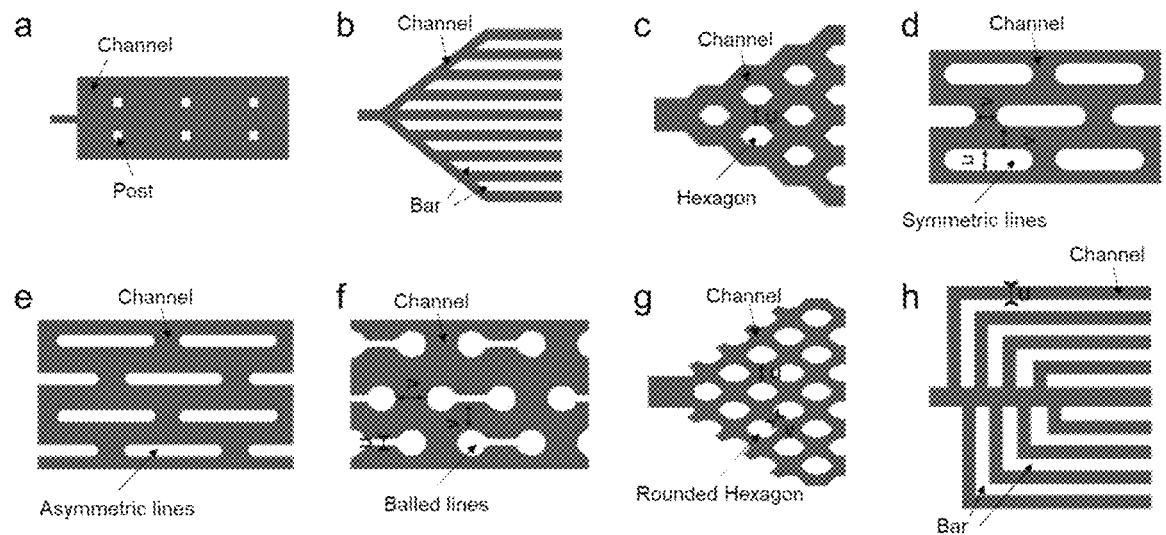
FIG. 25 shows examples of structures in the channel, filter chamber, reaction chamber and pump on the first plate of the device according to some embodiments of the present invention.

FIG. 25 shows examples of structures in the channel, filter chamber, reaction chamber and pump on the first plate, while white area is the structure and black area is the fluidic area.

Top view of structures: (a) "Posts" or pillar array; (b) "Tree lines a"; (c) "Hexagons"; (d) "Symmetric lines"; (e) "Asymmetric lines"; (f) "Balled lines"; (g) "Rounded and interlocked hexagons"; (h) "Tree lines b".

A-1. Properties of the Channel Structures

In some embodiments, the structures in the channel, filter chamber, reaction chamber and pump on the first plate contains: (a) "Posts" or pillar array; (b) "Tree lines a"; (c) "Hexagons"; (d) "Symmetric lines"; (e) "Asymmetric lines"; (f) "Balled lines"; (g) "Rounded and interlocked hexagons"; (h) "Tree lines b".

In some embodiments, the structures have shapes of line, sphere, rectangle, hexagon, symmetric lines, asymmetric lines and/or any other polyhedron or their combinations.

In some embodiments, the structure is periodic with lattice of square, hexagon, and/or any other lattices.

In some embodiments, the structure is aperiodic.

In some embodiments, the structure size (width and length) is in the range of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

In some embodiments, the structure period is in the range of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

In some embodiments, the structure depth is in the range of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

In some embodiments, the filter structure on first plate includes, but not limited to, weir filters, post filters, and membrane filters.

In some embodiments, for weir filters, which contain large barriers in channel to trap large cells, the barrier size is in the range of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

In some embodiments, for post filters, which contain an array of microposts to trap large cells, the structure dimensions is in the range of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

In some embodiments, for membrane filters, which contain an array of pores on the floor or ceiling to trap large cells, the pores size is in the range of 1 nm, 10 nm, 100 nm, 500 nm, 1 um, 5 um, 50 um, or a range between any two of the values; and a preferred range of 10 nm to 100 nm, 100 nm to 500 nm, 500 nm to 1 um, 1 um to 10 um, or 10 um to 50 um.

In some embodiments, the structure is hydrophilic, with liquid contact angle of 0°, 15°, 30°. 45°. 60°, 90°, or a range between any two of the values; and a preferred range of 0 to 15°, 15° to 300, 300 to 450°.

Figure 26:
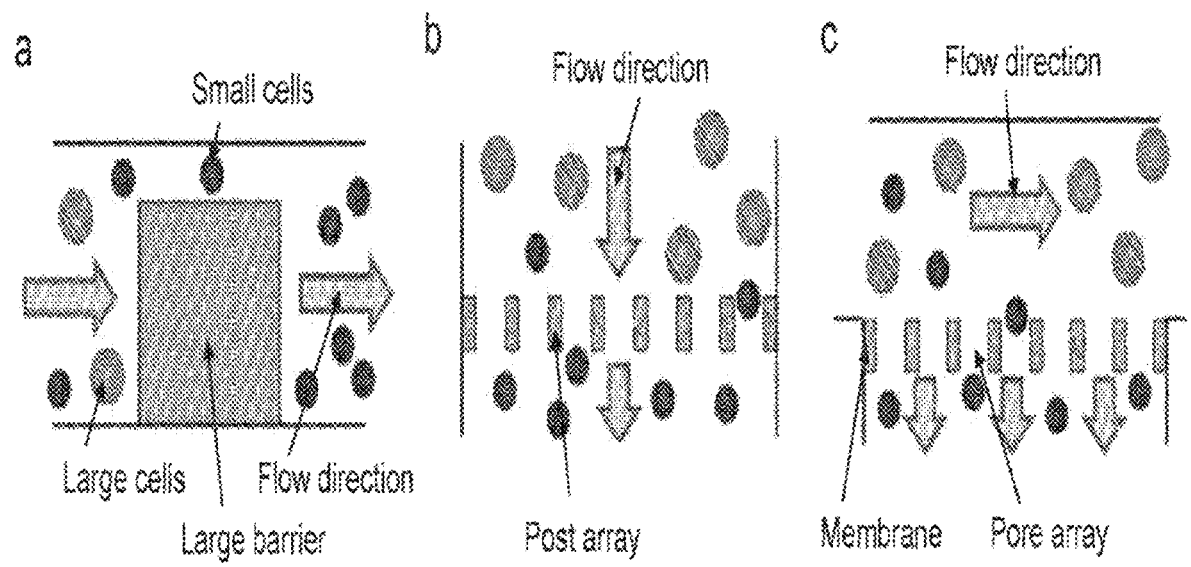
FIG. 26 shows more examples of filters on the first plate of the device according to some embodiments of the present invention.

FIG. 26 shows further examples of filters on first plate other than structures shown in FIG. 25, including (a) weir filters, which contain large barriers in channel to trap large cells; (b) post filters, which contain an array of microposts to trap large cells; and (c) membrane filters, which contain an array of pores on the floor or ceiling to trap large cells.

B. Examples of QMAX Card for Lateral Filtering

B-1. Filtering Device

Another aspect of the present invention is to provide a device for sample filtering.

In some embodiments, the device provided herein in Section B comprises features stated here alone. In some embodiments, the device provided in Section B comprises certain features described in Section A as well.

Figure 27:
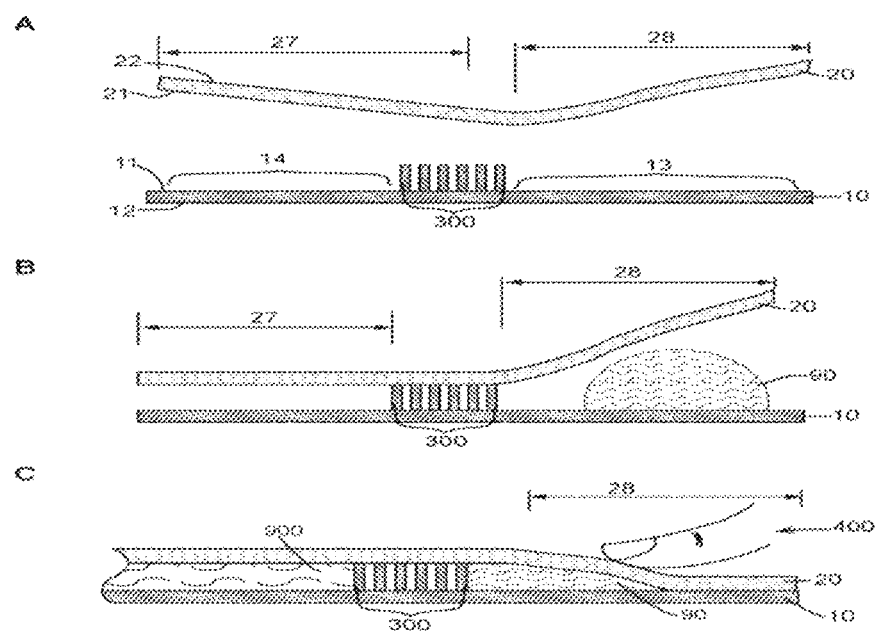
FIG. 27 shows schematically an exemplary embodiment of the device and method for lateral filtering provided by the present invention.

FIG. 27 schematically shows an exemplary embodiment of the device for sample filtering according to the present invention. More specifically, as shown in panel (A), the device comprises a first plate 10, a second plate 20, and a nanostructured filter 300. Both the first plate 10 and the second plate 20 comprise an inner surface, 11 and 21, respectively. The first plate comprises, on its inner surface 11, an unfiltered area 13 and a filtered area 14. The unfiltered area 13 is for contacting a composited liquid sample that contains a target-filtering component 92 that is to be removed by the device, and the filtered are 14 for contacting a filtering product of the sample in which the target-filtering component 92 is removed. The nanostructured filtered 300 is fixed to the first plate inner surface 11. It should be noted, however, in some embodiments, the nanostructured filter 300 is fixed to the second plate inner surface 21 or to the inner surfaces (11 and 21) of the two plates. As shown here, the second plate 20 is flexible. In some embodiments, the first plate 10 or both the two plates are flexible.

As shown in FIG. 27, the first plate 10 and the second plate 20 are movable relatively to each other into different configurations, including an open configuration and a closed configuration. FIG. 27 panels (A) and (B) depict different embodiments of the open configuration. In the open configuration, the first plate 10 and second plate 20 are partially separated, as shown in panel (B), or completely separated, as shown in panel (A). Moreover, in the open configuration, the spacing between the two plates allows a composite liquid sample 90 to be deposited on the unfiltered area 13, as shown in panel (B), and/or the second plate inner surface (not shown).

FIG. 27 panel (C) illustrates the closed configuration of the exemplary device and a human finger that facilitates the conversion of the device from the open configuration to the closed configuration. In particular, as shown in the figure, the human finger 600 provides a compressing force that compresses, over the unfiltered area 13, the first plate 10 and second plate 20 into the closed configuration. And during the process of bringing the plates from the open configuration to the closed configuration, the deposited sample 90 is compressed by the two plates and consequentially part of the sample 90 flows through the nanostructured filter 300 from the unfiltered area to the filtered area. The nanostructured filter 300 is configured to separate the target-filtering component 92 to be filtered from the part of the sample that arrives the filtered area, forming a filtering product 900. It should be pointed out that, in some embodiments, regardless whether the nanostructured filter 300 is fixed to the first plate inner surface 11 or the second plate inner surface 21, here the positioning of the nanostructured filter on the second plate is limited in a way that the nanostructured filter 300 is positioned between the unfiltered area 13 and the filtered area 14 at the closed configuration. With this structural relationship, it is thus configured that at least part of the sample 90 is forced at the closed configuration to flow through the nanostructured filter 300 in the direction from the unfiltered area 13 and the filtered area 14.

In some embodiments, the term "nanostructured filters" and the term "filter" as used in section A are interchangeable. In some embodiments, the nanostructured filter comprises the features of the filter as described in section A.

Open Configuration.

In some embodiments, in the open configuration, the two plates (i.e. the first plate and the second plate) are separated from each other. In certain embodiments, the two plates may have one edge connected together during all operations of the plates (including the open and closed configuration), the two plates open and close similar to a book. In some embodiments, the two plates have rectangle (or square) shape and have two sides of the rectangles connected together (e.g. with a hinge or similar connector) during all operations of the plates.

In some embodiments, the open configuration is a configuration that the plates are far away from each other, so that the sample is deposited onto one or both plates of the pair without any hindrance of the other plate. In some embodiments, when two sides of the plates are connected, the open configuration is a configuration that the plates form a wide angle (e.g. in the range of 60 to 180, 90 to 180, 120 to 180, or 150 to 180 degrees) so that the sample is deposited onto one plate of the pair without any hindrance of the other plate.

In some embodiments, the open configuration comprises a configuration that the plates are far way, so that the sample is directly deposited onto one plate, as if the other plate does not exist.

In some embodiments, the open configuration is a configuration that the pair of the plates are spaced apart by a distance at least 10 nm, at least 100 nm, at least 1000 nm, at least 0.01 cm, at least 0.1 cm, at least 0.5 cm, at least 1 cm, at least 2 cm, or at least 5 cm, or within a range of any two of the values.

In some embodiments, the two plates are connected by the nanostructured filter, and the open configuration is a configuration that the two plates are separated over the unfiltered area.

The two plates over the unfiltered area are spaced apart by a distance at least 10 nm, at least 100 nm, at least 1000 nm, at least 0.01 cm, at least 0.1 cm, at least 0.5 cm, at least 1 cm, at least 2 cm, or at least 5 cm, or within a range of any two of the values.

In some embodiments, the open configuration is a configuration that the pair of plates are oriented in different orientations. In some embodiments, the open configuration comprises a configuration that defines an access gap between the pair of plates that is configured to permit sample addition.

Closed Configuration.

In some embodiments, a closed configuration of the two plates is the configuration in which: the nanostructured filtered is positioned between the unfiltered area and the filtered area, and the spacing (i.e. the distance) between the inner surfaces of the two plates over the unfiltered area is reduced such that at least part of the deposited sample is compressed by the two plates to flow through the nanostructured filter from the unfiltered area to the filtered area. In some embodiments, the spacing between the two plates over the unfiltered area is significantly smaller than the unconfined thickness of the deposited sample. In some embodiments, the closed configuration is not related to whether the sample has been added to the plates.

During the process of bringing the plates from an open configuration to a closed configuration, the plates are facing each other (at least a part of the plates are facing each other) and a force is used to bring the two plates together. If a sample has been deposited, when the two plates are brought from an open configuration to a closed configuration, the inner surfaces of the two plates compress the sample deposited on the plate(s) to reduce the sample thickness (while the sample has an open flow laterally between the plates), and the thickness of a relevant volume of the sample is determined by the spacing between the two plates, and the method being used and by the sample mechanical/fluidic property. The thickness at a closed configuration can be predetermined for a given sample and given spacers, plates and plate pressing method.

In some embodiments, in the configuration, the spacing between the two plates over the unfiltered area is less than 10 nm, less than 100 nm, less than 1000 nm, less than 0.01 cm, less than 0.1 cm, less than 0.5 cm, less than 1 cm, less than 2 cm, or less than 5 cm, or within a range of any two of the values.

In some embodiments, during the process of bringing the plates from an open configuration to a closed configuration, the percentage of all the part of the deposited sample that is forced to flow through the nanostructured filter in the total volume of the deposited sample is at least 0.1%, at least 0.5%, at least 1%, at least 5%, at least 10%, at least 20%, at least 30%, at least 40%, at least 50%, at least 60%, at least 70%, at least 80%, at least 90%, at least 95%, at least 99%, or within any range of any two of these values.

In some embodiments, it would be possible to conformable press, either in parallel or sequentially, the QMAX device into a closed configuration. Conformable pressing is a method that makes the pressure applied over an area to be substantially constant regardless of the shape variation of the outer surfaces of the plates; In particular, parallel conformable pressing applies the pressures on the intended area at the same time, and sequential conformable pressing applies the pressure on a part of the intended area and gradually move to other area. Conformable pressing may be applied by human hand, air blow, liquid pressure, or other forces.

Plates. In the present invention, generally, the plates of CROF are made of any material that (i) is capable of being used to regulate, together with the spacers, part of all of the spacing between the plates and/or the thickness of a portion or entire volume of the sample, and (ii) has no significant adverse effects to a sample, an assay, or a goal that the plates intend to accomplish. However, in certain embodiments, particular materials (hence their properties) ae used for the plate to achieve certain objectives.

In some embodiments, the two plates have the same or different parameters for each of the following parameters: plate material, plate thickness, plate shape, plate area, plate flexibility, plate surface property, and plate optical transparency.

Plate materials.

In some embodiments, the plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1. The inorganic materials for any one of the plates include, but not limited to, glass, quartz, oxides, silicon-dioxide, silicon-nitride, hafnium oxide (HfO), aluminum oxide (AlO), semiconductors: (silicon, GaAs, GaN, etc.), metals (e.g. gold, silver, copper, aluminum, Ti, Ni, etc.), ceramics, or any combinations of thereof.

Mat-2 The organic materials for any one of the plates include, but not limited to, polymers (e.g. plastics) or amorphous organic materials. The polymer materials for the plates include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the plates are each independently made of at least one of glass, plastic, ceramic, and metal. In some embodiments, each plate independently includes at least one of glass, plastic, ceramic, and metal.

In some embodiments, one plate is different from the other plate in lateral area, thickness, shape, materials, or surface treatment. In some embodiments, one plate is the same as the other plate in lateral area, thickness, shape, materials, or surface treatment.

The materials for the plates are rigid, flexible or any flexibility between the two. The rigidity (i.e. stiff) or flexibility is relative to a give pressing forces used in bringing the plates into the closed configuration.

In some embodiments, a selection of rigid or flexible plate is determined from the requirements of controlling a uniformity of the sample thickness at the closed configuration.

In some embodiments, at least one of the two plates are transparent (to a light). In some embodiments at least a part or several parts of one plate or both plates are transparent. In some embodiments, the plates are non-transparent.

Plate Thickness.

In some embodiments, the average thickness for at least one of the plates is 2 nm or less, 10 nm or less, 100 nm or less, 200 nm or less, 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, or in a range between any two of the values.

In some embodiments, the average thickness for at least one of the plates is at most 3 mm (millimeter), at most 5 mm, at most 10 mm, at most 20 mm, at most 50 mm, at most 100 mm, at most 500 mm, or in a range between any two of the values.

In some embodiments, the average thickness for at least one of the plates is in the range of 1 to 1000 µm, 10 to 900 µm, 20 to 800 µm, 25 to 700 µm, 25 to 800 µm, 25 to 600 µm, 25 to 500 µm, 25 to 400 µm, 25 to 300 µm, 25 to 200 µm, 30 to 200 µm, 35 to 200 µm, 40 to 200 µm, 45 to 200 µm, or 50 to 200 µm. In some embodiments, the average thickness for at least one of the plates is in the range of 50 to 75 µm, 75 to 100 µm, 100 to 125 µm, 125 to 150 µm, 150 to 175 µm, or 175 to 200 µm. In some embodiments, the average thickness for at least one of the plates is about 50 µm, about 75 µm, about 100 µm, about 125 µm, about 150 µm, about 175 µm, or about 200 µm.

In some embodiments, the thickness of a plate is not uniform across the plate. Using a different plate thickness at different location may be used to control the plate bending, folding, sample thickness regulation, and others.

Plate Shape and Area.

Generally, the plates can have any shapes, as long as the shape allows a compress open flow of the sample and the regulation of the sample thickness. However, in certain embodiments, a particular shape may be advantageous. The shape of the plate may be round, elliptical, rectangles, triangles, polygons, ring-shaped, or any superpositions of these shapes.

In some embodiments, the two plates can have the same size and/or shape, or different size and/or shape. The area of the plates depends on the specific application. In some embodiments, the area of the plate is at most 1 mm$^2$ (square millimeter), at most 10 mm$^2$, at most 100 mm$^2$, at most 1 cm$^2$ (centimeter square), at most 2 cm$^2$, at most 5 cm$^2$, at most 10 cm$^2$, at most 100 cm$^2$, at most 500 cm$^2$, at most 1000 cm$^2$, at most 5000 cm$^2$, at most 10,000 cm$^2$, or over 10,000 cm$^2$, or any range between any of the two values.

In certain embodiments, at least one of the plate is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or in a range between any two of the values. The length can be as long it needed. The belt can be rolled into a roll.

Plate Surface Flatness.

In many embodiments, an inner surface of the plates is flat or significantly flat, planar. In certain embodiments, the two inner surfaces of the plates are, at the closed configuration, parallel with each other. Flat inner surfaces facilitate a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

The flatness of the plate surface is relative to the final sample thickness (the final thickness is the thickness at the closed configuration), and is often characterized by the term of "relative surface flatness," which is the ratio of the plate surface flatness variation to the final sample thickness.

In some embodiments, the relative surface flatness is less than 0.01%, 0.1%, less than 0.5%, less than 1%, less than 2%, less than 5%, less than 10%, less than 20%, less than 30%, less than 50%, less than 70%, less than 80%, less than 100%, or in a range between any two of these values.

Plate surface parallelness. In some embodiments, the two surfaces of the plate are significantly parallel with each other in the closed configuration. Here "significantly parallel" means that an angle formed but extensions of the two plates is less than 0.1, 0.2, 0.5, 1, 2, 3, 4, 5, 10, or 15 degrees. In certain embodiments, the two surfaces of the plate are not parallel with each other.

Plate flexibility. In some embodiments, a plate is flexible under the compressing of a CROF process. In some embodiments, both plates are flexible under the compressing of a CROF process. In some embodiments, a plate is rigid and another plate is flexible under the compressing of a CROF process. In some embodiments, both plates are rigid. In some embodiments, both plates are flexible but have different flexibility.

B-2. Method of Lateral Filtering

Another aspect of the present invention provides a method of filtering a sample using the device of the present invention. In some embodiments, the method comprises the steps of:
 (a) providing a first, a second plate, and a nanostructured filter, wherein:
  i. the plates are movable relative to each other into different configurations, including an open configuration and a closed configuration;
  ii. one or both plates are flexible;
  iii. each of the plates has an inner surface, and the first plate has an unfiltered area at one location and a filtered area at another location, wherein the unfiltered area is for contacting a composited liquid sample containing a component to be separated, and the filtered area for contacting a filtering product of at least part of the sample; and
  iv. the nanostructured filter is fixed to the respective inner surface of one or both of the plates;
 (b) depositing the composite liquid sample on the unfiltered area or the second plate inner surface in the open configuration,
  wherein in the open configuration, the two plates are partially or entirely separated apart, and the spacing between the plates allows the sample to be deposited on the unfiltered area or the second plate inner surface; and
 (c) separating the component from at least part of the deposited sample by compressing the two plates into the closed configuration with a conformable force,
  wherein in the closed configuration, the nanostructured filter is positioned between the unfiltered and filtered areas and contacts the inner surfaces of both plates, and said part of the deposited sample is compressed by the two plates to flow from the unfiltered area to the filtered area through the nanostructured filter, forming a filtering product, and
  wherein the nanostructured filter is configured to separate the component from said at least part of the sample.

B-3. Other Examples of the Filtering Device

Figure 28:
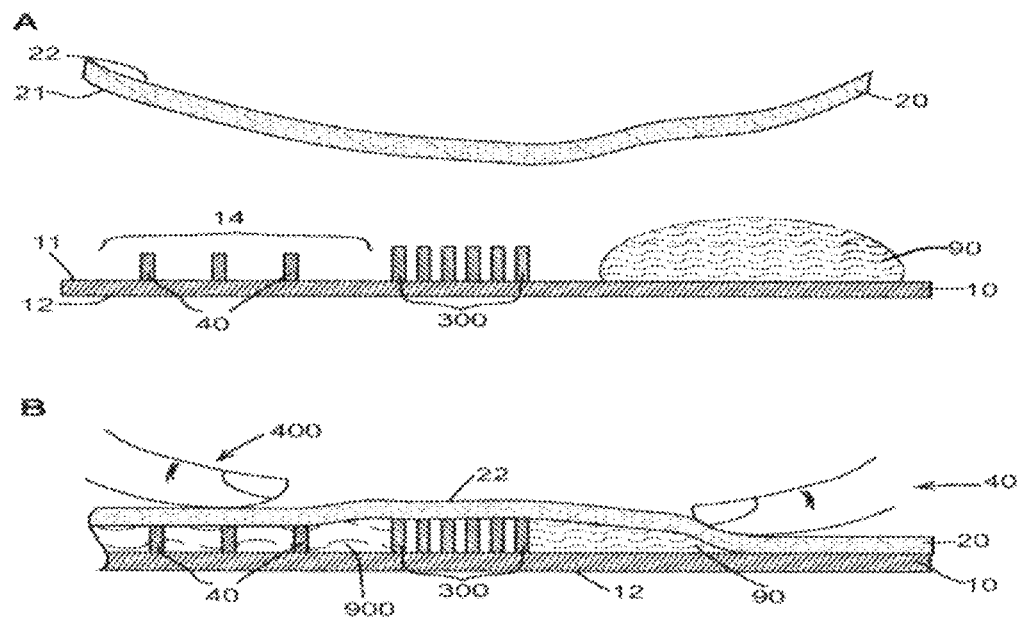
FIG. 28 shows schematically another exemplary embodiment of the device and method for lateral filtering provided by the present invention.

FIG. 28 schematically shows another exemplary embodiment of the device for sample filtering. The device comprises a first plate 10, a second plate 20, a nanostructured filter 300, and second spacers 42. Both the first plate 10 and the second plate 20 comprise an inner surface, 11 and 21, respectively. The first plate comprises, on its inner surface 11, an unfiltered area 13 and a filtered area 14. The unfiltered area 13 is for contacting a composited liquid sample that contains a target-filtering component 92 to be removed by the device, and the filtered are 14 for contacting a filtering product of the sample in which the target-filtering component 92 is removed. The nanostructured filtered 300 is fixed to the first plate inner surface 11. Moreover, the second spacers 42 are fixed to the filtered area of the first plate inner surface 11.

Similar to FIG. 27, the first plate 10 and second plate 20 in FIG. 28 are also relatively movable to each other into different configurations, including an open configuration and a closed configuration. Panel (A) shows an embodiment of the open configuration, in which: the two plates are separated apart, and the spacing between the two plates allows the sample 90 that contains target-filtering components 92 to be removed to be deposited on the unfiltered area 13 or the second plate inner surface 21 (not shown). It should be noted here that, in some embodiments, the separation between the two plates at the open configuration is partial, i.e. the two plates touch each other at areas other than the unfiltered area. In some embodiments, both the two plates touch the second spacers at the open configuration, while separated apart over the unfiltered area.

FIG. 28 panel (B) depicts the closed configuration of the exemplary device and two human fingers that facilitate the conversion of the device form the open configuration to the closed configuration. In particular, similar to FIG. B1 panel (C), the human finger 600 compresses the two plates over the unfiltered are into the closed configuration. As a result, the deposited 90 is compressed by the two plates, and part of the sample 90 is forced to flow through the nanostructured filter 300 from the unfiltered 13 to the filtered area 14. The nanostructured filter 300 is configured to separate the target-filtering component 92 from the part of the sample 90 that flows through, forming the filtering product 900. The difference here, however, from FIG. 27 is that the filtering product over the filtered area is also compressed by the two plates at the closed configuration. A different human finger 602 is illustrated to compress the two plates over the filtered area 14. At the closed configuration, the spacing between the two plates over the filtered area 14 is regulated by the height of the second spacers 42, and thus the filtering product 900 is compressed into a second thin layer confined by the inner surfaces of the two plates. In some embodiments, the second spacers 42 have a second uniform height. In some embodiments, the second spacers 42 have a second uniform inter-spacer distance. In some embodiments, the second thin layer is a second layer of uniform thickness that is regulated by the second uniform height of the second spacers.

Figure 29:
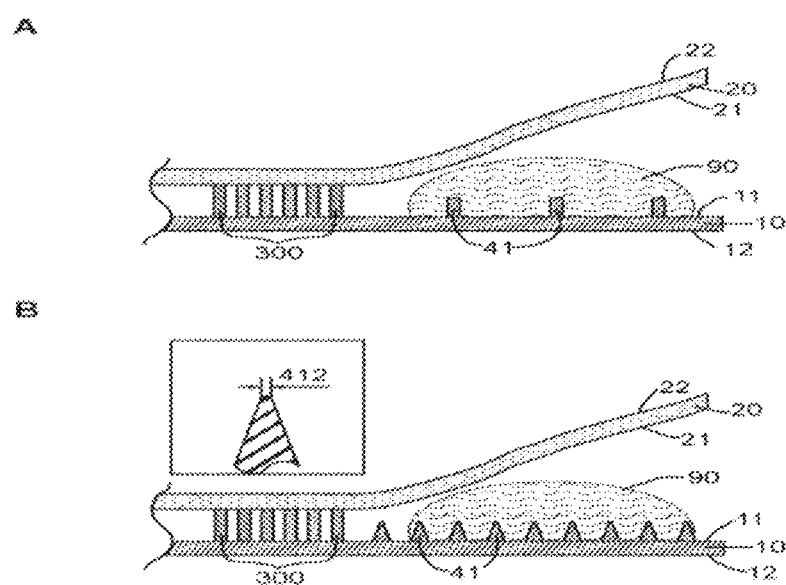
FIG. 29 shows schematically another exemplary embodiment of the device and method for lateral filtering and sample assay/reaction/processing as provided by the present invention.

FIG. 29 schematically illustrates other embodiments of the device for sample filtering according to the present invention. In addition to having the similar components, i.e. the first plate 10, the second plate 20, and the nanostructured filter 300, and their structural features illustrated in FIG. B1 and elaborated above, the device in FIG. 29 further comprises a plurality of first spacers 41, as shown in panel (A), or a plurality of lysing pillars 44, as shown in panel (B).

Referring to FIG. 29 panel (A), the first spacers 41 are fixed to the unfiltered area 13. It should be noted, however, that in other embodiments, the first spacers 41 are fixed to either the second plate inner surface 21, or the inner surfaces of the two plates (11 and 21). In the open configuration, the two plates are partially or completely separated apart, and the spacing between the two plates over the unfiltered area 13 is not regulated by the height of the first spacers 41, allowing a sample containing the target-filtering component 92 to be deposited over the unfiltered area 13. In the closed configuration (not illustrated here), at least part of the first spacers 41 are over the unfiltered area13, the spacing between the two plates over the unfiltered area 13 is regulated by the height of the first spacers 41, and at least a first part of the deposited sample 92 is compressed by the two plates into a first thin layer over the unfiltered area, and at least a second part of the sample 92 is compressed by the two plates to flow through the nanostructured filter 300 from the unfiltered area 13 to the filtered area 14, forming the filtering product. In some embodiments, the first spacers 41 have a first uniform height. In some embodiments, the first spacers 41 have a first uniform inter-spacer distance. In some embodiments, the first thin layer is a first layer of uniform thickness that is regulated by the uniform height of the first spacers.

Referring to FIG. 29 panel (B), the device is capable of both lysing a target-lysing component 94 and filtering a target-filtering component 92 that are contained in the composite liquid sample. The lysing pillars 44 are fixed to the unfiltered area 13 of the first plate inner surface 11. In other embodiments, the lysing pillars 44 are fixed to either the second plate inner surface 21, or the inner surfaces of both plates (11 and 21). The lysing pillars 44 have a top surface with at least one of its lateral dimensions (e.g. diameter 412 as shown in the inset) being less than half of the maximum lateral dimension of a target-lysing component 94 in the sample. The first plate 10 and the second plate 20 are also movable relative to each other into the two configurations, the open configuration and the closed configuration. Compared to the device in FIG. B1, additional features of the device in FIG. 29 panel (B) include: (1) in the open configuration, the spacing between the two plates over the unfiltered area is not regulated by the height of the lysing pillars 40, allowing the liquid composite sample 90 that contains the target-lysing component 94 and the target-filtering component 92 to be deposited over the unfiltered area; (2) in the closed configuration, at least part of the lysing pillars 44 are over the unfiltered area 13 and mechanically lyse a substantial portion of the target-lysing component 94 in the deposited sample, and at least a part of the deposited sample is compressed by the two plates to flow through the nanostructured filter form the unfiltered area to the filtered area.

Other Examples of Present Invention

AA1 A device for performing assay, comprising:
  a first plate that comprises, on its inner surface, a sample loading zone, open flow channel, reaction zone, and, optionally, passive pumping zone;
  a second plate that comprises a flat inner surface, wherein
    i. the first and second plates are movable relative to each other into different configurations;
    ii. the sample loading zone comprises a well below the plate surface and is configured for loading a fluidic sample that contains an analyte;
    iii. the open flow channel is fluidically connected to the sample loading zone and the reaction zone, and is configured to guide the sample to flow from the sample loading zone to the reaction zone;
    iv. one of the configurations is an open configuration, in which: the two plates are partially or entirely separated apart, the spacing between the plates is not regulated by the spacers, and the sample is deposited on one or both of the plates; and
    v. another of the configurations is a closed configuration, which is configured after the sample deposition in the open configuration, and in the closed configuration: at least one spacer is between the two plates, at least part of the sample deposited is compressed by the plates into a layer of substantially uniform thickness and is substantially stagnant relative to the plates, wherein the uniform thickness of the layer is confined by the inner surfaces of the two plates and is regulated by the plates and the spacers.

AB1. A method of performing assay, comprising the steps of:
  (a) obtaining a liquid sample;
  (b) obtaining a device for performing assay, comprising:
    a first plate that comprises, on its inner surface, a sample loading zone, open flow channel, reaction zone, and, optionally, passive pumping zone;
    a second plate that comprises a flat inner surface, wherein
      i. the first and second plates are movable relative to each other into different configurations;
      ii. the sample loading zone comprises a well below the plate surface and is configured for loading a fluidic sample that contains an analyte; and
      iii. the open flow channel is fluidically connected to the sample loading zone and the reaction zone, and is configured to guide the sample to flow from the sample loading zone to the reaction zone;
  (c) depositing the sample onto the sample loading zone of the first plate, when the two plates are at an open configuration, wherein the open configuration is one of the configurations, in which: the two plates are partially or entirely separated apart, the spacing between the plates is not regulated by the spacers, and the sample is deposited on one or both of the plates; and
  (d) after sample deposition in (c), compressing the two plates into a closed configuration, wherein the closed configuration is another of the configurations, which is configured after the sample deposition in the open configuration, and in the closed configuration: at least one spacer is between the two plates, at least part of the sample deposited is compressed by the plates into a layer of substantially uniform thickness and is substantially stagnant relative to the plates, wherein the uniform thickness of the layer is confined by the inner surfaces of the two plates and is regulated by the plates and the spacers.

BA1. A device for separating a component from a composite liquid sample, comprising:
  a first plate, a second plate, and a nanostructured filter, wherein:
    viii. the plates are movable relative to each other into different configurations, including an open configuration and a closed configuration;
    ix. one or both plates are flexible;
    x. each of the plates has an inner surface, and the first plate has, on its inner surface, an unfiltered area at one location and a filtered area at another location, wherein the unfiltered area is for contacting a composited liquid sample containing a component to be separated, and the filtered area for contacting a filtering product of at least part of the sample; and
    xi. the nanostructured filter that is fixed to the respective inner surface of one or both of the plates;
      wherein in the open configuration, the two plates are partially or entirely separated apart, and the spacing between the plates allows the sample to be deposited on the unfiltered area or the second plate inner surface; and
      wherein the closed configuration is configured after deposition of the sample in the open configuration, and in which: the nanostructured filter is positioned between the unfiltered and filtered areas and contacts the inner surfaces of both plates, and at least part of the deposited sample is compressed by the two plates to flow from the unfiltered area to the filtered area through the nanostructured filter, forming a filtering product; and wherein the nanostructured filter is configured to separate the component from said at least part of the sample.

BA2. The device of any prior embodiment, wherein one or both of the plates comprise a plurality of second spacers that are fixed to the respective inner surface and positioned over the filtered area at the closed configuration, and have a second uniform height and a second uniform inter-spacer distance, and wherein in the closed configuration, the filtering product is compressed by the two plates into a layer of substantially uniform thickness that is confined by the two plates and regulated by the second spacers.

BA3. The device of any prior embodiment, wherein one or both of the plates comprise a plurality of first spacers that are fixed to the respective inner surface and positioned over the unfiltered area at the closed configuration.

BA4. The device of any prior embodiment, wherein the first spacers have a top surface with at least one of its lateral dimensions being less than half of the maximum lateral dimension of a biological structure to be lysed that is contained in the sample, and wherein the first spacers are configured to mechanically lyse the biological structure while the plates are being transformed from the open configuration to the closed configuration.

BA5. The device of any prior embodiment, wherein the first spacers have a first uniform height and a first uniform inter-spacer distance, and wherein in the closed configuration, the sample over the unfiltered area is compressed into a layer of substantially uniform thickness that is confined by the two plates and regulated by the first spacers.

BA6. The device of any prior embodiment, wherein the nanostructured filer comprises: weir filter, post filter, membrane filter, and any combination thereof.

BB1. A method for analyzing a composite liquid sample, comprising the steps of:
(d) providing a first, a second plate, and a nanostructured filter, wherein:
  v. the plates are movable relative to each other into different configurations, including an open configuration and a closed configuration;
  vi. one or both plates are flexible;
  vii. each of the plates has an inner surface, and the first plate has an unfiltered area at one location and a filtered area at another location, wherein the sample contact areas are for contacting a composited liquid sample containing a component to be separated; and
  viii. the nanostructured filter is fixed to the respective plate of one or both of the plates;
(e) depositing the composite liquid sample on the unfiltered area or the second plate inner surface in an open configuration,
  wherein the open configuration is one of the configurations, in which: the two plates are partially or entirely separated apart, and the spacing between the plates allows the sample to be deposited on the unfiltered area or the second plate inner surface; and
(f) separating the component from at least part of the deposited sample by compressing the two plates into a closed configuration with a conformable force,
  wherein the closed configuration is another of the configurations, which is configured after the sample deposition in the open configuration, and in the closed configuration: the nanostructured filter is positioned between the unfiltered and filtered areas and contacts the inner surfaces of both plates, and said part of the deposited sample is compressed by the two plates to flow from the unfiltered area to the filtered area through the nanostructured filter, forming a filtering product, and
  wherein the nanostructured filter is configured to separate the component from said at least part of the sample.

BB2. The method of paragraph B1, wherein one or both of the plates comprise a plurality of second spacers that are fixed to the respective inner surface and positioned over the filtered area at the closed configuration, and have a second uniform height and a second uniform inter-spacer distance, and wherein the method further comprises:
(g) analyzing the filtering product in the closed configuration,
  wherein in the closed configuration, the filtering product is compressed by the two plates into a layer of substantially uniform thickness, wherein the uniform thickness is confined by the filtered areas of the two plates and regulated by the second spacers.

BB3. The method of any prior embodiment, wherein:
  i. one or both of the plates comprise a plurality of first spacers that are fixed to the respective inner surface and positioned over the unfiltered area at the closed configuration,
  ii. the first spacers have a top surface with at least one of its lateral dimensions being less than half of the maximum lateral dimension of a biological structure to be lysed that is contained in the sample, and
  iii. the first spacers are configured to mechanically lyse the biological structure while the plates are being transformed from the open configuration to the closed configuration.

BB4. The method of any prior embodiment, wherein one or both of the plates comprise a plurality of first spacers that are fixed to the respective inner surface and positioned over the unfiltered area at the closed configuration, and have a first uniform thickness and a first uniform inter-spacer distance, and wherein the method further comprises:
(e) analyzing the sample over the unfiltered area in the closed configuration,
  wherein in the closed configuration, the sample over the unfiltered area is compressed into a layer of substantially uniform thickness that is confined by the two plates and regulated by the first spacers.

BB5. The method of any prior embodiment, wherein the conformable force is provided by a human hand.

BBB5. The method of any prior embodiment, wherein the conformable force is provided by a pressured liquid, a pressed gas, or a conformal material.

BB6. The method of any prior embodiment, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

BB7. The method of any prior embodiment, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

BB8. The method of any prior embodiment, wherein the sample is an environmental gaseous sample from a source selected from the group consisting of: the air, underwater heat vents, industrial exhaust, vehicular exhaust, and any combination thereof.

BB9. The method of any prior embodiment, wherein the sample is a foodstuff sample selected from a group the group consisting of: raw ingredients, cooked food, plant and animal sources of food, preprocessed food, and partially or fully processed food, and any combination thereof.

BB10. The method of any prior embodiment, wherein the sample is human blood, and the depositing step comprises: (a) pricking the skin of a human release a droplet of blood onto the skin; and (b) contacting the droplet of blood with the filter without use of a blood transfer tool.

BB11. The method of any prior embodiment, wherein the biological structure to be lysed is selected from the group consisting of: red blood cells, white blood cells, platelets, and any combination thereof.

BB12. The method of any prior embodiment, wherein the component to be separated is selected from the group consisting of: cells, tissues, proteins, peptides, DNAs, RNAs, oligonucleotides, and any combination thereof.

What is claimed is:

1. A method for an affinity binding assay comprising:
   (a) providing a first plate, a second plate, and spacers, wherein:
      (i) the first plate and second plate are movable relative to each other into different configurations, including an open configuration and a closed configuration;
      (ii) each of the plates comprises an inner surface having a sample contact area for contacting a sample that contains or is suspected of containing a target analyte;
      (iii) the first plate comprises, on its inner surface, a binding site that contains a binding agent capable of binding the target analyte;
      (iv) the second plate comprises, on its inner surface, a storage site that contains a detection agent and a controlled release agent, wherein the controlled release agent is mixed with or coated on top of the detection agent;
      (v) the spacers have a pillar shape and are fixed to the respective inner surface of one or both of the plates, at least one of the spacers is inside and fixed on the sample contact area of one or both of the plates, and the spacers have a predetermined inter-spacer distance;
   (b) depositing the sample on the inner surface of at least one of the two plates when the two plates are in the open configuration, in which: the first and second plates are partially or entirely separated apart, and the spacing between the first and second plates is not regulated by the spacers;
   (c) compressing at least part of the deposited sample by bringing the two plates into the closed configuration, in which: said at least part of the deposited sample is compressed into a layer sandwiched between the first and second plates and having a thickness of 200 microns or less, wherein the spacers inside the sample contact area contact the inner surfaces of both the first and second plates to regulate the thickness of the layer;
   (d) releasing the detection agent into the layer through the controlled release agent, wherein the controlled release agent is capable of rendering the detection agent substantially released at a time point after the first and second plates are compressed into the closed configuration and the sample surface contacts the controlled release agent; and
   (e) after step (d), incubating the assay for a time period no shorter than an average time for the detection agent to diffuse across the thickness of the layer,
   (f) detecting the analyte in the layer using a detector and analyzing the target analyte in the layer,
   wherein the detection agent and the binding agent are capable of binding either directly or indirectly to generate a signal indicative of the presence or quantity of the target analyte;
   wherein in the direct binding, the detection agent competes with the target analyte and directly binds to the binding agent; and
   wherein in the indirect binding, the binding agent and the detection agent bind to a different location of the target analyte.

2. The method of claim 1, wherein the second plate comprises, on its inner surface, a first storage site that contains a first detection agent and a first controlled release agent, and a second storage site that contains a second detection agent and a second controlled release agent, wherein the first and second controlled release agents are mixed with or coated on top of the first and second detection agent, respectively;
   wherein the first and second detection agents bind to or react with the target analyte; and
   wherein the first and second controlled release agents are capable of rendering the first and second detection agents substantially released into the sample at different first and second time points, respectively.

3. The method of claim 1, wherein the storage site comprises more than two controlled release agents at different locations, and each of them renders a different release time for the detection agent at the respective location.

4. The method of claim 3, wherein the number of different types of controlled release agents is 3 or more.

5. The method of claim 2, wherein the first and second detection agents are released at different time.

6. The method of claim 1, wherein the controlled release agent is a slow release agent that is mixed with or coated on top of the detection agent; the spacers have a pillar shape and a flat top; and
   wherein the slow release agent is capable of autonomously rendering the detection agent substantially released at a first time point after the target analyte is substantially bound to the binding agent.

7. The method of claim 1, wherein the controlled release agent is a slow release agent that is mixed with or coated on top of the detection agent; and
   the spacers have a pillar shape and a flat top;
   wherein the detection agent is capable of binding to or reacting with the target analyte; and
   wherein the slow release agent is capable of autonomously rendering the detection agent substantially released at a first time point after the two plates are compressed into the closed configuration.

8. The method of claim 1, wherein the controlled release agent is a slow release agent that is mixed with or coated on top of the detection agent; and
   wherein the slow release agent is capable of being specifically responsive to a stimulus, retaining the detection agent on the second plate in the absence of the stimulus and releasing the detection agent upon receipt of the stimulus.

9. The method of claim 1, wherein
the spacers have a predetermined substantially uniform height that is equal to or less than 200 microns, and a predetermined fixed inter-spacer-distance; and
the fourth power of the inter-spacer-distance (ISD) divided by the thickness (h) and the Young's modulus (E) of the flexible plate (ISD$^4$/(hE)) is $5 \times 10^6$ µm$^3$/GPa.

10. The method of claim 1, wherein the controlled release agent is a stimulus-sensitive release agent that is mixed with or coated on top of the detection agent;
wherein the detection agent is capable of binding to or reacting with the target analyte; and
wherein the stimulus-dependent release agent is capable of being specifically responsive to a stimulus, retaining the detection agent on the plate in the absence of the stimulus and releasing the detection agent upon receipt of the stimulus.

11. The method of claim 6, wherein the slow release agent is soluble in the sample and capable of substantially resolving in the sample no earlier than the first time point.

12. The method of claim 6, wherein the slow release agent is insoluble in the sample and limits the contact of the detection agent by the sample.

13. The method of claim 6, wherein the slow release agent is made from a material selected from the group consisting of: PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

14. The method of claim 1, wherein the spacers have a maximum height of 200 µm or less.

15. The method of claim 1, wherein the spacers have a predetermined substantially uniform height that is 20 µm or less.

16. The method of claim 1, wherein the spacers have a predetermined constant inter-spacer distance.

17. The method of claim 1, wherein the spacers are fixed to the inner surface of one or both of the first and second plates.

18. The method of claim 1, wherein the layer has a substantially uniform thickness that is about the height of the spacers.

19. The method of claim 10, wherein the stimulus-dependent release agent forms cross-links with the detection agent that retain the detection agent in the absence of the stimulus, and wherein the cross-links are altered by the stimulus, resulting in the release of the detection agent.

20. The method of claim 10, wherein the stimulus-dependent release agent is capable of forming polymer autonomously that retains the detection agent in the absence of the stimulus, and wherein the polymer is depolymerized by the stimulus, resulting in the release of the detection agent.

21. The method of claim 10, wherein the stimulus is selected from the group consisting of: radio wave, microwave, infrared radiation, visible light, ultraviolet radiation, X-rays, gamma rays, temperature, pH, ion, magnetic stimulus, mechanical stimulus, and electrical stimulus.

22. The method of claim 10, wherein the stimulus-dependent release agent is made from a material selected from the group consisting of: (E)-(2-Hydroxyphenyl)acrylates, 2-Aroylbenzoates, Xanthenoic esters, 2-Nitrobenzyl derivatives, 1-Alkoxy-9,10-anthraquinones, 2-Oxoacetates, Alkyl phenyl ketones, 4-benzoyl-phenylalanine, amino-coumarin family, Perylene, 1-Acetylperylene, 2-nitrophenyl) propryloxycarbonyl, Ruthenium complex, Chlorophyllin, Phthalocyanin, Distearoyl indocarbocyanine, Azobenzene, 2-diazo-1,2-nathoquinone, Merocyanine/spiropyran, Donor-acceptor stenhouse adducts, coumarin-modified mesoporous bioactive glass, N-isopropylacrylamide, N, N-dimethylaminoethyl methacrylate (PNIPAm-co-PDMAEMA), Linear PNI-Pam-co-DMAEMA Polymer, PEI-PNIPAm polymer with 46-kDa PNIPAm grafts, Poly[2-(2-ethoxy) ethoxy ethylvinyl ether (EOEOVE), Multiblock copolymers synthesized from pluronic and di-(ethylene glycol) divinyl ether, Polyethylenimine (BPEI)/pDNA complex, Co-polymerization of PVP and acrylic acid, Pluronic-g-PAA copolymers, Liposomes attached with a saccharide vector, PEGylated liposome, Copolymer of N-isopropylacryl amide and acryloylpyrrolidine, Histidine-modified galactosylated cholesterol derivative—cationic liposome, Anionic liposomes containing phosphatidylethanolamine (PE), Amphiphilic co-polymer of poly (methoxy-polyethylene glycol cyanoacrylate-c0-n-hexadecyl cyano acrylate) (PEG-PH DCA), Polyethylene Poly (phthaloyl-L-lysine), Polyamidoamine dendrimer, Poly (alkylcyanoacrylate) nanoparticles, Poly (methylmethacrylate) Nanoparticles, Poly (alkylcyanoacrylate) Polyester Nanoparticles, Albumin, Chitosan, Dextran, Poly (N-isopropylacrylamidecobutylmethacrylate-co-acrylic acid), Poly (N-isopropylacrylamide, polysaccharides, gelrite, alginate/HPmC, sod alginate/HPC, gelrite gellan gum, and tamarind.

23. The method of claim 1, wherein the controlled release agent is a slow release agent that is capable of autonomously rendering the detection agent substantially released at the first time point, and wherein the releasing step (d) is performed without external actions.

24. The method of claim 1, wherein the controlled release agent is a stimulus-sensitive agent that is capable of being specifically responsive to a stimulus, retaining the detection agent on the plate in the absence of the stimulus and releasing the detection agent upon receipt of the stimulus, and wherein the releasing step (d) comprises: after the target analyte in the layer is substantially bound to the binding agent, delivering the stimulus to the stimulus-dependent agent to trigger the release of the detection agent into the layer.

25. The method of claim 2, wherein at least one of the controlled release agents is a slow release agent that is capable of autonomously rendering the detection agent substantially released at the respective first time point.

26. The method of claim 2, wherein at least one of the controlled release agents is a stimulus-sensitive agent that is capable of being specifically responsive to a stimulus, retaining the detection agent on the plate in the absence of the stimulus and releasing the detection agent upon receipt of the stimulus.

27. The method of claim 7, wherein the slow release agent is soluble in the sample and capable of substantially dissolving in the sample no earlier than the first time point.

28. The method of claim 7, wherein the slow release agent is insoluble in the sample and limits the contact of the detection agent by the sample.

29. The method of claim 8, wherein the slow release agent is insoluble in the sample and limits the contact of the detection agent by the sample.

30. The method of claim 7, wherein the slow release agent is made from a material selected from the group consisting of: PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

31. The method of claim 8, wherein the slow release agent is made from a material selected from the group consisting of: PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

32. The method of claim 2, wherein the spacers have a maximum height of 200 µm or less.

33. The method of claim 2, wherein the spacers have a predetermined substantially uniform height that is 20 µm or less.

34. The method of claim 2, wherein the spacers are fixed to the inner surface of one or both of the first and second plates.

35. The method of claim 2, wherein the layer has a substantially uniform thickness that is about the height of the spacers.

36. The method of claim 6, wherein the spacers have a maximum height of 200 µm or less.

37. The method of claim 6, wherein the spacers have a predetermined substantially uniform height that is 20 µm or less.

38. The method of claim 6, wherein the spacers have a predetermined constant inter-spacer distance.

39. The method of claim 6, wherein the spacers are fixed to the inner surface of one or both of the first and second plates.

40. The method of claim 6, wherein the layer has a substantially uniform thickness that is about the height of the spacers.

41. The method of claim 7, wherein the spacers have a maximum height of 200 µm or less.

42. The method of claim 7, wherein the spacers have a predetermined substantially uniform height that is 20 µm or less.

43. The method of claim 7, wherein the spacers have a predetermined constant inter-spacer distance.

44. The method of claim 7, wherein the spacers are fixed to the inner surface of one or both of the first and second plates.

45. The method of claim 7, wherein the layer has a substantially uniform thickness that is about the height of the spacers.

46. The method of claim 8, wherein the spacers have a maximum height of 200 µm or less.

47. The method of claim 8, wherein the spacers have a predetermined substantially uniform height that is 20 µm or less.

48. The method of claim 8, wherein the spacers have a predetermined constant inter-spacer distance.

49. The method of claim 8, wherein the spacers are fixed to the inner surface of one or both of the first and second plates.

50. The method of claim 8, wherein the layer has a substantially uniform thickness that is about the height of the spacers.

51. The method of claim 9, wherein the spacers have a maximum height of 200 µm or less.

52. The method of claim 9, wherein the spacers have a predetermined substantially uniform height that is 20 µm or less.

53. The method of claim 9, wherein the spacers have a predetermined constant inter-spacer distance.

54. The method of claim 9, wherein the spacers are fixed to the inner surface of one or both of the first and second plates.

55. The method of claim 9, wherein the layer has a substantially uniform thickness that is about the height of the spacers.

56. The method of claim 10, wherein the spacers have a maximum height of 200 µm or less.

57. The method of claim 10, wherein the spacers have a predetermined substantially uniform height that is 20 µm or less.

58. The method of claim 10, wherein the spacers have a predetermined constant inter-spacer distance.

59. The method of claim 10, wherein the spacers are fixed to the inner surface of one or both of the first and second plates.

60. The method of claim 10, wherein the layer has a substantially uniform thickness that is about the height of the spacers.

61. The method of claim 2, wherein the spacers have a predetermined constant inter-spacer distance.

62. The method of claim 1, wherein the detection agent comprises a protein, a nucleic acid, or a molecule.

63. The method of claim 1, wherein the spacer has a flat top.

64. The method of claim 1, wherein the sample comprises a biological sample selected from the group consisting of amniotic fluid, aqueous humour, vitreous humour, blood breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

65. The method of claim 1, wherein the analyte is selected from the group consisting of a molecule, cells, tissues, viruses, and nanoparticles with different shapes.

66. The method of claim 16, wherein the inter-spacer distance is substantially periodic.

67. The method of claim 16, wherein the inter-spacer distance is in the range of 7 µm to 120 µm.

68. The method of claim 1, wherein the method analyzes the sample in 60 seconds or less.

69. The method of claim 1, wherein the method analyzes the sample in 10 seconds or less.

70. The method of claim 1, wherein the binding site is a dry binding site comprising a capture agent.

71. The method of claim 70, wherein the capture agent comprises an antibody or nucleic acid.

72. The method of claim 70, wherein the dry binding site comprises a releasable dry reagent.

73. The method of claim 72, wherein the releasable dry reagent is a labeled reagent.

74. The method of claim 72, wherein the releasable dry reagent is a fluorescently-labeled reagent.

75. The method of claim 72, wherein the releasable dry reagent is a fluorescently-labeled antibody.

76. The method of claim 72, wherein the releasable dry reagent comprises chemicals used as color indicators.

77. The method of claim 72, wherein the releasable dry reagent is a cell stain.

78. The method of claim 72, wherein the releasable dry reagent is a cell lysing reagent.

79. The method of claim 1, wherein the detector is an optical detector that detects an optical signal.

80. The method of claim 1, wherein the detector is an electric detector that detects electrical signal.

81. The method of claim 1, wherein one or both of the plates comprise multiple binding sites that contain capture agents of different concentrations.

82. The method of claim 1, wherein the binding site comprises at least two binding sites at different locations on the first plate or the second plate.

83. The method of claim 1, wherein the storage site comprises at least two storage sites at different locations on the first plate or the second plate.

84. The method of claim 1, further comprising a step of washing the plates in a closed configuration.

85. The method of claim 16, wherein a fourth power of the inter-spacer distance (ISD) divided by the thickness (h) and the Young's modulus (E) of the first plate or the second plate ($ISD^4/(hE)$) is $5 \times 10^5$ $\mu m^3$/GPa or less.

86. The method of claim 1, wherein the thickness of the first plate times the Young's modulus of the first plate is in the range 60 to 750 GPa-μm, or the thickness of the second plate times the Young's modulus of the second plate is in the range 60 to 750 GPa-μm.

87. The method of claim 1, wherein the thickness of the first plate times the Young's modulus of the first plate is in the range of 60 to 750 GPa-μm, and a fourth power of the inter-spacer-distance (ISD) divided by the thickness (h) and the Young's modulus (E) of the first plate or the second plate ($ISD^4/(hE)$) is $5 \times 10^5$ $\mu m^3$/GPa or less.

88. The method of claim 1, further comprising a slow release agent.

89. The method of claim 88, wherein the slow release agent comprises a stimulus-dependent release agent.

90. The method of claim 88, wherein the slow release agent causes different release times.

91. The method of claim 88, wherein the slow release agent comprises a temporally and spatially controlled release.

92. The method of claim 88, wherein the slow release agent comprises PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], or HPC (Hydroxypropyl cellulose).

93. The method of claim 89, wherein the stimulus-dependent release agent is dependent on an electromagnetic wave stimulus.

94. The method of claim 1, wherein one or both of the plates comprises multiple binding sites that contain capture agents.

95. The method of claim 1, wherein a distance between the two plates that is regulated by the spacers comprises a gap size in the range of 10 μm to 30 μm.

96. The method of claim 1, wherein a distance between the two plates that is regulated by the spacers comprises a gap size in the range of 30 μm to 50 μm.

97. The method of claim 1, further comprising, on the second plate, more than two controlled release agents at different locations, and each of them renders a different release time for the detection agent at the respective location.

98. The method of claim 1, further comprising, on the second plate, a number of different types of controlled release agent that is 3 or more.

99. The method of claim 1, wherein the controlled release agent is a stimulus-dependent release agent that forms cross-links with the detection agent and wherein the stimulus-dependent release agent retains the detection agent in the absence of the stimulus, and wherein the cross-links are altered by the stimulus, resulting in the release of the detection agent.

100. The method of claim 1, wherein the controlled release agent is a stimulus-dependent release agent that forms a polymer autonomously, wherein said polymer retains the detection agent in the absence of the stimulus, and wherein the polymer is depolymerized by the stimulus, resulting in the release of the detection agent.

101. The method of claim 1, wherein the controlled release agent is a stimulus-dependent release agent, and wherein the stimulus is selected from the group consisting of radio wave, microwave, infrared radiation, visible light, ultraviolet radiation, X-rays, and gamma rays, temperature, pH, ion, magnetic stimulus, mechanical stimulus, and electrical stimulus.

102. The method of claim 1, wherein the controlled release agent is a stimulus-dependent release agent, and wherein the stimulus-dependent release agent is made from a material selected from the group consisting of: (E)-(2-Hydroxyphenyl)acrylates, 2-Aroylbenzoates, Xanthenoic esters, 2-Nitrobenzyl derivatives, 1-Alkoxy-9,10-anthraquinones, 2-Oxoacetates, Alkyl phenyl ketones, 4-benzoylphenylalanine, amino-coumarin family, Perylene, 1-Acetylperylene, 2-nitrophenyl)propryloxycarbonyl, Ruthenium complex, Chlorophyllin, Phthalocyanin, Distearoyl indocarbocyanine, Azobenzene, 2-diazo-1,2-nathoquinone, Merocyanine/spiropyran, Donor-acceptor stenhouse adducts, coumarin-modified mesoporous bioactive glass, N-isopropylacrylamide, N, N-dimethylaminoethyl methacrylate (PNIPAm-co-PDMAEMA), Linear PNI-Pam-co-DMAEMA Polymer, PEI-PNIPAm polymer with 46-kDa PNIPAm grafts, Poly[2-(2-ethoxy) ethoxy ethylvinyl ether (EOEOVE), Multiblock copolymers synthesized from pluronic and di-(ethylene glycol) divinyl ether, Polyethylenimine (BPEI)/pDNA complex, Co-polymerization of PVP and acrylic acid, Pluronic-g-PAA copolymers, Liposomes attached with a saccharide vector, PEGylated liposome, Copolymer of N-isopropylacryl amide and acryloylpyrrolidine, Histidine-modified galactosylated cholesterol derivative—cationic liposome, Anionic liposomes containing phosphatidylethanolamine (PE), Amphiphilic co-polymer of poly (methoxy-polyethylene glycol cyanoacrylate-c0-n-hexadecyl cyano acrylate) (PEG-PH DCA), Polyethylene Poly (phthaloyl-L-lysine), Polyamidoamine dendrimer, Poly (alkylcyanoacrylate) nanoparticles, Poly (methylmethacrylate) Nanoparticles, Poly (alkylcyanoacrylate) Polyester Nanoparticles, Albumin, Chitosan, Dextran, Poly (N-isopropylacrylamidecobutylmethacrylate-co-acrylic acid), Poly (N-isopropylacrylamide, polysaccharides, gelrite, alginate/HPmC, sod alginate/HPC, gelrite gellan gum, and tamarind.

103. The method of claim 1, wherein the controlled release agent is a slow release agent that is made from a material selected from the group consisting of: PVP (polyvinylpyrrolidone), PVA [poly(vinyl alcohol)], PEO [poly(ethylene oxide)], HPMC (hydroxypropyl methyl cellulose), HPC (hydroxypropyl cellulose), MC (methyl cellulose), soluble starch, dextran, gelatin, chitosan, PEOx [Poly(2-ethyl-2-oxazoline)], and HPC (Hydroxypropyl cellulose).

104. The method of claim 70, further comprising a controlled release agent that is mixed with or coated on top of the capture agent.

* * * * *